(12) United States Patent
Bauer et al.

(10) Patent No.: US 11,801,271 B2
(45) Date of Patent: *Oct. 31, 2023

(54) STABLE BACTERIAL EXTRACTS AS PHARMACEUTICALS

(71) Applicant: OM PHARMA SA, Meyrin (CH)

(72) Inventors: Jacques Bauer, St-Prex (CH); Christian Pasquali, Prangins (CH)

(73) Assignee: OM PHARMA SA, Meyrin (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/474,242

(22) Filed: Sep. 14, 2021

(65) Prior Publication Data
US 2021/0401902 A1    Dec. 30, 2021

Related U.S. Application Data

(63) Continuation-in-part of application No. PCT/EP2020/056742, filed on Mar. 12, 2020.

(30) Foreign Application Priority Data

Mar. 14, 2019  (EP) .................................... 19162912

(51) Int. Cl.
*A61K 35/742* (2015.01)
*A61P 31/14* (2006.01)
*A61K 35/744* (2015.01)

(52) U.S. Cl.
CPC .......... *A61K 35/742* (2013.01); *A61K 35/744* (2013.01); *A61P 31/14* (2018.01)

(58) Field of Classification Search
CPC ................ A61K 35/742; A61K 35/744; A61K 2039/55594; A61K 9/0043; A61K 9/0078; A61K 9/08; A61K 39/39; A61K 47/02; A61K 35/74; A61P 31/14; A61P 29/00;
(Continued)

(56) References Cited

U.S. PATENT DOCUMENTS

2006/0166307 A1 * 7/2006 Detraz .................. C12M 47/06
435/259

FOREIGN PATENT DOCUMENTS

| RU | 2425691 C1 | 8/2011 |
| RU | 2457848 C2 | 8/2012 |
| RU | 2500412 C2 | 12/2013 |

(Continued)

OTHER PUBLICATIONS

Townsend, J. C., W. A. Sadler, and G. M. Shanks. "The effect of storage pH on the precipitation of proteins in deep frozen urine samples." Annals of clinical biochemistry 24.1 (1987): 111-112. (Year: 1987).*

(Continued)

*Primary Examiner* — Lora E Barnhart Driscoll
*Assistant Examiner* — Candice Lee Swift
(74) *Attorney, Agent, or Firm* — WCF IP

(57) ABSTRACT

The present invention relates to novel stable bacterial extract preparations having substantial increased stability over time, novel methods of preparation thereof, pharmaceutical formulations based on these novel stabilized bacterial extracts, as well as novel routes of administration and delivery devices for treating and/or preventing acute and chronic immunological disorders resulting from infections and/or inflammation and/or neoplasms and/or dysbiosis.

25 Claims, 41 Drawing Sheets

Purification of Bacterial Extract

(58) Field of Classification Search
CPC . A61P 31/00; A61P 37/00; C12N 1/06; C12N 1/08; C12N 1/20; C12P 1/04
See application file for complete search history.

(56) References Cited

FOREIGN PATENT DOCUMENTS

| | | |
|---|---|---|
| RU | 2515054 C2 | 5/2014 |
| WO | 2008085549 A3 | 7/2008 |
| WO | 2008109667 A2 | 9/2008 |
| WO | 2008109667 A3 | 9/2008 |
| WO | 2008109669 A2 | 9/2008 |
| WO | 2010009892 A2 | 1/2010 |
| WO | 2010027344 A1 | 3/2010 |

OTHER PUBLICATIONS

Djupesland, Per Gisle. "Nasal drug delivery devices: characteristics and performance in a clinical perspective—a review." Drug delivery and translational research 3.1 (2013): 42-62. (Year: 2009).*
Braido, Fulvio, et al. "The bacterial lysate Lantigen B reduces the number of acute episodes in patients with recurrent infections of the respiratory tract: the results of a double blind, placebo controlled, multicenter clinical trial." Immunology Letters 162.2 (2014): 185-193. (Year: 2014).*
Usama Ramadan Abdelmohsen, Tanja Grkovic, Srikkanth Balasubramanian, Mohamed Salah Kamel, Ronald J. Quinn, Ute Hentschel, Elicitation of secondary metabolism in actinomycetes, Biotechnology Advances, (Year: 2015).*
Collins, Kim D. "Charge density-dependent strength of hydration and biological structure." Biophysical journal 72.1 (1997): 65-76. (Year: 1997).*
Lopalco, Antonio, et al. "Mechanism of decarboxylation of pyruvic acid in the presence of hydrogen peroxide." Journal of pharmaceutical sciences 105.2 (2016): 705-713. (Year: 2016).*
Notification concerning Transmittal of International Preliminary Report on Patentability (Chapter 1 of the Patent Cooperation Treaty) dated Sep. 23, 2021, for OM Pharma SA, International Application No. PCT/EP2020/056742, filed Mar. 12, 2019.
Dariusz Jurkiewicz et al: "Bacterial lysates in the prevention of respiratory tract infections", Otolaryngologia Polska—Journal of Polish Otolaryngology, vol. 72, No. 5, Oct. 31, 2018 (Oct. 31, 2018), pp. 1-8, XP055677143, PL ISSN: 0030-6657, DOI: 10.5604/01.3001.0012.7216.
Rial Analia et al: "Intranasal administration of a polyvalent bacterial lysate induces self-restricted inflammation in the lungs and a Th1/Th17 memory signature", Microbes and Infection, vol. 18, No. 12, pp. 747-757, XP029854802, ISSN: 1286-4579, DOI: 10.1016/J.MICINF.2016.10.006.
A. Rial et al: "Abstract", Infection and Immunity, vol. 72, No. 5, May 1, 2004 (May 1, 2004), pp. 2679-2688, XP055697816, us ISSN: 0019-9567, DOI: 10.1128/IAI.72.5.2679-2688.2004.
Michael Roth et al: "Broncho Vaxom (OM-85) modulates rhinovirus docking proteins on human airway epithelial cells via Erk1/2 mitogen activated protein kinase and cAMP", PLoS One 12(11): e0188010, https://doi.org/10.1371/journal.pone.0188010, Nov. 28, 2017.
J. Sramek et al: "Bacterial lysate (I.R.S. 19) applied intranasally in the prevention of acute respiratory diseases in children: a randomized double-blind study.", Jan. 1, 1986 (Jan. 1, 1986), XP055677072, Retrieved from the Internet: URL:http://www.ncbi.nlm.nih.gov/pubmed/3805711.
Vadim Pivniouk et al: "The OM-85 bacterial lysate inhibits SARS-CoV-2 infection of epithelial cells by downregulating SARS-CoV-2 receptor expression", J Allergy Clin Immunol (2021).
P. Hohensinner et al: "Modulation of the innate and adaptive immune system during coronavirus infection" (abstract), ERS International Congress 2021 (virtual).
L. Fang et al: "Exploring the molecular potential of bacterial lysates to reduce COVID-19 susceptibility of bronchial epithelial cells in vitro" (abstract), ERS International Congress 2021 (virtual).
Philipp Hohensinner: "Emerging respiratory diseases: state-of-the-art studies of SARS-CoV-2 infection" (oral presentation), published on Sep. 8, 2021 at the ERS conference.
B. Marsland et al: "Direct OM-85 nasal administration is superior to oral treatment in a superinfection model", Sep. 21, 2021 (poster).
Birnboim, H. C., & Doly, J.(1979). A rapid alkaline extraction procedure for screening recombinant plasmid DNA. Nucleic acids research, 7(6), 1513-1523.

* cited by examiner

Purification of Bacterial Extract

Figure 19
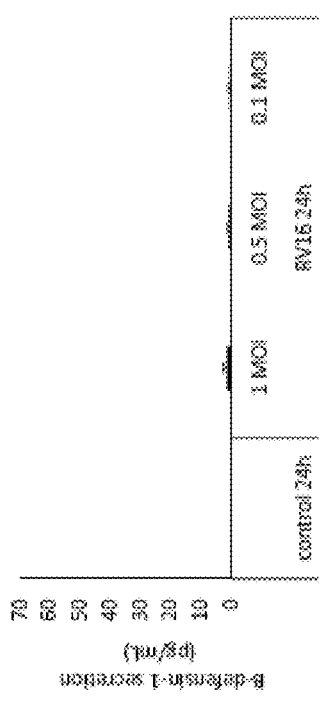
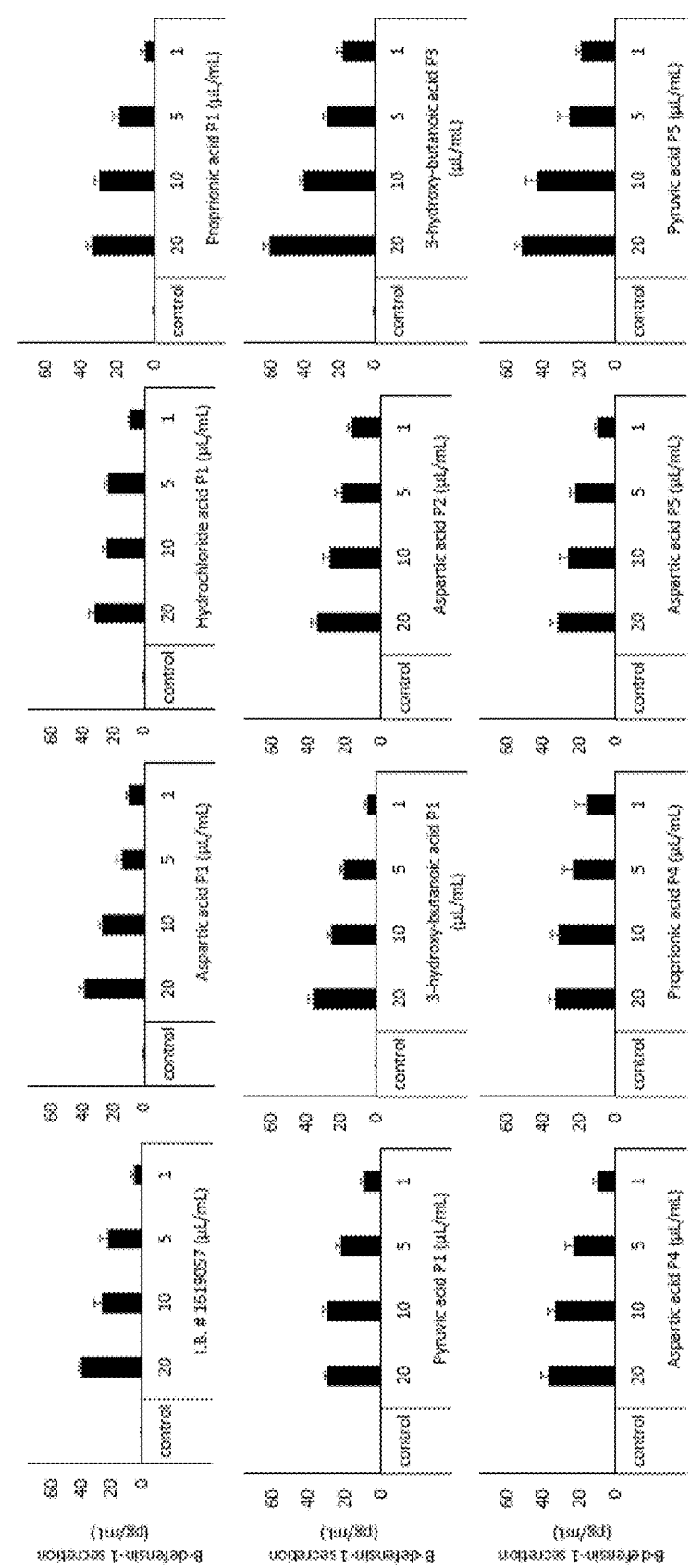

Figure 20
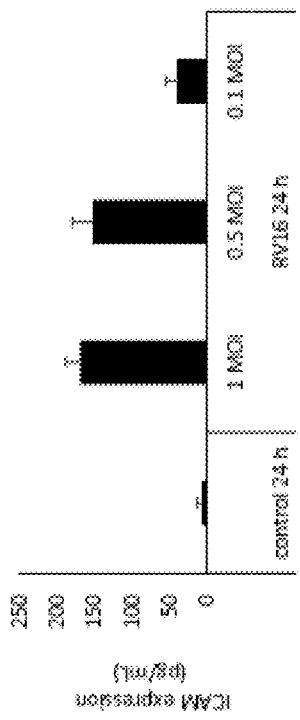
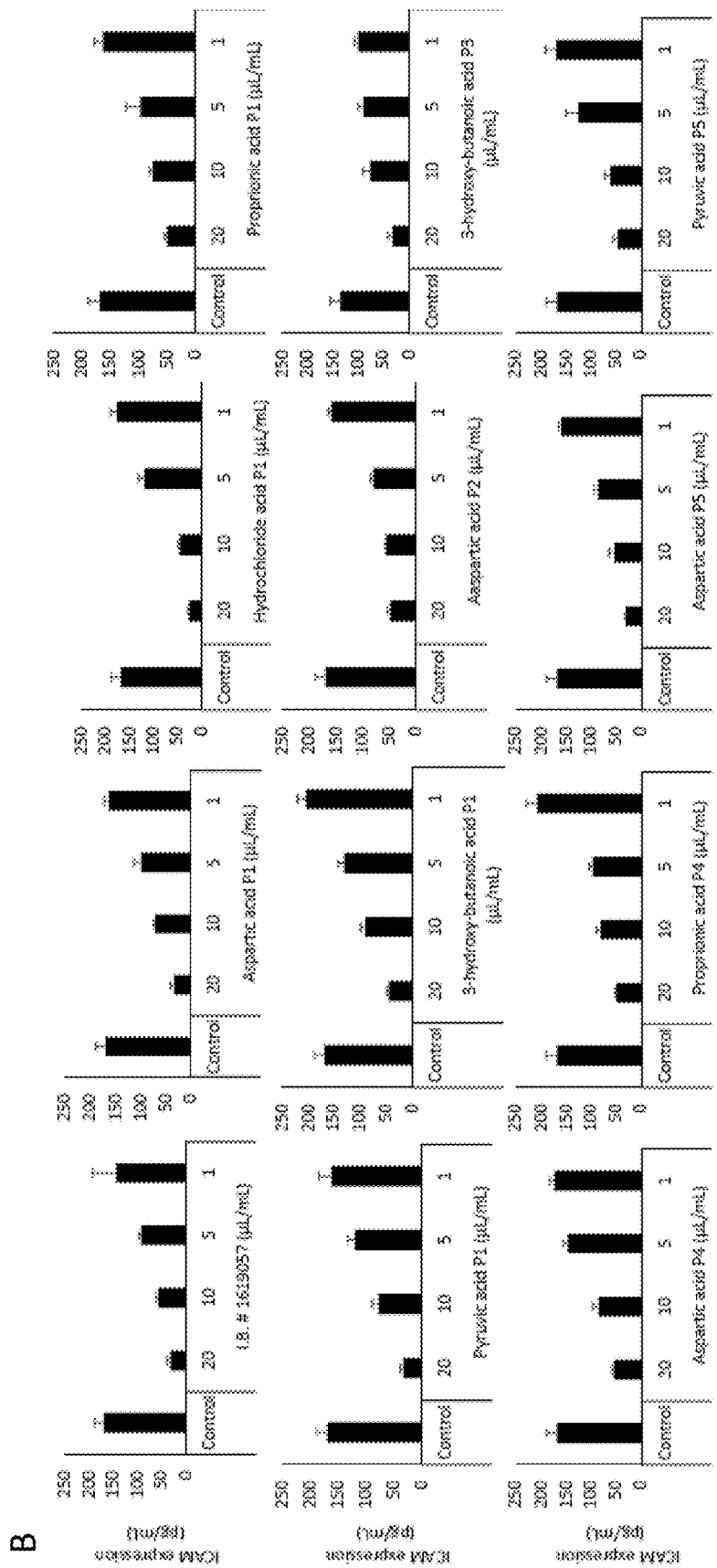

Figure 22

| NCD-Sham | NCD-BE | HFD-Sham | HFD-BE |
|---|---|---|---|
| Muribaculaceae | Lachnospiraceae NK4A136 group | Firmicutes | Ruminococcaceae |
| Bacteroidales | Uncultured bacterium | Clostridiales | Uncultured bacterium |
| Bacteroidia | Clostridiales vadinBB60 group | Clostridia | Ruminiclostridium |
| Bacteroidetes | Tenericutes | Blautia | Verrucomicrobiales |
| Uncultured bacteria | Mollicutes | | Verrucomicrobiae |
| Lachnospiraceae_bacterium COE1 | | | Akkermansia |
| | | | Verrucomicrobia |
| | | | Akkermansiaceae |
| | | | Peptococcaceae |
| | | | Ruminiclostridium |

STABLE BACTERIAL EXTRACTS AS PHARMACEUTICALS

CROSS-REFERENCE TO RELATED APPLICATIONS

This application is a continuation-in-part application of International Patent Application No. PCT/EP2020/056742, filed Mar. 12, 2020, which claims priority of EP Application No. 19162912.0, filed Mar. 14, 2019. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present invention relates to novel stable bacterial extract preparations having substantial increased stability over time, novel methods of preparation thereof, pharmaceutical formulations based on these novel stabilized bacterial extracts, as well as novel routes of administration and delivery devices for treating and/or preventing acute and chronic immunological disorders resulting from infections and/or inflammation.

BACKGROUND OF THE INVENTION

There is an ever increasing interest in the development of pharmaceutically formulations, either liquid or solid, stable over time, which can be administered to human subjects for treating infections and inflammations which can be easily adaptable to broader routes of administration, such as oral, intranasal, intratracheal, intrapulmonary, transmucosal, topical, buccal, etc. as well as to disease conditions and stages (acute stage, exacerbations, etc.) of the patients.

Bacterial infections are often implicated in many respiratory conditions and antibiotic treatments are common. The efficacy of antibiotics in treating such disease conditions and exacerbations has been debated. Their overuse has been associated with increased cost and the potential for increased microbial antibiotic resistance.

Bacterial extract lysate preparations, which contain antigens derived from several strains of bacteria, have been shown to increase resistance to infection by these organisms. The way in which these bacterial extract lysates may exert their effects could be multi-fold and is not yet fully understood. Numerous bacterial extracts have been used as immune stimulants and anti-tumor agents. By way of examples, we can cite Bacillus Calmette-Guerin (BCG), Polysaccharide, beta 1,3, glucan, the Maruyama vaccine, and extracts of *Bifidobacterium, L. lactis, L. fermentum, L. acidophilus* and, *S. lactis*. Such extracts are thought to stimulate the immune system in a number of ways. One important way is to stimulate lymphocytes, to grow and to produce cytokines. The ability to induce production of such cytokines has a very powerful effect on the immune system.

In particular, several bacterial extract preparations have been already successfully developed by the Applicant for the treatment and/or the prevention of upper tract respiratory disorders. To this regard, we can cite the drug Broncho-Vaxom® which is a bacterial lysate extract from several pathogens frequently responsible for respiratory tract infections, as described inter alia in U.S. Pat. No. 9,463,209B2.

Broncho-Vaxom® is an immunostimulant administered as a capsule, a sachet or drops via the enteral oral route for the prevention and prophylaxis of respiratory tract infections, recurrent respiratory tract infections, such as acute bronchitis, chronic bronchitis, asthma, chronic obstructive pulmonary disease, and emphysema. It has been shown to enhance the production of TNF-$\alpha$ and interferon-$\gamma$ from cultured human peripheral blood mononuclear cells, to lead to activation of alveolar macrophages, and to stimulate bacterial killing by polymorphonuclear leukocytes. Applicant also developed *Lactobacillus* bacteria extracts and showed that these bacterial lysate extracts were efficient when administered as a capsule via the enteral oral route for treating infections, allergies, autoimmune disorders and inflammations (See international publication WO2010/027344).

The constant exposure of the mucosal surfaces like airways and lungs to inhaled viruses, bacteria and toxins presents a challenge to the immune system. The situation becomes even worse when the host is exposed to viral infection and subsequently is superinfected by microbes leading to an increased mortality rate. Accordingly, bacterial secondary infections following viral infections with influenza (H1N1 and the like), human rhinovirus (HRV), rhinosyncitial virus (RV), coronavirus (CoV, SARS-CoV, MERS-Cov, COVID-19 and the like) are a pressing problem facing respiratory medicine.

Experimentally, numerous in vivo studies have demonstrated that the bacterial extract Broncho-Vaxom® administered by the enteral oral route provided a protection in respiratory tract infection models. Most studies used solid pharmaceutical form (lyophilizate) as well as liquid bacterial extract, however, with limited stability. An example of such in vivo mice model using the human dose (7 mg dry weight bacterial extract, 40 mg of lyophilizate) showed that it was able to enhance protection from secondary bacterial and/or viral infections following influenza infection (Pasquali et al, Frontiers in Medicine 2014, 1,41).

Additionally functional dysbiosis originating from "junk food" enriched in fat, sugars and proteins and leading to microbiota dysregulation (Clarence M. et al., Abstract, Mar. 30 9, 2018—St-John University, Queens) was normalized by supplementing Broncho-Vaxom® in mouse accompanied with decrease of associated sequelae and co-morbidities.

For several years, Broncho-Vaxom® has thus been administered via the enteral routes in solid form (capsules or sachets) in order to stimulate immune defenses and for the prevention of common respiratory tract disorders and associated exacerbations. Protective effects of these bacterial lysate extracts, which have been designed and engineered for oral administration, initiate an immune response in the intestine (gut-associated lymphoid tissue, GALT). These organs sense and send immune cells to the lung armed to prevent and cure lung infections from the airways. Accordingly, there is not direct exposure of bacterial lysate to the lung. On the contrary, by moving from the enteral oral route to alternative "perioral" routes of administration, such as intranasal, nasal, inhalation, nebulization and intratracheal routes, the anti-infective effect of stabilized bacterial lysates is assumed to take place directly on lung cells or on the nasal and surrounding mucosa, where infections take place. Other "perioral" routes favorable to reach mucosal tissue are sublingual and buccal where infections start frequently.

According to the present invention, novel bacterial lysate extract formulations were developed to these alternative perioral administration routes and thus to better fit with broader routes of possible infections and inflammations. The ability of the mucosa to distinguish between harmful and harmless antigens is important in defending against pathogens and in protecting against damage caused by the body's own inflammatory responses.

These bacterial lysate extracts have been however so far commonly administered via the enteral oral route in the solid forms: capsules or sachets. One of the major technical difficulties when moving to alternative routes of administration and/or to alternative pharmaceutical formulations is that these bacterial extracts present some physical instability, with particularly the apparition of sedimentation. Such physical instability of these bacterial extracts is a substantial problem during the manufacturing process, the preparation and the storage, and it is thus a limiting factor for the developments of alternative pharmaceutical forms and/or alternative administration routes such as intranasal, pulmonary, intratracheal, mucosal, transmucosal, topical, external skin topical, buccal, sublingual, oral, pulmonary, intrabronchial, or intrapulmonary. Significantly impact regulatory approval as such, a stable formulation suitable for these alternative routes and pharmaceutical forms is essential to a successful therapeutic bacterial lysate-based drug product.

Therefore, it was important to address any issues of aggregation and precipitation of these bacterial extracts and provide improved stabilized soluble bacterial extracts, in order to improve on the one hand the manufacturing process solutions, and on the other hand to enable broader routes of administration and alternative pharmaceutical forms.

Importantly, the novel stable bacterial extract formulations may now be administered at more precise dosages with specific delivery devices suitable for perioral or oral administrations, and in particular user-friendly delivery devices, such as aerosols, nasal sprays, nebulizers, pens, thereby increasing treatment adherence and patient convenience. Another substantial advantage is that the novel stable bacterial extract may be administered more easily in liquid forms, via the oral route, to patients who are not able to swallow a tablet or a capsule such as infants, young children, particularly between 3 months and 6 years old, as well as adults, for example, some elderly people, who have difficulties for swallowing. Alternative formulations of the bacterial extracts such as emulsions, microemulsions, dispersions, creams etc. . . . may be envisaged for topical or external skin topical types of routes of administration.

Finally, the novel stable bacterial extracts do not precipitate either at low temperatures as well as at room temperature. The bacterial extract pharmaceuticals may thus be kept and stored as such, in normal conditions by the patients or the pharmacies, and do not present any risks of clogging any of the drug delivery devices, thereby allowing administering precise exact doses of the bacterial extracts. Such stable bacterial extracts also provide a major advantage for pharma industries for storing the intermediate drug product either during the manufacturing process or during formulation of the final pharmaceutical drugs.

SUMMARY OF THE INVENTION

The present invention thus relates to bacterial extract formulations prepared from Gram-positive and/or Gram-negative bacterial species which have improved stability properties and are thus suitable for a diversity of pharmaceutical formulations and routes of administration. In particular, the novel stabilized bacterial extract pharmaceutical compositions may be formulated for nasal, intranasal, intratracheal, mucosal, transmucosal, topical, buccal, sublingual, oral, pulmonary, intrabronchial, and/or intrapulmonary administrations.

The present invention also relates to suitable dosage forms and delivery systems for delivering the novel stabilized bacterial extracts according to the invention.

The present invention further relates to the method of treating and/or preventing acute and chronic immunological disorders resulting from infections and/or inflammation and/or neoplasms and/or dysbiosis.

The present invention finally relates to a novel process for preparing the stable bacterial extracts under liquid, semisolid or aerosol forms either as final pharmaceutical drugs before administration to patients, or during manufacturing and/or formulations of the pharmaceutical drug products.

BRIEF DESCRIPTION OF THE FIGURES

FIG. 19: Shows anti-viral beta β-defensin-1 expression by human lung-derived primary epithelial cell (BECs). A) Shows the effect of infection (3 different concentrations) on β-defensin-1 secretion by BECs (n=3) over 24 hours following RV16 infection. (B) Shows the concentration-dependent effect of OM314A (P1, P2, P3), OM314B (P4) and OM-314C (P5) stable bacterial extract on the secretion of 0-defensin-1 by non-infected BECs (n=3). Bars represent mean±S.E.M of triplicates of each condition.

FIG. 20: ICAM-1 viral receptor expression. (A) Shows ICAM-1 receptor expression by human lung-derived primary epithelial cells (n=3) over 24 following RV16 infection. (B) Shows the concentration-dependent effect of OM314A (P1, P2, P3), OM314B (P4) and OM-314C (P5) stable bacterial extract on the expression of ICAM-1 by infected primary epithelial cells (n=3). Bars represent mean±S.E.M of triplicates of each condition.

FIG. 22: shows a linear Discriminant Analysis (LDA) scores in normal diet mice control fed with saline solution, normal chow diet (NCD (NCD-Sham), normal diet mice treated with bacterial extract from 21 strain lysates (NCD-BE), high fat diet mice control fed with saline solution (HFD-Sham) and high fat diet mice treated with bacterial extract from 21 strain lysates (HFD-BE).

DETAILED DESCRIPTION

Figure 1:
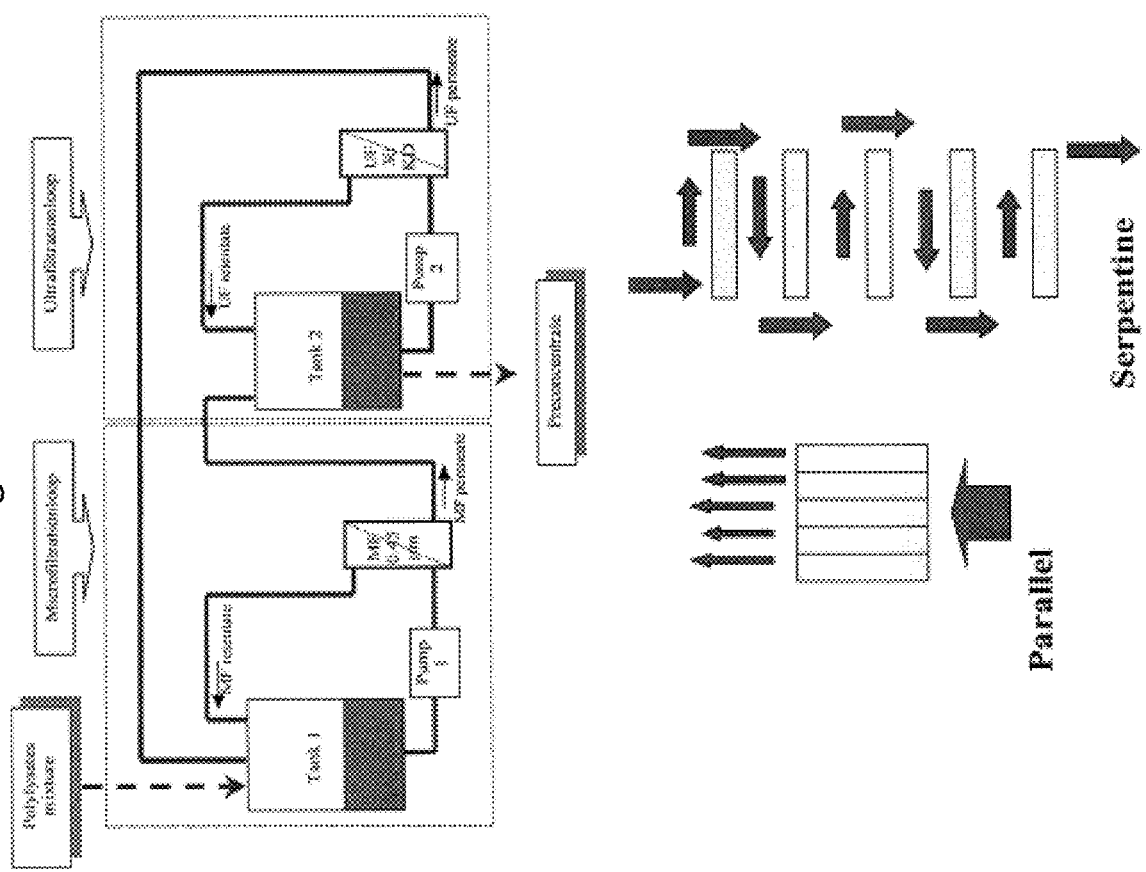
FIG. 1: is a diagram of a tangential flow filtration (TFF) system for preparation of bacterial extracts following alkaline lysis. The diagram shows two different configurations for filters: a parallel mode where all filters work simultaneously and a serpentine mode where filters are configured in a serial mode.

The present invention thus relates to a stable purified bacterial extract obtainable by alkaline lysis of Gram-positive and/or Gram-negative bacterial species and neutralization with one or more specific organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, or pharmaceutically acceptable salts and esters thereof, followed purification by filtration of the neutralized bacterial extract, and adjusting to a final physiological pH by adding the organic acid, combination or salts and esters thereof used for said neutralization.

Applicant has discovered that contacting the bacterial extract, after alkaline lysis whereby the pH of lysate is greater than 10 (with variations of 0.1 of the pH) with a selection of specific organic acid, led to a bacterial extract exhibiting surprisingly superior stability properties. More precisely, bacterial extract formulation according to the present invention retained physical stability for few months under liquid form.

Such novel bacterial extract formulations having improved physical stability could then be stably stored under liquid, semi-solid or aerosol forms, either as final pharmaceuticals for administration to patients or during the manufacture or the formulation of the pharmaceutical drug product.

"Stable" formulation is intended to mean a bacterial extract which essentially retains its physical stability in liquid form either during the storage of the pharmaceuticals or in liquid form as intermediate drug product during manufacturing or formulation. The bacterial extract formulation retains its physical stability in a pharmaceutical formulation if it shows no significant increase of aggregation and/or precipitation upon visual examination of the clarity, or as measured by light scattering, size exclusion chromatography (SEC) and dynamic light scattering. No significant precipitation or physical changes at room temperature is observed at 4° C., −20° C., or at −80° C. for at least 3 months, or 4 months, 5 months, 6 months, 7 months, 8 months, 9 months, 10 months, 11 months, or 12 months. Preferably, no more than 10%, preferably 5% of aggregation and precipitation is formed.

The terms "organic acid" refer to an organic compound that is characterized by weak acidic properties and does not dissociate completely in the presence of water.

The terms "alternative routes of administration route" generally refer to perioral and oral routes and may include inter alia intranasal, intratracheal, mucosal, transmucosal, topical, external skin topical, buccal, oral, sublingual, pulmonary, intrabronchial, and/or intrapulmonary routes of administrations.

The terms "OM314A bacterial extract" refer to a polyvalent immunomodulator comprising purified bacterial extract or lysate which is extracted by alkaline lysis from one or more of the most frequent bacterial pathogens of the upper respiratory tract, comprising *Moraxella catarrhalis, Haemophilus influenzae, Klebsiella pneumoniae, Staphylococcus aureus, Streptococcus pneumoniae, Streptococcus pyogenes*, and/or *Streptococcus sanguinis*. Preferably, the OM314A bacterial extract may be obtainable by alkaline lysis of the combination of one or more of the above bacterial pathogens, and most preferably it comprises the eight abovementioned pathogens. This OM314A bacterial extract has been prepared in a stable formulation according to the present invention and corresponds to the second generation of the bacterial extract previously described in several scientific publications and international publication WO2008/109669. The first generation of bacterial extract which is referred to herein below as "OM bacterial extract", is administered orally to the patients as solid swallowed formulations such as capsules and tablets, and has been showed to be efficient in preventing respiratory tract infections in adults and children. Furthermore, several clinical trials have been performed and demonstrated that the enteral administration (per oral) of this first-generation OM bacterial extract was showed to prevent allergic asthma and wheezing attacks provoked by acute respiratory tract illnesses in children when administered per oral. Said first generation of OM bacterial extract pharmaceuticals has been commercialized under the tradename of Broncho-Vaxom®, in solid form, generally a capsule or a sachet, which is administered to the patients per oral and at dose regimens of one capsule per day of 7 mg of lyophilized bacteria extract for adults treatment, and one capsule per day of 3.5 mg lyophilized bacteria extract for children.

Therefore, OM314A bacterial extract refers—as opposed to the first generation OM bacterial extract—to a second generation of drug comprising the OM bacterial extract, but which has been stabilized so that it can be formulated in any possible pharmaceutical forms, either liquid, gas or solid form, which are suitable for broader possible routes of administration including intranasal, intratracheal, mucosal, transmucosal, topical, buccal, oral, sublingual, pulmonary, intrabronchial, and/or intrapulmonary.

The terms "OM314B bacterial extract" refer to a polyvalent vaccine obtainable by alkaline lysis of one or more bacterial species chosen from *Lactobacillus* bacterial strains as described in international publication No. WO2010/027344. In particular, the stable bacterial extract may comprise one or more *Lactobacillus* bacterial strains chosen from *Lactobacillus fermentum, Lactobacillus rhamnosus, Lactobacillus plantarum, Lactobacillus johnsonii, Lactobacillus helveticus, Lactobacillus casei* defensis, *Lactobacillus casei* ssp. *casei*, 15 *Lactobacillus paracasei, Lactobacillus bulgaricus, Lactobacillus paracasei, Lactobacillus acidophilus, Lactobacillus reuteri, Lactobacillus salivarius, Lactobacillus lactis*, and/or *Lactobacillus delbrueckii*. The OM314B bacterial extract has been prepared in a stable formulation according to the present invention and corresponds to the second generation of the *Lactobacillus* bacterial extract previously described in international publication WO2010/027344. The OM314B bacterial extract has been stabilized so that it can formulated in any possible pharmaceutical forms, either liquid, gas or solid form, suitable for various possible routes of administration including intranasal, intratracheal, mucosal, transmucosal, topical, buccal, oral, sublingual, pulmonary, intrabronchial, and/or intrapulmonary routes.

Therefore, the terms "OM314C bacterial extract" refer to a stable bacterial extract obtainable by alkaline lysis of one or more *Escherichia coli* bacterial strains as described in the international publication No. WO2008/109667. The OM314C bacterial extract has been prepared in a stable formulation according to the present invention and corresponds to the second generation of the *Escherichia coli* bacterial extract previously described in international publication WO2008/109667. The second generation of OM314C bacterial extract has been stabilized so that it can formulated in any possible pharmaceutical forms, either liquid, gas or solid form, and thus suitable for a variety routes of administration including intranasal, intratracheal, mucosal, transmucosal, external skin topical, buccal, oral, sublingual, pulmonary, intrabronchial, and/or intrapulmonary.

The terms "stable bacterial extract formulation" refer to a stabilized form of the any bacterial extract drug obtainable by alkaline lysis extraction as described in international publications WO2008/109669, WO2010/027344, or WO2008/109667, but which have been adapted into pharmaceutical forms suitable for alternatives routes including intranasal, intratracheal, mucosal, transmucosal, topical, buccal, oral, sublingual, pulmonary, intrabronchial, and/or intrapulmonary as described above. Therefore, stable purified bacteria extracts according to the present invention may comprise bacteria alkaline lysate of any combinations of Gram positive and/or Gram negative bacterial species having therapeutic immunomodulating properties which have been stabilized and thus can be formulated in any pharmaceutical forms for a broad variety of routes of administration including intranasal, intratracheal, mucosal, transmucosal, topical, buccal, oral, sublingual, pulmonary, intrabronchial, and/or intrapulmonary as described above.

According to first embodiment, novel stable bacterial extract formulations may comprise bacterial lysate of one or more bacteria species chosen from *Moraxella catarrhalis, Haemophilus influenzae, Klebsiella pneumoniae, Staphylococcus aureus, Streptococcus pneumoniae, Streptococcus*

*pyogenes*, and/or *Streptococcus sanguinis*, as described in Applicant's international publication No. WO2008/109669. Preferably, the novel stable bacterial extract formulation according to this embodiment is designated herein below stable OM314A bacterial extract formulation and is obtainable by alkaline lysis of the following bacteria species *Moraxella catarrhalis, Haemophilus influenzae, Klebsiella pneumoniae, Staphylococcus aureus, Streptococcus pneumoniae, Streptococcus pyogenes*, and *Streptococcus sanguinis*.

According to this embodiment, it is thus provided a stable purified bacterial extract derived from one or more bacteria species chosen from *Moraxella catarrhalis, Haemophilus influenzae, Klebsiella pneumoniae, Staphylococcus aureus, Streptococcus pneumoniae, Streptococcus pyogenes*, and/or *Streptococcus sanguinis*, wherein said bacterial extract is obtainable by alkaline lysis of the bacterial strains and neutralization with one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, and/or pharmaceutically acceptable salts and esters thereof, followed by purification by filtration of the neutralized extract, and adjusting to a final physiological pH by adding the same organic acid or the same combination thereof used for said neutralization.

According to a second embodiment, the stable bacterial extract formulation is prepared from one or more bacterial species chosen from *Lactobacillus* bacterial strains. In particular, the stable bacterial extract may comprise one or more *Lactobacillus* bacterial strains chosen from *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis*, and/or *Lactobacillus delbrueckii*, as described in the Applicant's international publication No. WO2010/027344.

Therefore, according to this second embodiment, it is provided a stable purified bacterial extract derived from one or more *Lactobacillus* bacterial strains, wherein said bacterial extract is obtainable by alkaline lysis of the bacterial strains and neutralization with one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, and/or pharmaceutically acceptable salts and esters thereof, purification by filtration of the neutralized extract, and adjusting to a final physiological pH by adding the same organic acid or the same combination thereof used for said neutralization.

In a third embodiment, the stable bacterial extract derived from one or more *Escherichia coli* bacterial strains, wherein said bacterial extract is obtainable by alkaline lysis of said bacterial strains and neutralization with one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, and/or pharmaceutically acceptable salts and esters thereof, purification by filtration of the neutralized extract, and adjusting to a final physiological pH by adding the same organic acid or the same combination thereof used for said neutralization. In particular, *Escherichia coli* bacterial extract may comprise one or more *Escherichia coli* bacterial strains as described in the Applicant's international publication WO2008/109667.

According to this third embodiment, it is thus provided a stable purified bacterial extract from one or more *Escherichia coli* bacterial strains, wherein said bacterial extract is obtainable by alkaline lysis and neutralization with one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, or pharmaceutically acceptable salts and esters thereof, following by purification by filtration of the neutralized extract and adjusting to a final physiological pH by adding the same organic acid or the same combination thereof used for said neutralization.

In the above embodiments, the bacteria extracts comprise at least one strain from each of the above species of bacteria, while in other embodiments, one or more specific strains from the list above may be removed or substituted with one or more different strains.

As indicated above, it is not intended to limit the preparation of stable bacterial extract formulations to any of those specific embodiments as any other combinations of Gram+ and/or Gram− bacteria may be prepared and formulated according to the present invention and would also exhibit improved stability property.

Typically, the bacterial extracts are prepared by fermentation followed by heat inactivation and alkaline lysis and filtration. Fermentation, alkaline lysis and filtration are now well-known in the art and have been described inter alia in international publications WO2008/109667, WO2010/027344, and WO2008/109669.

Fermentation is generally performed by growing each bacteria strain to a suitable optical density in a culture medium. For each strain, to obtain a sufficient amount of material, the fermentation cultures may be started from a working seed lot followed by inoculation into larger fermentation containers. For example, fermentation may start with a small culture such as 0.1 to 1.0 liter, incubated for about 3 to 6 hours at 30 to 40° C., such as 37° C., to obtain an optical density (OD) at 700 nm of 3.0 to 5.0. After a small-scale culture step, additional cultures in one or a series of larger fermenters may be performed at 30° C. to 40° C. for a duration of 3 hours to 20 hours, such as for 3-10 hours, or 8 hours.

The culture medium is preferably a medium that does not pose a risk of prion-related diseases (i.e., mad cow disease, scrapie, and Creutzfeld-Jacob disease) or other diseases and thus that does not comprise animal-based materials such as serum or meat extracts taken from animals such as cows or sheep or from any other animal that can transmit prion-based diseases. For example, a non-animal medium, such as a vegetable-based medium, such as a soya-based medium, or a synthetic or hemi-synthetic medium, may be used. Alternatively, media using horse serum or media comprising materials taken from animal species that do not transmit prion diseases may be used. The culture medium may also include biological extracts such as yeast extract and horse serum, which also do not pose such disease risks. Supplementary growth factors may also be introduced to enhance the growth of some bacteria species.

After fermentation, the biomass from each bacteria strain or from combined bacteria strains is generally inactivated by a heat treatment, concentrated, and frozen.

Alkaline lysis is used for lysing bacterial cells under basic conditions and is generally performed by using an organic or inorganic base. Alkaline lysis may be performed on a single bacterial biomass or on mixture of bacterial biomass or fermentation batches, under basic conditions, typically with a concentrated solution of hydroxide ions, such as from NaOH.

Alkaline lysis may be performed preferably at a pH greater than around 10, with variations of 0.1 of the pH. Duration of the lysis may be assessed by the skilled person in the art and depends on the initial bacterial biomass amount. Lysis may be performed at temperatures ranging from 30 to 60° C., such as from 30-40° C., or from 35-40° C., such as 37° C. In general, lysis is stopped when bacteria cells appear to all have been disrupted based on a visual observation as this is well-known to the skilled person in the art. When using more than one strain of the same bacterial genus, the strains may be lysed together or separately. The strains may thus be mixed before or after lysis.

During lysis, bacteria cells are disrupted, and components thereof are degraded and chemically modified. In particular, racemization of amino acids creates D-amino acids from the naturally occurring L-amino acids found in natural proteins. D-amino acids can be beneficial in increasing bioavailability of the extracts, as proteins constituted principally or partially from D-amino acids are not efficiently digested in the mammalian gut. Thus, antigenic molecules in the extracts that are chemically modified during lysis to contain D-amino acids remain in the patient's body for a longer time, allowing potentially for a stronger immunostimulating action.

After lysis, according to the present invention, the bacterial lysate was neutralized, i.e., pH of the lysate would be adjusted to a final pH between 5 and 8, between 6 and 8, between 6.3 and 7.8, or between 6.5 and 7.8, by addition of one or more specific organic acid. Said one or more specific organic acid may be selected according to the invention among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, and/or pharmaceutically acceptable salts and esters thereof.

The lysates are then purified by centrifugation and/or filtration to remove large cellular debris or any components that are insufficiently degraded, any insoluble or particulate material so as to obtain a soluble bacterial extract. Purification including centrifugation and filtration are well-known in the art to remove particulate matter from the extracts. For example, lysates may be centrifuged at 9000 g, followed by one or more rounds of filtration. Typically, the filtration may comprise the passage of an extract or a mixture of extracts, through one or more filters such as microfilters (i.e., microfiltration) or ultrafilters (i.e., ultrafiltration) which may be repeated in several passes or cycles. For example, successive rounds of filtration on larger pore filters followed by microfiltration using a smaller pore filter may be performed, such as a 0.2-micron filter. Ultrafiltration may also be employed in order to help extract soluble materials from the extract, for example, recirculating the ultrafiltration permeate for further microfiltration.

Tangential flow filtration (TFF) method may be used to filter the extracts and to extract solubilized molecules from larger cellular debris. This is well-known in the art and described inter alia by Wayne P. Olson (Separations Technology, Pharmaceutical and Biotechnology Applications, Interpharm Press, Inc., Buffalo Grove, IL, U.S.A., pp. 126-135). An example of a filtration loop process is showed in FIG. 1 below. At the beginning of such a process, a diluted bacterial lysate may be stored in a first tank. A microfiltration (MF) loop may be started, and the product is pumped. The resulting MF retentate is recycled, while the MF permeate may be transferred to a second tank. After reaching a suitable degree of concentration, an ultrafiltration (UF) loop may be started. The UF permeate may be recirculated back to the first tank for continuous extraction of solubilized compounds from the lysate while the UF retentate may be stored in the second tank. During the continuous extraction, the volumes in tanks 1 and 2 maybe adjusted by regulation of flow rates of the microfiltration and ultrafiltration permeates. Several such extraction cycles may be performed, either with TFF or another filtration method. In embodiments that use TFF, at the end of the last cycle, the ultrafiltration loop may be shut down and the microfiltration loop may be run alone, and the MF permeate transferred to tank 2. The microfiltration loop may be fitted with filters of 1.2 microns to 0.1 microns, such as filters of 0.65 to 0.2 microns, or 0.45 microns. The crossflow may be between 1000 Liters/hours $m^2$ (LHM) and 3000 LHM, such as between 1500 and 2500 LHM, or 2000 LHM with a transmembrane pressure (TMP) of 0.6 to 2 bars, such as between 0.8 and 1.5 bars, or 1.0 bar. The ultrafiltration loop may be fitted with filters of from 10 KDa to 1000 KDa, such as from 10 KDa to 100 KDa, or from 10 KDa to 30 KDa, or from 30 KDa to 100 KDa, or from 30 kDa to 300 kDa, or from 100 kDa to 300 kDa, or from 30 kDa to 1000 kDa, or from 100 kDa to 1000 kDa, or form 300 kDa to 1000 kDa. The crossflow may be between 30 LHM and 1000 LHM, such as between 20 and 500 LHM with a TMP of 0.2 to 1.5 bars, such as between 0.4 and 1.2 bars, or 0.5 bar.

Between 5 and 20 diafiltration volumes may be used to extract solubilized compounds from bacterial cell walls. Diafiltration media could be water adjusted to pH values between 7 and 11. In some embodiments, between 8 and 15 volumes are used. Hence, for example, in some embodiments, between 5 and 15 cycles of filtration may be used, in some cases between 8 and 15 cycles, such as 8, 9, 10, 11, 12, 13, 14, or 15 cycles.

In addition of removing any insoluble particles, such filtration also aimed at removing any nucleic acids. As a consequence of the filtration, the amount of nucleic acid present in the bacterial extract may remain less than 100 microgram/mL. However, saccharide components, including monosaccharides, disaccharides, as well as larger saccharides such as linear and branched polysaccharides, and particularly the lipopolysaccharide (LPS) components, may be preserved by the filtration. Indeed, during the lysis process, saccharides (including LPS components) were cleaved in smaller structures or substituted by different functional groups. To this regard, while it was previously thought that saccharide components, including potentially toxic LPS components should be removed from bacterial extracts for safety reasons (See, U.S. Pat. No. 5,424,287), Applicant showed that saccharides components, including LPS, may be safely retained as these components in fact provide additional antigens to the extracts and thus improve the therapeutic efficacy. The extracts may be further diluted, concentrated or centrifuged, if desired.

After diafiltration, the alkaline purified soluble bacteria extract was further adjusted according to the present invention, by adding one or more specific organic acid in order to neutralize the lysate. Said organic acid may be selected according to the invention among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, and/or pharmaceutically acceptable salts and esters thereof. Preferably the final pH of the bacterial extract formulation may be adjusted between 5 and 8, between 6 and 8, between 6.3 and 7.8, or between 6.5 and 7.8.

Such purified soluble bacteria extracts may thus advantageously be conserved and stored as liquid according to the present invention and remained clear without any sedimentation or precipitation and thus retaining excellent physical stability. Alternatively, the purified bacteria extracts may be lyophilized if needed, prior to reformulating them under liquid, gas or solid forms for therapeutic uses or further galenic processes.

When the bacterial extract formulations are kept as liquid formulations, they may be stored at room temperature for a long period of time with excellent physical stability over time while still maintaining the biological activity. Advantageously, the bacterial extracts can be stored at room temperature, or at 4° C., −20° C., or at −80° C. without formation of aggregates and precipitates during the formulation process or storage. According to the present invention, it was thus possible to greatly reduce the formation of any aggregates, either insoluble or soluble in the bacteria extract formulations. Furthermore, not only improved physical stability has been observed, but the formulations also maintained the superior biological activity of the polysaccharides, the lipopolysaccharides, proteins, racemized amino acids and other biological components during the production or storage, without substantial chemical degradation or modification of the biological components.

Bacterial extract formulations according to the present invention could thus be stored RT, or at 4° C., −20° C., or at −80° C. for a period at least 1 month, or at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, said formulations show no substantial physical change brought about during manufacture and/or storage of the bacterial extract by the effect of, for example, light, temperature, pH, water or by reaction with an excipient and/or the immediate container closure system. Furthermore, same bacterial extract formulation of a known initial biological activity when placed under the same storage conditions could retain at least the initial biological activity. In a related embodiment, the bacterial extract has not reached its labelled expiration date during said storage period.

Compositions and chemical properties of the main components of the therapeutically active soluble bacterial extracts so obtained have been precisely determined and were maintained over time in liquid formulations. In particular, as indicated herein above, amount of nucleic acid present in the bacterial extract is less than 100 □g/mL. Also, the bacterial extracts comprise more than 0.1 mg/mL of polysaccharides, or between 0.1 to 4.5 mg/mL, or 0.1 to 4 mg/mL, or 0.1 to 4 mg/mL, or 0.1 to 3.5 mg/mL, or 0.6 to 3 mg/mL or 0.3 to 1 mg/mL or a range starting or ending from 0.1, 0.2, 0.3, 0.4, 0.5, 0.6, 0.7, 0.8, 0.9, 1.0, 1.5, 2.0, 2.5, 3.0, 3.5, 4.0, or 4.5 mg/mL of polysaccharides, such as, e.g. 0.4 to 0.5 mg/mL. Moreover, yields of solubilized proteins may be measured in the soluble purified bacterial extract by Lowry may be more than 50%, or may be more than 60%, or may be 50 to 90%, or may be 60-90%, for example. Therefore, the bacteria extract may comprise 5-75 mg/mL of proteins, or 10-65 mg/mL, or 20-45 mg/mL, or 5-40 mg/mL, or 5-20 mg/mL, or 5-10 mg/mL or 6-8 mg/mL of proteins or a range starting or ending from 5, 6, 8, 10, 15, 20, 25, 30, 35, 40, 45, 50, 55, 60, 65, 70 or 75 mg/mL; 1.5 to 2.5 mg/mL of free amino acids (A.A.), or 1.5 to 2 mg/mL, or 2 to 2.5 mg/mL of free A.A., or a range starting or ending from 1.5, 1.6, 1.7, 1.8, 1.9, 2.0, 2.1, 2.2, 2.3, 2.4, or 2.5 mg/mL of free A.A., calculated from glutamic acid (147.1 g/mol); and 0.3 to 4.5 mg/mL of polysaccharides and monosaccharides, or 0.3 to 4 mg/mL, or 0.4 to 4 mg/mL, or 0.5 to 3.5 mg/mL, or 0.6 to 3 mg/mL or 0.3 to 1 mg/mL or a range starting or ending from 0.3, 0.4, 0.5, 0.6, 0.7, 0.8, 0.9, 1.0, 1.5, 2.0, 2.5, 3.0, 3.5, 4.0, or 4.5 mg/mL of polysaccharides and monosaccharides, such as, e.g. 0.4 to 0.5 mg/mL.

In addition, such lysis results in partial hydrolysis of proteins as well as deamination, deamidation, and partial racemization of amino acids from L to D. Racemization of amino acids during the lysis process creates D-amino acids from the naturally occurring L-amino acids found in natural proteins. Analytical studies of the bacteria extracts have determined percentages of racemization. Peaks representing D-aspartic acid, D-glutamic acid, D-serine, D-methionine, D-histidine, D-alanine, D-arginine, D-phenylalanine, D-tyrosine, D-leucine, and D-lysine were observed. The percentage of D-amino acids of those species ranged from 3% to 40%. Hence, racemization of one or more of serine, threonine, histidine, alanine, arginine, tyrosine, phenylalanine, leucine, and/or lysine has been revealed. At least 10% of one or more of the above amino acids may become racemized from D to L. D-amino acids can be beneficial in increasing bioavailability of the extracts, as proteins constituted principally or partially from D-amino acids are not efficiently digested in the mammalian gut. Thus, antigenic molecules in the extracts that are chemically modified during lysis to contain D-amino acids remain in the patient's body for a longer time, allowing potentially for a stronger immunostimulating action.

Finally, lysis of bacteria according to the present invention may result in a diminution of the molecular weight of component molecules from 0 to 300 kDa to 0 to 100 kDa, or 0 to 60 kDa due to hydrolysis.

By way of example, the bacterial extract may thus contain about 6 to 8 mg/mL of proteins, 1.5 to 2.5 mg/mL of amino acids (A.A.) (measured after HCl hydrolysis) and/or about 0.4 to 0.5 mg/mL of polysaccharides and monosaccharides. Protein concentration is measured by the Lowry assay in accordance with method 2 of European Pharmacopoeia 2.5.33. The sugar concentration is assayed after acid hydrolysis and derivatization according to D. Herbert et al., *Meth. Microbiol.* 5B: 266 et seq. (1971).

The glutamate (glutamic acid) concentration is measured by converting amino acids to isoindole derivatives and measuring absorbance at 340 nm, according to Roth M., Fluorescence reaction for amino acids, *Anal. Chem.,* 43, 880-882, (1971).

As indicated above, it was experimentally demonstrated that the OM bacterial extract administered per oral in solid form at the human dose (7 mg dry weight bacterial extract) in mouse was able to enhance protection from secondary bacterial infection following influenza infection (Pasquali et al, Frontiers in Medicine 2014, 1, 41).

Routes of administration of the OM bacterial extract have always been per oral (e.g., enteral route) and dose regimen for adult treatment was one capsule per day of 7 mg of lyophilized bacteria extract, and one capsule per day of 3.5 mg lyophilized bacteria extract for children. Applicant has however discovered that administration of the OM bacterial extract via alternative perioral non-enteral routes of administration, such as intranasal, intratracheal, mucosal, transmucosal, topical, buccal, sublingual, pulmonary, intrabronchial, and/or intrapulmonary routes provided a strong immune response and more efficient to counter possible infections and/inflammations.

Importantly, the observed superior therapeutic effects of these novel perioral routes of administration allowed a substantial decrease in the dosage of the bacterial extract drug. Dose regimens could be divided by two, with daily perioral dose regimens for adult treatment of 3.5 mg of lyophilized bacteria extract, and of 1.75 mg lyophilized bacteria extract for children. It has been thus demonstrated by the Applicant these novel perioral routes of administration provided higher therapeutic efficacy at lower doses.

Furthermore, Applicant showed that these novel perioral routes of administration of the bacterial extract—either stabilized bacterial extract formulations as described herein above or not—elicited stronger immune response in the respiratory tract and the lungs, while also producing strong immune responses at distal sites, such as the intestine, etc. . . . .

In particular, perioral administrations of the bacterial extracts (either in stable formulation or not) allowed protection of the patients against acute and chronic immunological disorders resulting from infections and/or inflammation and/or neoplasms and/or dysbiosis. Perioral routes of administration are thus particularly useful and effective in methods of treating and/or preventing these pathologies and disorders, which generally worsen the medical conditions and increase the risk of developing chronic pathologies.

According to the present invention, infections may comprise upper and lower respiratory tract infections and/or associated sequelae comprising as allergic rhinitis, rhinitis, nasopharyngitis, sinusitis, pharyngitis, tonsillitis, laryngitis, tracheitis, laryngopharyngitis, influenza, respiratory syncytial virus, human rhinovirus (HRV), rhinosyncitial virus (RV), coronavirus (CoV, SARS-CoV, MERS-Cov, COVID-19 and the like), croup, pneumonia, Hypersensitivity Pneumonitis, bronchopneumonia, bronchitis, bronchiolitis, pneumonia, obstructive pulmonary disease with acute lower respiratory infection, obstructive pulmonary disease with acute upper respiratory infections, or diseases with epithelial cilia motion disorders and/or mucus clearance disorders. Infections may also comprise secondary infections, non-respiratory viral infections, non-respiratory bacterial infections, systemic infections such as sepsis, septic shock and viral-induced complications.

In particular, Applicant demonstrated in the Examples below that repeated treatment with the OM314A bacterial extract according to the present invention significantly decreased the expression of ACE2 gene expression, probably through increased cleavage of ADAM17 and TMPRSS2, in human bronchial epithelial cells (HBEC), thereby resulting in a substantial reduction of the COVID-19 susceptibility. In addition, Applicant demonstrated that mice pre-treated with OM314A bacterial extract according to the present invention showed (1) an increase of lung insterstitial macrophages, (2) a faster interferon response to coronavirus challenge, (3) an increased viral resolution, and (4) a reduced tissue damage.

According to the present invention, inflammations may comprise allergic/atopic respiratory and non-respiratory indications atopic dermatitis, acute and/or chronic associated dermatitis, anaphylaxis and food allergies. Said inflammations may also comprise skin disorders, inflamed skin, as eczema, rosacea, atopic dermatitis, psoriasis, including photodamage (such as sun-induced inflamed and reddened skin) skin atrophy, skin dyspigmentation (patches/spots), photodermatitis (erythema: inflammation and reddened skin), telangiectasia, couperose, or actinic keratosis, as well as inflammations comprising T helper 2 predominant autoimmune indications chosen among Grave's disease, Hashimoto disease, scleroderma, Ig 4 related diseases, or pemphigus, and inflammations comprising eosinophilic indications chosen among eosinophilic cystitis, eosinophilic esophagitis, eosinophilic fasciitis. eosinophilic gastroenteritis, hypereosinophilic syndrome, eosinophilic granulomatosis with polyangiitis, eosinophilic asthma, or eosinophilic pneumonia.

According to the present invention, dysbiosis related disorders may comprise asthma, diabetes, type 2 diabetes, autoimmune diseases, diseases associated with low fiber regimens, atopic dermatitis, acute and/or chronic associated dermatitis, psoriasis, inflammatory bowel diseases, colitis, ulcerative colitis, Crohn's disease, obesity, metabolic diseases or disorders, hepatic failures, NASH, NAFLD, hepatic fibrosis, kidney failures, diseases associated with low fiber regimens.

Finally, neoplasm may comprise neoplastic indications with immunological disorders such as mastocytosis, mast cell leukemia, T helper 2 biased and/or immune-suppressed tumors.

Therefore, according to a first aspect, the present invention relates to purified bacterial extract obtainable by alkaline lysis of one or more bacterial species chosen from *Moraxella catarrhalis, Haemophilus influenzae, Klebsiella pneumoniae, Staphylococcus aureus, Streptococcus pneumoniae, Streptococcus pyogenes*, and or *Streptococcus sanguinis*, wherein said bacterial extract comprises less than 100 microgram/ml nucleic acids, for use in a method of treating and/or preventing acute and chronic immunological disorders resulting from infections and/or inflammations and/or neoplasms and/or dysbiosis, in a subject, wherein said purified soluble bacterial extract is either in stable formulation or not, is administered to the subject by perioral routes, particularly via intratracheal inhalation, intranasal, mucosal, transmucosal, external skin topical, buccal, sublingual, pulmonary, intrabronchial, and/or intrapulmonary administrations, and at a dose regimen inferior to the dose used for enteral oral administrations.

The present invention also relates to purified bacterial extract obtainable by alkaline lysis of one or more bacterial species chosen from *Moraxella catarrhalis, Haemophilus influenzae, Klebsiella pneumoniae, Staphylococcus aureus, Streptococcus pneumoniae, Streptococcus pyogenes*, and or *Streptococcus sanguinis*, wherein said bacterial extract comprises less than 100 microgram/ml nucleic acids, for use in a method of treating and/or preventing infections chosen among upper and lower respiratory tract infections and/or associated sequelae comprising as allergic rhinitis, rhinitis, nasopharyngitis, sinusitis, pharyngitis, tonsillitis, laryngitis, tracheitis, laryngopharyngitis, influenza, respiratory syncytial virus, human rhinovirus (HRV), rhinosyncitial virus (RV), coronavirus (CoV, SARS-CoV, MERS-Cov, COVID-19 and the like), croup, pneumonia, Hypersensitivity Pneumonitis, bronchopneumonia, bronchitis, bronchiolitis, pneumonia, obstructive pulmonary disease with acute lower respiratory infection, obstructive pulmonary disease with acute upper respiratory infections, or diseases with epithelial cilia motion disorders and/or mucus clearance disorders, secondary infections, non-respiratory viral infections, non-respiratory bacterial infections, systemic infections such as sepsis, septic shock and viral-induced complications, in a subject, wherein said purified soluble bacterial extract is either in stable formulation or not, is administered to the subject by perioral routes, particularly via intratracheal inhalation, intranasal, mucosal, transmucosal, external skin topical, buccal, sublingual, pulmonary, intrabronchial, and/or intrapulmonary administrations.

As indicated earlier, Applicant demonstrated in the Examples below that repeated treatment with the bacterial extract according to the present invention significantly decreased the expression of ACE2 gene expression, probably through increased cleavage of ADAM17 and TMPRSS2, in human bronchial epithelial cells (HBEC), thereby resulting in a substantial reduction of the COVID-19 susceptibility. In addition, Applicant demonstrated that mice pre-treated with OM314A bacterial extract according to the present invention showed (1) an increase of lung insterstitial macrophages, (2) a faster interferon response to coronavirus challenge, (3) an increased viral resolution, and (4) a reduced tissue damage.

The present invention still also relates to purified bacterial extract obtainable by alkaline lysis of one or more bacterial species chosen from *Moraxella catarrhalis, Haemophilus influenzae, Klebsiella pneumoniae, Staphylococcus aureus, Streptococcus pneumoniae, Streptococcus pyogenes*, and or *Streptococcus sanguinis*, wherein said bacterial extract comprises less than 100 microgram/ml nucleic acids, for use in a method of treating and/or preventing inflammations chosen among allergic/atopic respiratory and non-respiratory indications atopic dermatitis, acute and/or chronic associated dermatitis, anaphylaxis and food allergies, skin disorders, inflamed skin, as eczema, rosacea, atopic dermatitis, psoriasis, including photodamage (such as sun-induced inflamed and reddened skin) skin atrophy, skin dyspigmentation (patches/spots), photodermatitis (erythema: inflammation and reddened skin), telangiectasia, couperose, or actinic keratosis, as well as inflammations chosen among T helper 2 predominant autoimmune indications chosen among Grave's disease, Hashimoto disease, scleroderma, Ig 4 related diseases, or pemphigus, and inflammations comprising eosinophilic indications chosen among eosinophilic cystitis, eosinophilic esophagitis, eosinophilic fasciitis. eosinophilic gastroenteritis, hypereosinophilic syndrome, eosinophilic granulomatosis with polyangiitis, eosinophilic asthma, or eosinophilic pneumonia in a subject, wherein said purified soluble bacterial extract is either in stable formulation or not, is administered to the subject by perioral routes, particularly via intratracheal inhalation, intranasal, mucosal, transmucosal, external skin topical, buccal, sublingual, pulmonary, intrabronchial, and/or intrapulmonary administrations.

The present invention further relates to purified bacterial extract obtainable by alkaline lysis of one or more bacterial species chosen from *Moraxella catarrhalis, Haemophilus influenzae, Klebsiella pneumoniae, Staphylococcus aureus, Streptococcus pneumoniae, Streptococcus pyogenes*, and or *Streptococcus sanguinis*, wherein said bacterial extract comprises less than 100 microgram/ml nucleic acids, for use in a method of treating and/or preventing dysbiosis related disorders chosen among asthma, diabetes, type 2 diabetes, autoimmune diseases, diseases associated with low fiber regimens, atopic dermatitis, acute and/or chronic associated dermatitis, psoriasis, inflammatory bowel diseases, colitis, ulcerative colitis, Crohn's disease, obesity, metabolic diseases or disorders, hepatic failures, NASH, NAFLD, hepatic fibrosis, kidney failures, or diseases associated with low fiber regimens, in a subject, wherein said purified soluble bacterial extract is either in stable formulation or not, is administered to the subject by perioral routes, particularly via intratracheal inhalation, intranasal, mucosal, transmucosal, external skin topical, buccal, sublingual, pulmonary, intrabronchial, and/or intrapulmonary administrations.

The present invention finally relates to purified bacterial extract obtainable by alkaline lysis of one or more bacterial species chosen from *Moraxella catarrhalis, Haemophilus influenzae, Klebsiella pneumoniae, Staphylococcus aureus, Streptococcus pneumoniae, Streptococcus pyogenes*, and/or *Streptococcus sanguinis*, wherein said bacterial extract comprises less than 100 microgram/ml nucleic acids, for use in a method of treating and/or preventing neoplasm chosen among neoplastic indications with immunological disorders such as mastocytosis, mast cell leukemia, T helper 2 biased and/or immune-suppressed tumors, in a subject, wherein said purified soluble bacterial extract is either in stable formulation or not, is administered to the subject by perioral routes, particularly via intratracheal inhalation, intranasal, mucosal, transmucosal, external skin topical, buccal, sublingual, pulmonary, intrabronchial, and/or intrapulmonary administrations.

According to this first aspect, the extracts comprise at least one strain from each of the above species of bacteria. Alternatively, one or more specific strains from the list above may be removed or substituted with one or more different strains. In the case of the preferred perioral OM bacterial extract, the extracts is obtained from eight bacterial pathogens of the upper respiratory tract, namely *Moraxella catarrhalis, Haemophilus influenzae, Klebsiella pneumoniae, Staphylococcus aureus, Streptococcus pneumoniae, Streptococcus pyogenes*, and *Streptococcus sanguinis*. Bacterial extract according to this aspect may also be the perioral OM314A bacterial extract, ie., OM bacterial extract in stabilized form administered via perioral routes.

OM bacterial extract is obtainable by alkaline lysis, preferably at a pH of greater than 10, from one or more bacterial species namely *Moraxella catarrhalis, Haemophilus influenzae, Klebsiella pneumoniae, Staphylococcus aureus, Streptococcus pneumoniae, Streptococcus pyogenes*, and *Streptococcus sanguinis* and subsequent purification so as to contain less than 100 microgram/ml nucleic acids, at least 0.3 mg/mL of saccharides, between 6 and 8 mg/mL of proteins having a molecular weight of less than 30 kDa, between 1.5 and 2.5 mg/mL of amino acids (measured after HCl hydrolysis) in equivalents of glutamic acid (147 g/mol), 1 to 80% of said amino acids being racemized from L to D, of said one or more racemized amino acids being chosen from aspartic acid, asparagine, glutamic acid, glutamine, serine, methionine, histidine, alanine, arginine, phenylalanine, tyrosine, leucine, lysine, valine, and threonine. Further disclosures on extract properties and their suitable methods of preparation have been provided herein below and are also provided in international publication WO2008/109669, the entire content of which are incorporated by reference herein.

According to this first aspect, the present invention thus also relates to a method of treating and/or preventing upper and lower respiratory tract infections, associated sequelae and/or secondary infections, dysbiosis and/or dysbiosis related disorders, wherein said the perioral OM bacterial extract either stabilized or not, is administered to the subject via intratracheal inhalation, intranasal, mucosal, transmucosal, topical, buccal, sublingual, pulmonary, intrabronchial, or intrapulmonary administration, and at a dose regimen of 0.005 mg to 1 mg per day, i.e., at lower dosages that of enteral oral administration, and was efficient in conferring optimal protection. Preferably, the bacterial extract according to this aspect is the OM bacterial extract or its stabilized form OM314A bacterial extract. Furthermore, according to this aspect, secondary infections treated and/or prevented may be non-respiratory viral infections.

Applicant clearly demonstrated in the following Examples that intranasal administration of the OM bacterial extract according to this first aspect substantially reduced viral titer in the lung tissue after influenza viral infection and reducing morbidity and mortality of superinfected animals when compared to that of the oral administration and at much lesser dosage. Indeed, intranasal or intratracheal administration thereof as prophylactic treatment was showed to be more efficacious than enteral route of administration. Intranasal administration constituted an effective prophylactic treatment against influenza in this mouse model and that this protective effect was showed to be dose dependent. Applicant further demonstrated that intratracheal or intranasal direct administration of the purified bacterial extract according to this first aspect up-regulated the large chain isoforms of these two glycosaminoglycans, thereby evidencing that this bacterial extract was involved in novel beneficial mechanisms, such as the reduction of inflammation and the increase antigen presentation.

According to this first aspect, the present invention thus relates to a method of treating and/or preventing acute and chronic immunological disorders resulting from infections and/or inflammation and/or neoplasms and/or dysbiosis, comprising administering via perioral route a therapeutically effective amount of OM bacterial extract, or of the stabilized form OM314A.

The present invention in particular relates to a method of treating and/or preventing infections chosen among upper and lower respiratory tract infections and/or associated sequelae comprising as allergic rhinitis, rhinitis, nasopharyngitis, sinusitis, pharyngitis, tonsillitis, laryngitis, tracheitis, laryngopharyngitis, influenza, respiratory syncytial virus, human rhinovirus (HRV), rhinosyncitial virus (RV), coronavirus (CoV, SARS-CoV, MERS-Cov, COVID-19), croup, pneumonia, Hypersensitivity Pneumonitis, bronchopneumonia, bronchitis, bronchiolitis, pneumonia, obstructive pulmonary disease with acute lower respiratory infection, obstructive pulmonary disease with acute upper respiratory infections, or diseases with epithelial cilia motion disorders and/or mucus clearance disorders, secondary infections, non-respiratory viral infections, non-respiratory bacterial infections, systemic infections such as sepsis, septic shock or viral-induced complications, comprising administering via perioral route a therapeutically effective amount of OM bacterial extract, or of the stabilized form OM314A.

The present invention also relates to a method of treating and/or preventing immunological disorders including but are not limited to imbalance between T helper 1, T helper 17 and T helper 2 immune response, imbalance of T reg, type 2 hypersensitivity, immuno-suppression, eosinophilia, allergy and atopy comprising administering via perioral route a therapeutically effective amount of OM bacterial extract, or of the stabilized form OM314A.

The present invention still also relates to a method of treating and/or preventing inflammations comprising allergic/atopic respiratory and non-respiratory indications atopic dermatitis, acute and/or chronic associated dermatitis, anaphylaxis and food allergies, skin disorders, inflamed skin, as eczema, rosacea, atopic dermatitis, psoriasis, including photodamage (such as sun-induced inflamed and reddened skin) skin atrophy, skin dyspigmentation (patches/spots), photodermatitis (erythema: inflammation and reddened skin), telangiectasia, couperose, actinic keratosis, or inflammations comprising T helper 2 predominant autoimmune indications chosen among Grave's disease, Hashimoto disease, scleroderma, Ig 4 related diseases, or pemphigus, or inflammations comprising eosinophilic indications chosen among eosinophilic cystitis, eosinophilic esophagitis, eosinophilic fasciitis. eosinophilic gastroenteritis, hypereosinophilic syndrome, eosinophilic granulomatosis with polyangiitis, eosinophilic asthma, or eosinophilic pneumonia comprising administering via perioral route a therapeutically effective amount of OM bacterial extract, or of the stabilized form OM314A.

The present invention further relates to a method of treating and/or preventing dysbiosis related disorders chosen among comprise asthma, diabetes, type 2 diabetes, autoimmune diseases, diseases associated with low fiber regimens, atopic dermatitis, acute and/or chronic associated dermatitis, psoriasis, inflammatory bowel diseases, colitis, ulcerative colitis, Crohn's disease, obesity, metabolic diseases or disorders, hepatic failures, NASH, NAFLD, hepatic fibrosis, kidney failures, or diseases associated with low fiber regimens comprising administering via perioral route a therapeutically effective amount of OM bacterial extract, or of the stabilized form OM314A.

The present invention still further relates to a method of treating and/or preventing immunological disorders including but are not limited to imbalance between T helper 1, T helper 17 and T helper 2 immune response, imbalance of T reg, type 2 hypersensitivity, immuno-suppression, eosinophilia, allergy or atopy, comprising administering via perioral route a therapeutically effective amount of OM bacterial extract, or of the stabilized form OM314A.

The present invention finally relates to a method of treating and/or preventing neoplasms chosen among neoplastic indications with immunological disorders such as mastocytosis, mast cell leukemia, T helper 2 biased and/or immune-suppressed tumors, comprising administering via perioral route a therapeutically effective amount of OM bacterial extract, or of the stabilized form OM314A.

According to a second aspect, the present invention also relates to a bacterial extract obtainable by alkaline lysis from one or more bacterial species chosen from *Lactobacillus* bacterial strains, for use in a method of treating and/or preventing acute and chronic immunological disorders resulting from infections and/or inflammation and/or neoplasms and/or dysbiosis as described above in a subject, wherein *Lactobacillus* bacterial extract is either in stable formulation or not, and wherein it is administered to the subject by perioral routes, particularly via intratracheal inhalation, intranasal, mucosal, transmucosal, external skin topical, buccal, sublingual, pulmonary, intrabronchial, and/or intrapulmonary administrations, and at a dose regimen inferior to the dose used for enteral oral administrations. The bacterial extract may preferably comprise one or more *Lactobacillus* bacterial strains chosen from comprise one or more of *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis,* and *Lactobacillus delbrueckii*. Preferably, the perioral bacterial extract according to this aspect is the bacterial extract obtainable by alkaline lysis from one or more bacterial species chosen from *Lactobacillus* bacterial strains as described above or its stabilized form, i.e., OM314B bacterial extract.

According to this second aspect, the present invention thus relates to a method of treating and/or preventing acute and chronic immunological disorders resulting from infections and/or inflammation and/or neoplasms and/or dysbiosis, comprising administering via perioral route a therapeutically effective amount of *Lactobacillus* bacterial extract.

The present invention thus in particular relates to a method of treating and/or preventing infections chosen among upper and lower respiratory tract infections and/or associated sequelae comprising as allergic rhinitis, rhinitis, nasopharyngitis, sinusitis, pharyngitis, tonsillitis, laryngitis, tracheitis, laryngopharyngitis, influenza, respiratory syncytial virus, human rhinovirus (HRV), rhinosyncitial virus (RV), coronavirus (CoV, SARS-CoV, MERS-Cov, COVID-19), croup, pneumonia, Hypersensitivity Pneumonitis, bronchopneumonia, bronchitis, bronchiolitis, pneumonia, obstructive pulmonary disease with acute lower respiratory infection, obstructive pulmonary disease with acute upper respiratory infections, or diseases with epithelial cilia motion disorders and/or mucus clearance disorders, secondary infections, non-respiratory viral infections, non-respiratory bacterial infections, systemic infections such as sepsis, septic shock or viral-induced complications, comprising administering via perioral route a therapeutically effective amount of *Lactobacillus* bacterial extract.

The present invention also relates to a method of treating and/or preventing immunological disorders including but are not limited to imbalance between T helper 1, T helper 17 and T helper 2 immune response, imbalance of T reg, type 2 hypersensitivity, immuno-suppression, eosinophilia, allergy and atopy comprising administering via perioral route a therapeutically effective amount of *Lactobacillus* bacterial extract.

The present invention still also relates to a method of treating and/or preventing inflammations chosen among allergic/atopic respiratory or non-respiratory indications, atopic dermatitis, acute and/or chronic associated dermatitis, anaphylaxis or food allergies, skin disorders, inflamed skin, as eczema, rosacea, atopic dermatitis, psoriasis, including photodamage (such as sun-induced inflamed and reddened skin) skin atrophy, skin dyspigmentation (patches/spots), photodermatitis (erythema: inflammation and reddened skin), telangiectasia, couperose, or actinic keratosis, or inflammations comprising T helper 2 predominant autoimmune indications chosen among Grave's disease, Hashimoto disease, scleroderma, Ig 4 related diseases, or pemphigus, or inflammations comprising eosinophilic indications chosen among eosinophilic cystitis, eosinophilic esophagitis, eosinophilic fasciitis. eosinophilic gastroenteritis, hypereosinophilic syndrome, eosinophilic granulomatosis with polyangiitis, eosinophilic asthma, or eosinophilic pneumonia, comprising administering via perioral route a therapeutically effective amount of *Lactobacillus* bacterial extract.

The present invention further relates to a method of treating and/or preventing dysbiosis related disorders chosen among comprise asthma, diabetes, type 2 diabetes, autoimmune diseases, diseases associated with low fiber regimens, atopic dermatitis, acute and/or chronic associated dermatitis, psoriasis, inflammatory bowel diseases, colitis, ulcerative colitis, Crohn's disease, obesity, metabolic diseases or disorders, hepatic failures, NASH, NAFLD, hepatic fibrosis, kidney failures, or diseases associated with low fiber regimens comprising administering via perioral route a therapeutically effective amount of *Lactobacillus* bacterial extract.

The present invention further relates to a method of treating and/or preventing neoplasms comprising neoplastic indications with immunological disorders such as mastocytosis, mast cell leukemia, T helper 2 biased and/or immune-suppressed tumors, comprising administering via perioral route a therapeutically effective amount of *Lactobacillus* bacterial extract.

Stable bacterial extracts obtainable by alkaline lysis from one or more bacterial species chosen from *Lactobacillus* bacterial strains are particularly useful for treating and/or preventing rhinitis and/or allergic rhinitis, which is trivially called common cold symptoms with stuffy nose or runny nose.

According to a preferred embodiment of the second aspect, the present invention thus relates to a method of treating and/or preventing acute and chronic immunological disorders resulting from infections and/or inflammation and/or neoplasms and/or dysbiosis as described above comprising administering via perioral route a therapeutically effective amount of a *Lactobacillus* bacterial extract obtainable by alkaline lysis from one or more bacterial species chosen from *Lactobacillus* bacterial strains. Preferred *Lactobacillus* bacterial extract comprises one or more bacterial strains chosen from comprise one or more of *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis,*and *Lactobacillus delbrueckii*. Most preferably, the *Lactobacillus* bacterial extract is a stabilized OM314B bacterial extract as described hereinabove.

Stable *Lactobacillus* bacterial extract according to this second aspect is thus administered via perioral routes, particularly via intratracheal inhalation or intranasal administrations, and at a dose regimen inferior to the dose used for enteral oral administrations.

Considering the direct and indirect antiviral, nonspecific activity of OM- and newly stable OM314A (P1, P2, P3), OM314B (P4) and OM-314C (P5) bacterial extracts on the surface of epithelial cells demonstrated in vivo with reduction of viral cell titers and the mounting of antiviral antibodies against, but not limited to, H1N1, RSV as well as in vitro efficacy against human RV (exemplified by induction of IFNs, β-defensins accompanied by a decrease of the viral receptor ICAM-1, thus confirming induction by OM- and newly stable OM314A (P1, P2, P3), OM314B (P4) and OM-314C (P5) of losing attachment (up to loss) of viral attachment to epithelial cells, it can be anticipated that such perioral routes of administration are particularly useful and effective in the methods of treating and/or preventing upper and lower respiratory tract infections such as rhinitis, allergic rhinitis, nasopharyngitis, sinusitis, pharyngitis, tonsillitis, laryngitis, tracheitis, laryngopharyngitis, influenza, respiratory syncytial virus, bacterial secondary infections following viral infections with influenza (H1N1 and the like), human rhinovirus (HRV), rhinosyncitial virus (RV), coronavirus (CoV, SARS-CoV, MERS-Cov, COVID-19 and the like), croup, pneumonia, bronchopneumonia, bronchitis, bronchiolitis, obstructive pulmonary disease with acute lower respiratory infection, obstructive pulmonary disease with acute upper respiratory infections, diseases with epithelial cilia motion disorders and/or mucus clearance disorders.

These purified bacterial extracts may be stabilized as described herein above, and thus administered as stable bacterial extract formulations either solid, semi-solid, liquid, or aerosol forms.

Pharmaceutical compositions comprising the stabilized bacterial extracts and a pharmaceutically acceptable excipient are also provided. These pharmaceutical compositions may be stabilized and stored in liquid formulations for few months and administered to the patients in liquid or vaporized forms. Alternatively, they may be lyophilized and/or stored before reformulating as liquid or aerosol pharmaceuticals.

Stable pharmaceutical compositions according to the present invention are particularly useful in a method of treatment and/or prevention of acute and chronic immunological disorders resulting from infections and/or inflammation and/or neoplasms and/or dysbiosis as described above.

Since these pharmaceutical compositions remained stable for several months in any forms, liquid, gas or aerosol, semi-solid, or solid, they may be formulated for administration via intranasal, intratracheal, mucosal, transmucosal, topical, buccal, sublingual, oral, pulmonary, intrabronchial, and/or intrapulmonary routes. Preferably, they may be administered to the subject by intratracheal inhalation or by intranasal transmucosal route.

Particularly preferred are pharmaceutical compositions wherein said composition is liquid or aerosol and is formulated in a spray, droplet, colloidal, mist, nebulae, or in atomized vapor. Also preferred pharmaceutical compositions may be liquid or semi-solid formulations such as emulsions, microemulsions, aqueous dispersions, oils, milks, balsams, foams, aqueous or oily lotions, aqueous or oily gels, creams, solutions, hydroalcoholic solutions, hydroglycolic solutions, hydrogels, serums, ointments, mousses, pastes, or transdermal patches. In certain other preferred embodiments, said composition is solid and is formulated in a powder, or a crushable tablet.

In the preparation of the liquid, semi-solid, solid, and spray medicines the aforementioned materials may appropriately be used with any additives such as vehicles, binding agents, perfumes, flavoring agents, sweeteners, colorants, antiseptics, antioxidants, stabilizing agents, and surfactants, if desired.

In a preferred embodiment, the bacterial extract pharmaceutical composition is administered via the intranasal route and the composition may be in a form chosen from an emulsion, suspension, colloidal form, mist, nebulae, atomized vapor or a spray, a nasal tampon, powder, ointment, cream, lotion, gel, paste, salve, solution, tincture, patch, or strip.

In another preferred embodiment, the bacterial extract pharmaceutical composition may be administered via the oral and present in the form of a single dose container or monodose container such as monodose plastic bottle similar to those plastic bottles of physiologic liquid used as drops for dry-eyes, or in the form of monodose ampoules. The oral bacterial extract liquid formulations according to this preferred embodiment, are thus a stable formulation and may be kept in said monodose containers as a neutralized (close to pH 7) liquid formulation for long periods of time.

To prepare the present pharmaceutical compositions, bacterial extracts may be mixed with a pharmaceutical acceptable carrier, adjuvant and/or excipient, according to conventional pharmaceutical compounding techniques. Pharmaceutically acceptable carriers encompass any of the standard pharmaceutical carriers, such as a phosphate buffered saline solution, water, and emulsions, such as an oil/water or water/oil emulsion, and various types of wetting agents. The bacterial extracts can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see Remington's Pharmaceutical Sciences, edited by E. W. Martin (Mack Publishing Company, 18th ed., 1990). The pharmaceutical compositions can also include stabilizers and preservatives.

In one of the preferred embodiments, the pharmaceutical composition may be formulated as a crushable tablet. The tablet can be administered whole or lightly crushed, such as with finger pressure, and sprinkled over an appropriate vehicle. The crushable tablet can be prepared using direct compression processes and excipients with care taken in the process to avoid damaging the coating of the individual subunits. Suitable excipients to prepare the crushable tablet include those typically used for chewable tablets including mono- and di-saccharides, sugar polyols, and the like, or a combination thereof.

Exemplary excipients include mannitol, sorbitol, xylitol, maltitol, lactose, sucrose, maltose or a combination thereof. Optional pharmaceutical excipients such as diluents, lubricants, glidants, flavorants, colorants, etc. . . . or a combination comprising at least one of the foregoing may also be included in the compression matrix. The crushable tablets can be prepared using methods of tablet manufacturing known in the pharmaceutical art.

The bacterial extract formulation may also be present in as colloidal form, comprising for example, a metal halide, most preferably silver halide. The one or more bacterial extracts and adjuvant may be incorporated within or encapsulated by the colloidal particle. Alternatively, or in addition, one or more bacterial extracts and adjuvant may be attached to a surface of the colloidal particle. Means by which the active agent and adjuvant attach to the particle is dependent upon the characteristics of the extracts, adjuvants and the colloidal particles. For example, proteins readily adsorb or attach to hydrophobic particles via hydrophobic interactions with the particle surface and displace some of the neutral emulsifier.

The present invention is based in part, on the surprising discovery that the use of a perioral delivery system of the above described bacterial extracts provides for significantly higher antibody titers and enhanced immune response, and a safe and effective approach for enhancing the immunogenicity of a variety of antigens for use in both prophylactic and therapeutic pharmaceutical compositions.

Suitable dosages according to the invention and as described herein in the various embodiments will vary depending upon the condition, age and species of the subject and can be readily determined by those skilled in the art. However, according to the present invention, total daily dosages are greatly reduced and may be in the range of 0.005 to 1 mg, preferably from 0.05 to 0.5 mg, most preferably from 0.1 to 0.3 mg and these may be administered as single or divided doses, and in addition, the upper limit can also be exceeded when this is found to be indicated. Advantageously, the doses administered via perioral routes are inferior (e.g., half doses) to the doses administered via oral enteral routes.

Another aspect relates to a delivery device of the bacterial extract formulations according to the invention. Also provided is a delivery device for use in a method of treatment and/or prevention of upper and lower respiratory tract infections, associated sequelae and/or secondary infections, dysbiosis and/or dysbiosis related disorders.

According to the present invention, the bacterial extract formulations may be administered via intranasal or intratracheal route, by nasal insufflator device, intranasal inhaler, intranasal spray device, atomizer, nasal spray bottle, unit dose container, pump, dropper, squeeze bottle, nebulizer, metered dose inhaler (MDI), pressurized dose inhalers, insufflators, bi-directional devices, dose ampoules, nasal pads, nasal sponges, and nasal capsules.

Nasal sprays may be liquid or solid nasal sprays. The bacterial extract formulations may be administered as aerosols or in non-aerosol forms. The nasal delivery device can be metered to administer an accurate effective dosage amount to the nasal cavity. The nasal delivery device can be for single unit delivery or multiple unit delivery.

When the bacterial extract formulations are administered as aerosols, they may be prepared using standard procedures. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. The aerosol may be a suspension or dispersion of either liquid droplets or solid powder in air (or in a gas). Liquid droplets may be formed from solutions, suspensions and dispersions of drug in a liquid, such as water or a non-aqueous solvent. Aerosols may be produced in any suitable device, such as an MDI, a nebulizer, or a mist sprayer.

An aerosol according to the invention may be insufflated or inhaled using a suitable mechanical apparatus. The apparatus may include for example a reservoir and sprayer, which is a device adapted to expel the pharmaceutical dose in the form of a spray. A number of doses to be administered may be contained within the reservoir, optionally in a liquid solution or suspension or in a solid particulate formulation, such as a solid particulate mixture.

Nebulizer devices produce a stream of high velocity air that causes a therapeutic agent in the form of liquid to spray as a mist. The therapeutic agent is formulated in a liquid form such as a solution or a liquid suspension of particles of suitable size. The particles are micronized. The term "micronized" is defined as having about 90% or more of the particles with a diameter of less than about 10 m. Suitable nebulizer devices are provided commercially, for example, by PARI GmbH (Sternberg, Germany). Other nebulizer devices include Respimat (Boehringer Ingelheim) andthose disclosed in, for example, U.S. Pat. Nos. 7,568,480 and 6,123,068, and WO 97/12687.

DPI devices may be used to administer the bacterial extract formulation in the form of a free-flowing powder that can be dispersed in a patient's air-stream during inspiration. DPI devices having an external energy source may also be used. In order to achieve a free-flowing powder, the bacterial extract formulation may be combined with a suitable excipient (e.g., lactose). A dry powder combination can be made, for example, by combining dry lactose having a particle size between about 1 m and 100 m with micronized particles of the benzodiazepine and dry blending. Alternatively, the benzodiazepine can be formulated without excipients. The formulation is loaded into a dry powder dispenser, or into inhalation cartridges or capsules for use with a dry powder delivery device. Examples of DPI devices provided commercially include Diskhaler (GlaxoSmith line, Research Triangle Park, N.C.) (U.S. Pat. No. 5,035,237); Diskus (GlaxoSmithKline) (U.S. Pat. No. 6,378,519; Turbuhaler (AstraZeneca, Wilmington, Del.) (U.S. Pat. No. 4,524,769); and Rotahaler (GlaxoSmithKline) (U.S. Pat. No. 4,353,365).

MDI devices may be used to discharge a measured amount of the bacterial extract formulation using compressed propellant gas. Formulations for MDI administration include a solution or suspension of bacterial extract formulation in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. The bacterial extract formulation is loaded into an aerosol canister, which forms a portion of an MDI device.

The bacterial extract formulation may be delivered to the nasal cavity as a powder such as microspheres via a nasal insufflator. The bacterial extract formulation may be absorbed to a solid surface, for example, a carrier. The powder or microspheres may be administered in a dry, air-dispensable form. The powder or microspheres may be stored in a container of the insufflator. Alternatively, the powder or microspheres may be filled into a capsule, such as a gelatin capsule, or other single dose unit adapted for nasal administration.

The bacterial extract formulation is delivered through a nasal spray applicator. The composition may be placed in an intranasal spray-dosing device or atomizer and may be applied by spraying it into the nostrils of a subject for delivery to the mucous membrane of the nostrils. A sufficient amount is applied to achieve the desired systemic or localized levels for therapeutic effect.

The bacterial extract formulation may further be administered via intratracheal route, by oral inhalation into the respiratory tract, i.e., the lungs. Such intratracheal requires aerosolization of a solid or liquid and delivery of the aerosol to the lungs via the mouth and throat. Particles of medicament may be administered to the lungs as dry powder aerosols or liquid aerosols. Dry powder aerosols are generally administered to the lungs with dry powder inhaler (DPI) inhalation devices. Dry powder inhalers can include breath actuated dry powder inhalers, such as are described in U.S. Pat. No. 7,434,579. Metered-dose inhalers contain medicament suspended in a propellant, a mixture of propellants, or a mixture of solvents, propellants, and/or other excipients in compact pressurized aerosol dispensers. An MDI product may discharge up to several hundred metered doses of medicament. Each actuation may contain from a few micrograms (mcg) up to milligrams (mg) of the active ingredients delivered in a volume typically between 25 and 100 microliters.

As described above, another type of liquid aerosol dispersion device is nebulizer, which uses a jet, a vibrating mesh or other means to aerosolize a suspension containing particles of medicament.

The bacterial extract formulations according to the present invention may further comprise adjuvants, permeation enhancers and/or solvents. For example, for intranasal delivery, the permeation enhancer may be used to enhance the permeation of composition through the nasal mucosa. Compounds containing one or more than one hydroxyl group may be used as permeation enhancers. Some of these hydroxyl group-containing compounds can also serve as solvents in the composition. Non-limiting examples of hydroxyl group-containing compounds that may be used as permeation enhancers include alcohols (such as ethanol), diols (such as propylene glycol also known as 1,2-propanediol; 1,3-propanediol; butylene glycol including 1,3-butanediol, 1,2-butanediol, 2,3-butanediol, and 1,4 butanediol; hexylene glycol; dipropylene glycol; 1,5-pentanediol; 1,2-pentanediol; 1,8-octanediol; etohexadiol; p-menthane-3,8 diol; 2-methyl-2,4-pentanediol); triols (such as glycerin), polyols (such as suitable polymers containing multiple hydroxyl groups, including polyethylene glycols or PEGs, polypropylene glycols, polysorbates, and sorbitan esters; and suitable sugar alcohols), cyclitols (such as pinitol, insoitol), cyclic diols (such as cyclohexane diol), aromatic diols (such as hydroquinone, bisphenol A, resorcinol and catechol).

One of ordinary skill in the art would recognize that the instant teachings would also be applicable to other permeation enhancers. Non-limiting examples of other permeation enhancers useful in the instant invention are the simple long chain esters that are Generally Recognized As Safe (GRAS) in the various pharmacopoeia compendia. These may include simple aliphatic, unsaturated or saturated esters. Non-limiting examples of such esters include isopropyl myristate, myristyl myristate, octyl palmitate, and the like. Non-limiting examples other permeation enhancers include alcohols (e.g., short- and long-chain alcohols), polyalcohols, amines and amides, urea, amino acids and their esters, amides, pyrrolidone and its derivatives, terpenes, fatty acids and their esters, macrocyclic compounds, sulfoxides, tensides, benzyldimethylammonium chloride, cetyl trimethyl ammonium bromide, cineole, cocamidopropyl betaine, cocamidopropyl hydroxysultaine, dodecyl pyridinium chloride, dodecylamine, hexadecyl trimethylammoniopropane sulfonate, limonene, linoleic acid (OA), linolenic acid (LA), menthol, methyl laurate, methylpyrolidone, N-decyl-2-pyrrolidone, NLS, nicotine sulfate, nonyl-1,3-dioxolane, octyl trimethylammonium bromide, oleyl betaine, PP, polyethyleneglycol dodecyl ether, polyoxyethelene sorbitan monolaurate (Tween 20, or Polysorbate 20), SLA, sodium oleate, sodium lauryl sulfate, sodium octyl sulfate (SOS), sorbitan monolaurate (S20), tetracaine, and Triton X-100. The enhancers should be suitable. The skilled person in the will also appreciate that those materials that are incompatible with or irritating to mucous membranes should be avoided.

Examples of pharmaceutically acceptable solvents or excipients that may be used in the present composition may be found in reference books such as the Handbook of Pharmaceutical Excipients (Fifth Edition, Pharmaceutical Press, London and American Pharmacists Association, Washington, 2006). Non-limiting examples of pharmaceutically-acceptable solvents that may be used in the present composition include, but are not limited to, propylene glycol (also known as 1,2-dihydroxypropane, 2-hydroxypropanol, methyl ethylene glycol, methyl glycol or propane-1,2-diol), ethanol, methanol, propanol, isopropanol, butanol, glycerol, polyethylene glycol (PEG), glycol, Cremophor EL or any forms of polyethoxylated castor oil, dipropylene glycol, dimethyl isosorbide, propylene carbonate, N-methylpyrrolidone, glycofurol, tetraethyleneglycol, propylene glycol fatty acid esters, and mixtures thereof.

Particularly preferred are bacterial extract formulations or pharmaceutical compositions comprising said formulations for use in a method of treatment and/or prevention of upper and lower respiratory tract infections, associated sequelae and/or secondary infections, dysbiosis and/or dysbiosis related disorders, which are administered to the subject by intratracheal inhalation or by intranasal transmucosal route.

It is likely that intranasal administered bacteria extract effected the nasal-associated lymphoid tissue (NALT) or gut-associated lymphoid tissue (GALT), followed by trafficking of intestinally derived B- and T-cells and macrophages to bronchus-associated lymphoid tissue, and this may lead to an immune response against these pathogens in the respiratory tract.

The present invention also relates to a method for treatment, prevention, or attenuation of viral infections and/or virus-induced exacerbations of allergic diseases or disorders such as asthma, chronic obstructive pulmonary disease and allergy or autoimmunity comprising administering to a subject via perioral route a therapeutically efficient amount of the stable bacterial extract of the present invention.

Asthma condition may be steroid resistant asthma, neutrophilic asthma or non-allergic asthma. The allergic disease or disorder may be an eosinophilic disease or disorder, particularly a disease or disorder selected from the group consisting of nodules, eosinophilia, eosinophilic rheumatism, dermatitis and swelling (NERDS).

The present the invention relates to a method of treatment and/or prevention of an allergic disease or disorder, or for amelioration of the condition of a subject suffering from an allergic disease or disorder, including, but without being limited to, an allergic disease or disorder selected from the group consisting of asthma, rhinitis, dermatitis, drug reactions, eosinophilic diseases or disorders, esophageal and gastrointestinal allergy, comprising administering to a subject via perioral route a therapeutically efficient amount of the stable bacterial extract of the present invention.

The present invention finally provides a novel extraction process for preparation of bacterial extracts with enhanced stability. The process for preparing the bacterial extract with improved stability comprises the following steps of:
  a. culturing each bacterial strain species in a suitable culture medium,
  b. lysing each strain at an initial pH, preferably greater than 10, with variations of 0.1 ofthe pH,
  c. decreasing the pH of the extract(s) obtained in step (b) by 1 or 2 units by adding one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, or pharmaceutically acceptable salts and esters thereof,
  d. passing the product of step (c) at least once through a microfilter and retaining the product on an ultrafilter so as to obtain a purified soluble extract,
  e. adjusting to a final pH around 7 (+/−1.0) by adding the organic acid or the combination thereof used in step (b), and
  f. adding a pharmaceutically acceptable excipient or vehicle.

According to a first aspect of the present invention, the bacterial extract is obtained from one or more bacterial species chosen from: *Moraxella catarrhalis, Haemophilus influenzae, Klebsiella pneumoniae, Staphylococcus aureus, Streptococcus pneumoniae, Streptococcus pyogenes*, and/or *Streptococcus sanguinis*. Preferably, bacterial extract according to this aspect is derived from the eight bacterial pathogens of the upper respiratory tract, namely *Moraxella catarrhalis, Haemophilus influenzae, Klebsiella pneumoniae, Staphylococcus aureus, Streptococcus pneumoniae, Streptococcus pyogenes*, and *Streptococcus sanguinis* similarly to the first generation of OM bacterial extract drug.

According to a second aspect of the present invention, the bacterial extract is obtained from one or more bacterial species chosen from *Lactobacillus* bacterial strains, such as for example, *Lactobacillus fermentum, Lactobacillus rham-*

*nosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis,* and *Lactobacillus delbrueckii.*

According to a third aspect of the present invention, the bacterial extract is obtained from one or more *Escherichia coli* bacterial strains as described in the international publication No. WO2008/109667.

The lysis may be carried out for a period of 40 hours to 10 days at a temperature of to 60° C. Also, the microfilter may be used in the process is 0.45 microns and the ultrafilter is 30 KDa. Furthermore, part (c) of the process comprises tangential flow filtration, wherein the tangential flow filtration may be carried out for 5 to 15 cycles.

Furthermore, the present invention relates to bacterial extract formulation products and/or pharmaceutical compositions obtainable by said above process.

EXAMPLES

Example 1: Process to Stabilize Alkaline Extract

Example 1.1: Addition of Organic Acids for the Preparation of Stable Bacterial Extracts (OM314A)

Preliminary measurements of the quantities of acid required to acidify to pH 5.0 the alkaline OM314A bacterial extract and of NaOH 1N to adjust at pH 7.0 were first performed.

25 mL of OM314A alkaline concentrate was introduced in Falcon tubes of 50 mL. The native pH as measured is generally around pH 10.5. After measurement of the native pH, a small magnetic stirrer was introduced in the tube and stirring at 600 rpm is started. The required quantity of each selected organic acid is introduced stepwise in small amounts until pH 5.0 (5.0±0.2) is reached. The volume and weight of each selected organic acid are recorded. The acidic extract is then centrifuged 5 min at 5000 g and the supernatant filtered through a 0.2 μm filter. The pH of the stabilized bacterial extract is than adjusted to pH 7.0±0.2 using NaOH 1N and the volume of NaOH 1N used is recorded.

In a second series of preparations, 35 mL of OM314A alkaline concentrate was adjusted from pH 10.5 to pH 5.0 (5.0±0.2) with the required quantity of each selected organic acid added stepwise in small amounts until pH 5.0 (5.0±0.2) is reached. The volume and weight of acid are recorded. The acidic extract is then centrifuged 5 min at 5000 g and the supernatant filtered 0.2 μm filter. The pH of the stabilized bacterial extract is than adjusted to pH 7.5±0.2 using NaOH 1N and the volume of NaOH 1N used is recorded. A similar procedure is performed in a sterile laminar flow cabinet to prepare sterile samples of the stabilized bacterial extract.

25 mL or 35 mL of alkaline OM314A bacterial extract concentrate were introduced in Falcon tubes of 50 ml. Each acid was added based on a predetermined volume or by weighing as determined in the preliminary measurements. Acidification was done initially to pH 5.0 but a precipitate was formed. In a second step pH was adjusted to 7.0±0.2 and respectively 7.5±0.2. Some solutions adjusted to pH 5 with the organic acids and further adjusted to pH 7.0 and respectively 7.5 remained clear and stable all over the observation period at room temperature but not at 4 to 8° C. where a precipitate formed after several weeks of storage.

The following Table 1 recapitulates the organic acids and volumes used to adjust pH to 7.5 for a 35 mL solution of OM314A bacterial extract.

TABLE 1

| Acid | Liquid [% purity] Solid [% purity] | Volume/ weight added to adjust pH to 7.5 | turbidity | Stability at 20° C. to 25° C. | Stability at 4° C. to 8° C. |
| --- | --- | --- | --- | --- | --- |
| HCl (acid control) | Liquid, 25% | 120 μl | high | Not stable, precipitate | Not stable, precipitate |
| Formic acid | Liquid, 98-100% | 30 μl | slightly turbid | Not stable, precipitate | Not stable, precipitate |
| Propanoic acid | Liquid, 99% | 70 μl | slightly turbid | Relatively stable, Very low amounts of precipitate | Relatively stable, Very low amounts of precipitate |
| Aspartic acid | Solid > 98% | 118 mg | clear solution | Relatively stable, Very low amounts of precipitate | Relatively stable, Very low amounts of precipitate |
| Lactic acid | Liquid, 90% | 120 μl | slightly turbid | Relatively stable, Very low amounts of precipitate | Relatively stable, Very low amounts of precipitate |
| 3-hydroxy-propanoic acid | Liquid, 30% as water solution | 250 μl | slightly turbid | Relatively stable, Very low amounts of precipitate | Relatively stable, Very low amounts of precipitate |
| Butanoic acid | Liquid, 99% | 70 μl | slightly turbid | Relatively stable, Very low amounts of precipitate | Relatively stable, Very low amounts of precipitate |
| Glutamic acid | Solid | 150 mg | slightly turbid | Relatively stable, Small amount of precipitate | Relatively stable, Small amount of precipitate |

Example 1.2. Removal of Inorganic Cations

In order to remove inorganic divalent cations present in the organic acid stabilized OM314A extract as described previously in example 7.1, 25 mg of ammonium oxalate (1 mg/mL) were added. A precipitate is formed with strong opalescence. The precipitate is centrifuged 5 min at 5000 g and the clear supernatant is filtered on a 0.2 μm filter. The clear sample is adjusted to pH 7.0±0.1 using NaOH 1N. The difficulty of the process is the scaling-up which would require a centrifugation. Furthermore, oxalate may not be suitable for intranasal or perioral formulations.

Example 1.3. Simultaneous Removal of Small Molecules and Inorganic Salts and Concentration of the High Molecular Fraction of the Organic Acid Stabilized Bacterial Extract Alkaline bacterial extracts between pH 10.0 to 11.0 were added to the purification unit, schematized in FIG. 2 which shows a diagram with the connections between 4 vessels, 2 pumps, two filters, two transmembrane pressure (TMP1 and TMP2 pressure regulator valves) and four rotary valves. Transmembrane pressure (TMP): The average applied pressure from the feed to the filtrate side of the filter membrane. TMP [bar]=[(Pressure at Retentate+Pressure at Filtrate)/2]−Pressure at Filtrate. TMP1 and TMP2 valves generate pressure at the filtrate side of the filter and this regulates the transmembrane pressure (TMP) to the appropriate pressure value.

Microfiltration: this filter usually 0.45 to 0.2 μm in this setting is used to remove particles and let go through the filter pores the soluble (non-particulate) material.

Ultrafiltration or nanofiltration: these filters have very small holes with a range of cut-off (cut-off value: pore size expressed in molecular weight in Dalton units (1 Da=1 mass unit, 1 kDa=1000 mass units). A 10 kDa filter retains material larger than the pores or molecules larger than 10 kDa.

Figure 2:
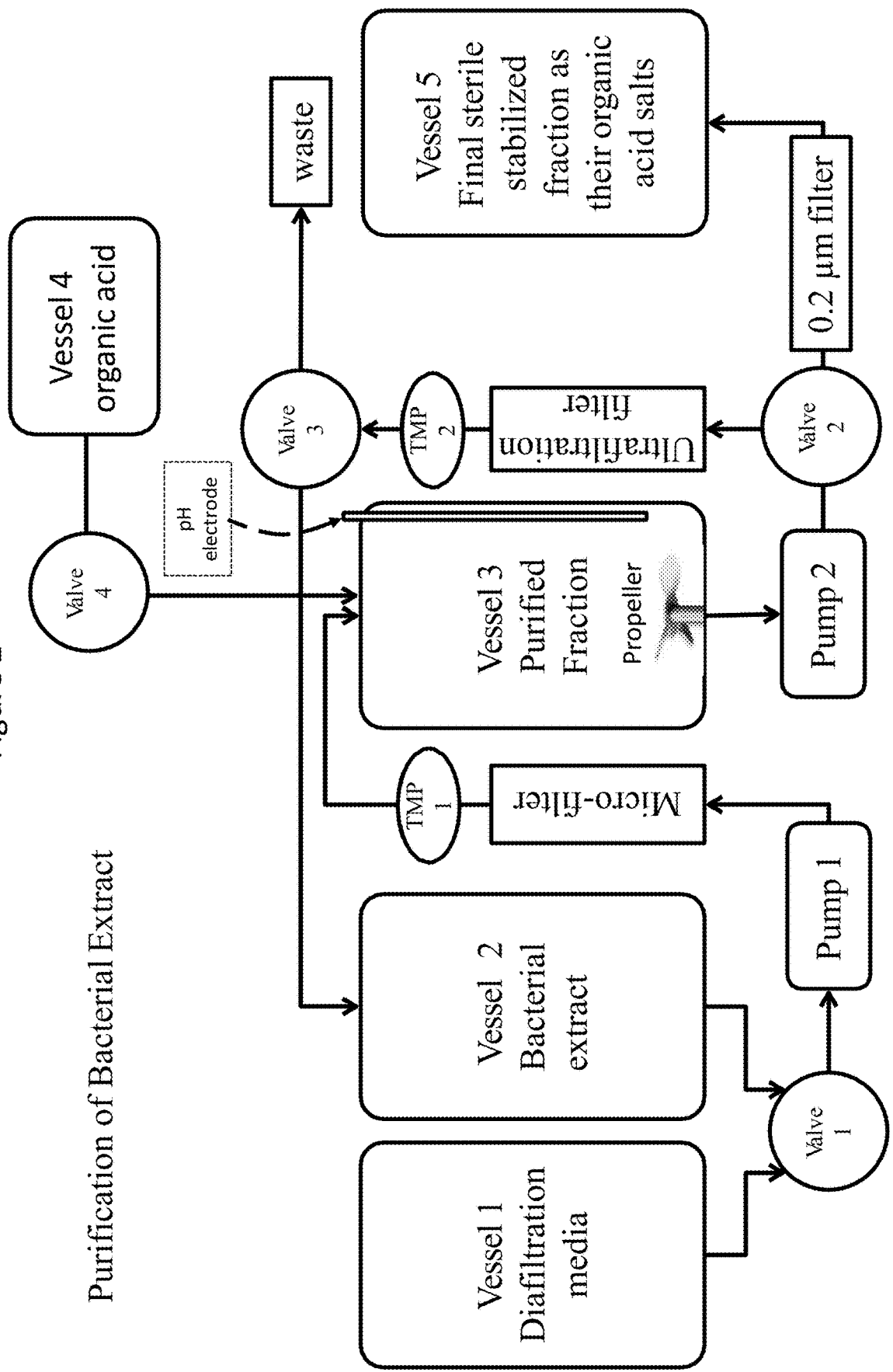
FIG. 2: is a diagram of a tangential flow filtration (TFF) used for the purification of bacterial extracts following alkaline lysis. The diagram shows the different vessels for the crude bacterial extract, the purified fraction, the diafiltration media, the pure organic acid or concentrated organic acid solution, the two pumps, the microfilter holder, the nanofilter/ultrafilter holder, valves, transmembrane pressure regulators (TMP), propeller, pH electrode and connection to the waste. Series of filters can be connected in parallel mode where all filters work simultaneously or in serpentine mode where filters are configured in a serial mode can be used.

Example 1.4: Example of a Five-Step Process Leading to the Stabilized Bacterial Extract Containing Embedded Organic Acids According to the Invention (FIG. 2)

Step 1: Alkaline bacterial extract (pH 10 to 11) containing bacterial cell walls, cell wall fragments and soluble material was added to vessel 2 (FIG. 2) mounted with pump 1 and a microfiltration 0.45 µm filter and the 0.45 µm permeate connected to vessel 3 (FIG. 2). Vessel 3 is connected to pump 2 (FIG. 2) and to an ultrafiltration 10 KD (kDalton) nanofilter which sends the 10 KD permeate back to vessel 2. Permeate containing small molecules and dilute sodium hydroxide is used for continuous extraction in vessel 2 (FIG. 2) of the bacterial extract active water-soluble components.

One half of the initial volume of the bacterial extract in vessel 2 was microfiltered and the 0.45 µm permeated passed into vessel 3.

Step 2: The second filtration unit was then turned on (pump 2) and the 10 kDa permeate coming from 5 vessel 3 returned to vessel 2 using valve 3. Continuous extraction of bacterial soluble components of the crude bacterial extract present in vessel 2 was performed using for the extraction the 10 KD permeate for a total of 10 initial volume of the bacterial extract.

Step 3: This step was performed to remove low molecular weight components present in vessel 3 a diafiltration process was initiated by connecting vessel 1 to pump 1 with fine adjustment of TMP1 regulation to maintain volume in vessel 2 at constant level. Vessel 1 contained water adjusted to pH 10.8 to 11.0 with sodium hydroxide as the diafiltration media. During the diafiltration process, ultrafiltration permeates of vessel 3 was connected to waste using valve 3 and TMP2 adjusted to optimal flow rate. A total of five volumes of diafiltration media were required to remove the undesirable small molecular weight components present in the purified bacterial extract in vessel 3.

Step 4: A concentration step of the purified extract present in vessel 3 was performed after disconnecting vessel 1 and pump 1. Purified extract fraction in vessel 3 was concentrated to half of the initial volume with permeate going to waste via valve 3.

Step 5: The concentrated purified bacterial fraction was stabilized by addition of an organic acid in order to form embedded organic acid salts. This process was performed after closing pump 2 and valve 2. A predefined volume of pure liquid organic acid or respectively for solid organic acids, a predefined volume of a concentrated solution of the organic acid, was added from vessel 4 to vessel 3 via valve 4 to reach a pH value of 7.5±0.2. For pH adjustment, the propeller was turned on during the addition of the organic acid and pH adjusted via a pH electrode mounted in vessel 3.

Step 6: Vessel 3 containing the concentrated purified bacterial fraction in the form of the organic acid salt at pH 7.5 was sterilized inline suing a sterile 0.2 µm filter unit mounted on sterile lines connected to a sterilized vessel 5 (sterile bag or heat sterilized stainless steel vessel).

Depending on the final use of the liquid formulation and the route (intranasal, inhalation as aerosol or solid) a further concentration was applied using pump 2 and ultrafiltration connected to waste via valve 3, to reach 25% of the initial volume. Presence of the organic acid salt allowed achievement of a highly concentrated purified fraction enabling spray drying process, direct use as liquid drops and aerosols. Products with similar pH (7.5±0.5) were obtained with the different organic acids forming embedded salts.

Same process was repeated using respectively 3 kD, 10 kD, 30 kD, 100 kD, 300 kD polysulfone tangential flow filters as well as hollow fibers using 10 kD, 30 kD, 100 kD, 300 kD cut-offs as alternative tangential flow filter design.

Process was initially performed at 1 L laboratory scale using first a concentration step (from 2 fold to reach 500 mL and up to 5 fold concentration to reach a 200 mL volume), unwanted small molecules were washed off by a diafiltration step using a NaOH-water solution at pH 10.5 to pH 11.0 and the desired retentate of the ultrafiltration was further concentrated 2 fold. Then organic acids were added to form salts at pH 7.5±0.5 with the positively charged groups present in the extract in order to stabilize the preparation. Similarly, concentration of high molecular fractions was performed using a concentration step on the ultrafiltration filters removing low molecular fractions using different cut-offs, respectively 3 kD, 10 kD, 30 kD, 100 kD, 300 kD, 1000 kD of the respective ultrafiltration filters.

Organic acids listed in the table below were added with a target pH value of 7.5±0.5. The embedded organic acid salts of the positively charged soluble high molecular fraction of the bacterial extract were kept within the high molecular fraction during the process.

A similar procedure was performed at 10 L, 100 L and finally at 400 L to prepare pilot and industrial batch sizes using a 10 kD cut-off.

Preferably, low molecular weight salts and molecules may be removed by ultrafiltration leading to a concentrated high molecular weight fraction which enhances the antiviral properties of bacterial extract. 500 mL Bacterial extract at pH 10.8 was added on a lab-scale ultrafiltration system mounted with a 10 kDa polysulfone ultrafiltration filter. After a 4-fold concentration of the 500 mL initial volume to approx. 120 to 140 mL, a diafiltration using NaOH-water at pH 11±0.2 was applied. After 5 volumes of diafiltration, the retentate was concentrated down to 100 mL and final volume was adjusted to 125 mL with water prior to addition of the different organic acids on 10 mL aliquots.

The process was applied with different bacterial extracts such as OM alkaline extract purified fractions, Gram positive bacteria purified fractions from alkaline extracts of *Staphylococcus, Streptococcus, Bifidobacterium, Lactobacillus* as well as Gram negative bacterial purified fractions of alkaline extracts of *Escherichia coli, Klebsiella, Branhamella, Hemophilus* strains. Table 2 below recapitulates the organic acids which were used to adjust pH to 7.5. Bacterial alkaline extracts purified fractions after removal of low molecular components were adjusted to pH 7.5 using the following organic acids and assess their stability.

TABLE 2

| Acid/Organic acid | turbidity | Stability at 20° C. to 25° C. | Stability at 4° C. to 8° C. |
|---|---|---|---|
| Formic acid | slightly turbid | Not stable, turbid, precipitate | Not stable, turbid, precipitate |
| Propanoic acid | slightly turbid | Stable, clear solution, no precipitate | Stable, clear solution, no precipitate |
| Lactic acid | slightly turbid | Stable, clear solution, no precipitate | Stable, clear solution, no precipitate |

TABLE 2-continued

| Acid/Organic acid | turbidity | Stability at 20° C. to 25° C. | Stability at 4° C. to 8° C. |
|---|---|---|---|
| 3-hydroxy-propanoic acid | slightly turbid | Stable, clear solution, no precipitate | Stable, clear solution, no precipitate |
| Butanoic acid | clear solution | Stable, clear solution, no precipitate | Stable, clear solution, no precipitate |
| 2-hydroxybutanoic acid | clear solution | Stable, clear solution, no precipitate | Stable, clear solution, no precipitate |
| 3-hydroxybutanoic acid | clear solution | Stable, clear solution, no precipitate | Stable, clear solution, no precipitate |
| Aspartic acid | clear solution | Stable, clear solution, no precipitate | Stable, clear solution, no precipitate |
| Glutamic acid | clear solution | Stable, clear solution, no precipitate | Stable, clear solution, no precipitate |

Example 1.5: Simultaneous Removal of Small Molecules and Inorganic Salts and Concentration of the High Molecular Fraction of the Organic Acid Stabilized Bacterial Extract of *Lactobacillus fermentum* (OM314B)

A volume of 1 L of alkaline bacterial extract of *Lactobacillus fermentum* at pH 10.5±0.3 was added to an ultrafiltration system equipped with a 0.45 µm microfilter and a second ultrafiltration filter with 10 kDalton cut off Bacterial extract was purified using both filters as described in example 7.3 and FIG. 1. First step was a concentration step which was followed by a continuous extraction using 10 volumes of permeate 10 kD as the extraction media.

Then a diafiltration process with 5 volumes of a NaOH solution in water adjusted to pH 10.

A final 4 fold concentration step was added before the addition of the different organic acids forming embedded salts.

The process was performed at 1 L scale using first a concentration step (5 fold, down to approximatively 200 mL), unwanted small molecules were washed off by a diafiltration step using 5 volumes of a NaOH-water solution at pH 10.5. Then organic acids listed in Table 3 below were added to form salts with the positively charged groups present in the extract in order to stabilize the preparation. Similarly, concentration of high molecular fractions was performed using a concentration step on the ultrafiltration filters removing low molecular fractions using other cut-offs, respectively 3 kD, 10 kD, 30 kD, 100 kD, 300 kD of the respective polysulfone filters.

Organic acids listed in the table below were added with a target pH value of 7.5±0.2. The embedded organic acid salts of the positively charged soluble high molecular fraction of the bacterial extract were kept within the high molecular fraction during the process.

In other examples the process was repeated using the following polysulfone ultrafiltration filter cut-offs, respectively 3 kD, 30 kD, 100 kD, 300 kD.

In another example, removal of low molecular weight salts and molecules was performed by ultrafiltration leading to a concentrated high molecular weight fraction which enhances the antiviral properties of *Lactobacillus fermentum* extract. A 500 mL *Lactobacillus fermentum* alkaline extract at pH 10.8 was added to a labscale ultrafiltration system mounted with a 10 kDalton polysulfone ultrafiltration filter. After a 4 fold concentration of the 500 mL initial volume to approx. 120 to 140 mL, a diafiltration using NaOH-water at pH 10.8 to 11.0 was applied. After 5 volumes of diafiltration, the high molecular fraction (retentate) was concentrated down to 100 mL and final volume was adjusted to 125 mL with water prior to addition of the different organic acids on 10 mL aliquots to assess physical stability and antiviral activity.

Table 3 below lists the organic acids used to adjust pH to 7.5 for *Lactobacillus fermentum* extract fractions >10 kDalton.

TABLE 3

| Acid/Organic acid | turbidity | Stability at 20° C. to 25° C. | Stability at 4° C. to 8° C. |
|---|---|---|---|
| Formic acid | slightly turbid | Not stable, turbid, precipitate | Not stable, turbid, precipitate |
| Propanoic acid | slightly turbid | Stable, clear solution, no precipitate | Stable, clear solution, no precipitate |
| Lactic acid | slightly turbid | Stable, clear solution, no precipitate | Stable, clear solution, no precipitate |
| 3-hydroxy-propanoic acid | slightly turbid | Stable, clear solution, no precipitate | Stable, clear solution, no precipitate |
| Butanoic acid | clear solution | Stable, clear solution, no precipitate | Stable, clear solution, no precipitate |
| 2-hydroxybutanoic acid | clear solution | Stable, clear solution, no precipitate | Stable, clear solution, no precipitate |
| 3-hydroxybutanoic acid | clear solution | Stable, clear solution, no precipitate | Stable, clear solution, no precipitate |
| Aspartic acid | clear solution | Stable, clear solution, no precipitate | Stable, clear solution, no precipitate |
| Glutamic acid | clear solution | Stable, clear solution, no precipitate | Stable, clear solution, no precipitate |

In other examples the process was repeated using microfiltration hollow fibers 0.45 µm and 0.2 µm and ultrafiltration hollow fibers with 30 kD and 100 kD cut-offs as an alternative to the tangential flow filter design with a better flow rate and shorter process time.

A similar procedure was performed at 10 L, 100 L and finally at 400 L to prepare pilot and industrial batch sizes using a 10 kD cut-off.

Example 1.6: Process for *Lactobacillus fermentum* I 3929p (OM314B) and Analytical Characterization Example 1.6.1 Process 4 *Lactobacillus fermentum* I 3929p Lysis: *Lactobacillus fermentum* I 3929p biomass was thawed overnight at room temperature. The lysis performed was a lysis with a total mass of 2 kg including 25 g of total dry weight upon dessication (RS) per kg of lysis. The necessary quantity of biomass (depending on biomass RS result) was deposited in a 2500 mL mini-cask (reference: Semadeni no 6863) and the 2 kg qsp was made with 40° C.±5° C. preheated purified water. The pH of this solution was then adjusted to 10.0±0.1 using NaOH 10 N (pH: 9.98 adjusted with 2.8 mL of NaOH 10 N).

The alkaline lysis was transferred in a 40° C.±1° C. warm room under stirring (to have a product vortex of 1 cm). After 4 h 00±5 min of lysis, the pH was controlled (end lysis pH: 9.28).

A sample corresponding to the lysate at the end of the lysis (called "process 4-E1-lysate") was carried out at this step.

Filtering 1: The installation for the filtration of the product was prepared in accordance with the diagram (FIG. 2). The filtration system consists of 2 filtration loops. A first microfiltration (called MF) consisting of a tank (vessel 2 on FIG. 2), a pump (pump 1 on FIG. 2) and a filtration system with a cut-off point of 0.45 µm (micro-filter on FIG. 2). The second loop, ultrafiltration (called UF), consists of a tank (vessel 3 on FIG. 2), a pump (pump 2 on FIG. 2) and a filtration system with a cut-off point of 30 kDa (ultrafiltration filter on FIG. 2). The filtration took place at the laboratory scale with an implemented volume of 2000 mL.

Before starting the process, filtration system was checked for reproducibility over several batches. To verify the correct filterability of the product, an Normalized Water Permeability (NWP) was performed on the filtration system.

The lysate used for the production was stirred to have a product vortex of 1 cm. The temperature of the product was cooled to room temperature while waiting the filtering process to start. In this process there was no initial pH adjustment, so the filtering process started immediately.

Initial concentration step: The product used for the first step of filtration had the following parameters: no pH adjustment after lysis (pH: 9.28), temperature 38° C., stirred to have a product vortex of 1 cm.

The MF loop pump (pump 1 on FIG. 2) was started at 40% of the process speed to charge the system with the product. Once this step was completed, the recirculation of the product on the MF loop started and the pump speed was increased regularly to reach 75% of the process speed. Recirculation allows the hydrophilic filtration system to be conditioned by eliminating the air bubbles present in the system.

When the flow rate and the pressure were stable, the filtration system was considered as conditioned. Then, the permeate valve of the MF loop was opened in order to perform an initial concentration of the product with a concentration factor to 0.5 (pressure input: 270 mbar, permeate flow rate: 75 mL/min). During the initial concentration, the pump (pump 1 on FIG. 2) speed was gradually increased to 100% (100 rpm corresponding to 600 mL/min) of the process speed.

Parallel to this step, the UF loop was conditioned. The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Diafiltration: When the one-half (0.5×) concentration factor was reached, the UF permeate was opened in order to start the diafiltration of the product (pressure input: 793 mbar, permeate flow rate: 53 mL/min). In order to have an optimal extraction of the product, the MF TMP (Trans Membrane Pressure) which was controlled by valve 1 on FIG. 2, must be set at 850 mbar (pressure input: 1060 mbar, permeate flow rate: 47 mL/min).

During the diafiltration, the speed of the UF pump (pump 2 on FIG. 2) was set to reach an UF permeate flow equal to the permeate flow MF. Indeed, the volume on the MF tank (vessel 2 on FIG. 2) had to remain as stable as possible during the diafiltration step.

The diafiltration was performed by cycle. At the end of the initial concentration, there was a volume present in the MF tank (vessel 2 on FIG. 2). Once this volume passed through the MF filtration system, one cycle was realized. In this process, the diafiltration needed 5 cycles.

Final concentration: At the end of the 5 diafiltration-cycles, the UF pump was stopped. When the MF input pressure started to increase, the MF pump was shut down. At the end of this first filtration step, the product of interest contained elements smaller than 0.45 μm in size.

Filtering 2: The product of interest harvested (mass: 996.0 g) then undergone a second stage of 5 cycles of purification on the UF loop with a 30 kDa cut-off (vessel 3, pump 2 and ultrafiltration filter on FIG. 2). The 30 kDa permeate was discarded with valve open to waste (FIG. 2). Volume of 30 kDa retentate was maintained constant during this second filtering step of purification, by adding of NaOH 0.001 N solution at pH 10.0 for the diafiltration. The UF loop pump (pump 2 on FIG. 2) was started at 40% of the process speed to charge the system with the product.

Once this step was completed, the recirculation of the product on the UF loop started and the pump speed was increased regularly to reach 75% of the process speed. Recirculation allows the hydrophilic filtration system to be conditioned by eliminating the air bubbles present in the system.

Once the filtration system conditioned, the UF permeate was opened in order to start the filtering 2 of the product (pressure input: 640 mbar, permeate flow rate: 108 mL/min). In order to have an optimal extraction of the product, the UF TMP (Trans Membrane Pressure) which was controlled by valves 2 and 3 on FIG. 2, must be set at 850 mbar (pressure input: 900 mbar, permeate flow rate: 134 mL/min).

During the filtering 2 step, the volume on the UF tank (vessel 3 on FIG. 2) had to remain as stable as possible. So, as the level of the UF tank (vessel 3 on FIG. 2) decreased, there was an addition of NaOH 0.001 M solution. The 5 cycles corresponding to a volume of NaOH 0.001M diafiltration solution added equivalent to 5 times the volume of product of interest harvested (5 cycles of diafiltration).

At the end of filtering 2 step, the final product was harvested (mass: 951.4 g), and then separated into 2 equal parts. At the end of this second filtration step, the product of interest contained elements smaller than 0.45 μm and taller than 30 kDa in size.

A sample corresponding to the filtrate before neutralization (called "process 4-E2-filtrate") was carried out at this step.

The first part of the filtrate was then neutralized with propionic acid 1% at pH 7.0±0.2 (pH: 7.13 adjusted with 0.5 mL of propionic acid 1%), then sterilized under biosafety cabinet using a filtration with 0.2 μm polyethersulfone (PES 0.2 μm) sterilizing membrane.

A sample corresponding to the neutralized filtrate at the end of the process (called "process 4-E3-neutralized filtrate (propionic acid)" OM314B) was carried out at this step.

At the same time, the second part of the filtrate was subdivided into 9 equal parts. Each of these parts was then neutralized at 7.0±0.2 with hydrochloric 2.5% (pH: 7.07) or with organic acids (OM314B): formic 1/100 (pH: 7.16), acetic 1/100 (pH: 7.16), 3-hydroxy-butanoic 1/100 (pH: 7.14), aspartic 0.1% (pH: 7.18), lactic 1/50 (pH: 7.09), glutamic 0.1% (pH: 7.14), pyruvic 1/100 (pH: 7.16), ascorbic 0.1% (pH: 7.18)).

Finally, the different products were sterilized under biosafety cabinet using a filtration with PES 0.2 μm sterilizing membrane.

A sample corresponding to the different neutralized filtrates at the end of the process (called "process 4-E4-neutralized filtrate (name of acid)") was carried out at this step.

TABLE 4

Sample codes summary.

| | |
|---|---|
| Lysate | Process 4-E1-lysate |
| Filtrate | Process 4-E2-Filtrate |

TABLE 4-continued

Sample codes summary.

| | |
|---|---|
| Standard Neutralized Filtrate | Process 4-E3-neutralized filtrate (propionic acid) |
| Acid 1 neutralized Filtrate | Process 4-E4-neutralized filtrate (hydrochloric acid) |
| Acid 2 neutralized Filtrate | Process 4-E4-neutralized filtrate (formic acid) |
| Acid 3 neutralized Filtrate | Process 4-E4-neutralized filtrate (acetic acid) |
| Acid 4 neutralized Filtrate | Process 4-E4-neutralized filtrate (3-hydroxy-butanoic acid) |
| Acid 5 neutralized Filtrate | Process 4-E4-neutralized filtrate (aspartic acid) |
| Acid 6 neutralized Filtrate | Process 4-E4-neutralized filtrate (lactic acid) |
| Acid 7 neutralized Filtrate | Process 4-E4-neutralized filtrate (glutamic acid) |
| Acid 8 neutralized Filtrate | Process 4-E4-neutralized filtrate (pyruvic acid) |
| Acid 9 neutralized Filtrate | Process 4-E4-neutralized filtrate (ascorbic acid) |

Example 1.6.2 Analytical Characterization Methods a) Dry Weight Method (Lysate)

The determination of the dry residue of lysate was made by halogen desiccation following a principle of thermogravimetry: at the beginning of the measurement operation, the sample's weight was defined, the sample was then quickly heated with the integrated halogen heater and the humidity evaporated.

During the drying, the device weighed the sample in a continuous way. Once the drying ended, the weight of the dry residue was indicated.

About 2 to 5 g of lysate (M) was accurately weighed. The following parameters were used: Heating Mode: progressive; Stop Mode: constant weight; Final Temperature: 105° C. Once the analysis ended, the weighing ticket was automatically printed indicating the final mass of the obtained residue (m). Dry Residue (expressed in mg/g)=(m/M)×1,000. Measures were performed on the sample directly (total) and after centrifugation 5 min at 5,000×g (supernatant).

b) Dry Weight Method (Filtrate)

Dry weight of filtrate was performed according to Ph.Eur 2.2.32 using about 5 g of filtrate dried during 16 hours at 105° C. (oven). Results were expressed in mg/g.

c) Lowry Method

This assay was based on the reaction of proteins with an alkaline copper tartrate solution and Folin reagent (based on Ph. Eur. 2.5.33). There were two steps which lead to a colorimetric reaction: the reaction between proteins and copper in an alkaline medium, and the subsequent reduction of Folin reagent by the copper-treated protein. Proteins effected a reduction of the Folin reagent producing reduced species which had a characteristic blue color with maximum absorbance at 750 nm. The results were expressed relative to a Bovine Serum Albumin protein (BSA) standard curve.

Samples preparation: 1.9 mL of phosphate buffer pH 11 (3.55 g of $Na_2HPO_4$ and 41 mL of 0.1 M NaOH for 1 L of water) were added to 100 μL of each sample and vortexed. BSA standard preparation: BSA solution was diluted with phosphate buffer to prepare the standard curve with 6 points between 0 and 420 μg/mL. Procedure: 20 μL of samples and standard solutions were loaded on a 96 wells microplate. 25 μL of A reagent (Bio-Rad® Lowry kit) were added immediately in each well and incubated 10 min at room temperature. 200 μL of B reagent (Bio-Rad® Lowry kit) were added, mixed and incubated 20 min at room temperature. The absorbance were read at 750 nm after mixing. Results: Protein concentrations were calculated from the standard curve: Protein Concentration (mg/mL)=[(y−b)/a]*sample dilution, with y=absorbance of the sample; a=slope of calibration curve; b=ordinate at the origin of calibration curve and results expressed as mg protein/mL.

d) Total Sugar Method

Carbohydrates, when heated with anthrone in a sulfuric medium, form a chromophore absorbing at 625 nm.

Glucose standard preparation: D-Glucose were solubilized and diluted with purified water to prepare the standard curve with 5 points between 0 and 100 (μg/mL). Procedure: 0.1 mL of the solution to be examined (i.e. the concentrate) and 0.9 mL of purified water were added in a tube placed in an ice-bath. 5.0 mL of Anthrone reagent (160 mg of Anthrone in 100 mL of 85% sulfuric acid) were added, and shaked vigorously. Solutions were heated for 15 min in a boiling water-bath, then cooled in an ice-bath, shaked from time to time. Solutions were allowed to stand at room temperature for 15 min. The tubes were vortexed, and the solution were transferred into the measuring cell and allowed to stand for 30 min at room temperature before the measurement of the absorbance at 625 nm. Results: Carbohydrates concentrations were calculated from the standard curve: Carbohydrates content (mg/mL)=([(y−b)/a]* 10)/(1,000), with y=absorbance of the sample; a=slope of calibration curve; b=ordinate at the origin of calibration curve and results expressed as mg carbohydrates/mL.

e) Total RNA Assay

Total RNA purification and assay were carried out based on RNeasy® Mini kit data sheet according to the supplier's recommendations. Briefly, 600 μL bacterial extract were transferred into RNeasy® spin column and were centrifuged for 15 s at 8,000×g. Then, 700 μL buffer RW1 were added to the RNeasy® column and centrifuged for 15 s at 8,000×g to wash spin column membrane. The same step was performed twice with 500 μL buffer RPE and centrifuged for 15 s at 8,000×g and for 2 min at 8,000×g, consecutively. To eliminate any possible carryover of buffer RPE, spin column was centrifuged at full speed for 1 min. To elute RNA, 30 μL RNase-free water was added directly to the spin column membrane and column was centrifuged for 1 min at 8,000× g. Purified total RNA was detected at 260 nm with Nano-Drop (ThermoFischer) spectrophotometer.

f) Total DNA Assay

Total DNA purification and assay were carried out based on DNeasy® Blood and Tissue kit data sheet according to the supplier's recommendations. Briefly, 600 μL bacterial extract were transferred into DNeasy® Mini spin column and were centrifuged for 1 min at 6,000×g. Then, 500 μL buffer AW1 were added to the DNeasy® Mini column and centrifuged for 1 min at 6,000×g. 500 μL buffer AW2 were added and spin column was centrifuged for 3 min at 20,000×g to dry DNA membrane. 100 μL buffer AE were added onto the DNeasy® membrane, incubated 1 min and centrifuged for 1 min at 6,000×g to elute DNA. For maximum DNA yield, elution was repeated once. Purified total DNA was detected at 260 nm with NanoDrop spectrophotometer.

g) Limulus Amebocyte Lysate LAL Assay

Endotoxin assay was carried out based on Pierce™ Chromogenic Endotoxin Quant Kit data sheet according to the supplier's recommendations. All samples were diluted to 1:10 to avoid that sample's intrinsic color altered the absorbance readings. Briefly, endotoxin standard solutions (range 0.1-1.0 EU/mL) were prepared from endotoxin stock solution (10 EU/mL). 50 µL endotoxin standard, blank (endotoxin-free water) and samples were placed per well. 50 µL reconstituted Amebocyte Lysate Reagent were added and plate was incubated for 15 min at 37° C. 100 µL Chromogenic substrate solution were added per well and incubated at 37° C. for 6 min. At exactly 6 min, 50 µL of stop solution (25% acetic acid) were added. Optical density was measured at 405 nm immediately after assay completion.

h) Amino Acid Method:

D- and L-amino acid determination was performed by reverse phase high performance liquid chromatography (HPLC). After hydrolysis of the samples in micro-wave oven, amino acid were derivatized using o-phthaldialehyde together with chiral thiol N-isobutyryl-L-cysteine. Detection was performed by UV detection at 338 nm. (Bruckner, H., T. Westhauser, H. Godel. Liquid chromatographic determination of D- and L-amino acids by derivatization with O-phthaldialdehyde and N-isobutyryl-L-cysteine. *J. Chromatography A*, 1995, 711, 201-21).

Standard solutions were prepared with the different amino acids: Aspartic acid (Asp), Serine (Ser), Glutamic acid (Glu), Histidine (His), Arginine (Arg), Threonine (Thr), Alanine (Ala), Tyrosine (Tyr), Valine (Val), Methionine (Met), Lysine (Lys), Isoleucine (Ile), Leucine (Leu), Phenylalanine (Phe), Glycine (Gly), Cystine (Cys)) at 2.5 µmol/mL in hydrochloric acid (HCl) 0.01N. Those solutions were diluted to 0.5 µmol/mL using 0.1M sodium tetraborate decahydrate buffer at pH 9.2. In a tube, 2.0 mL of sample solutions were added to 2.0 ml of water, 240 µl of 1-dodecanethiol and 8 mL of HCl 25%. They were hydrolyzed in micro-wave oven at 180° C., 1320 Watt during 15 min. Solutions were allowed to stand to room temperature and filtered at 5 µm. 50.0 µl were evaporated to dryness and reconstituted with 100 µl of HCl 0.01N. Sample and standard solutions were kept into the HPLC system at 10° C. and injected with the following injection mode: 5.0 µl of 0.1M sodium tetraborate decahydrate buffer at pH 9.2, 2.0 µl of derivatization solution (23 mg of phthaldialehyde and 50 mg of N-isobutyryl-L-cysteine solubilized in 1.0 ml methanol), 2.0 µl sample or standard solution were drawn by the autosampler, mixed 5 times, and injected. HPLC column was Supelcosil C18, 5 µm, 4.6×250 mm, with Supelco LC 18, 5 µm, 4.6×20 mm pre-column. For elution a gradient was formed from 23 mM sodium acetate adjusted to pH 5.9 (eluent A) and a mixture of methanol-acetonitrile (12:1, v/v) (eluent B). The gradient was formed from 4% B to 33% B in 45 min, then to 56% B during 30 min (and rinsing step up to 85% B) at a flow rate at 1 ml/min. Free amino acids were also tested separately for each sample without the HCl hydrolysis step using directly E2-Filtrate solution in HPLC vials and no free amino acids were detected were detected without hydrolysis.

i) Spectrophotometric Results Obtained During Stability

Figure 27:
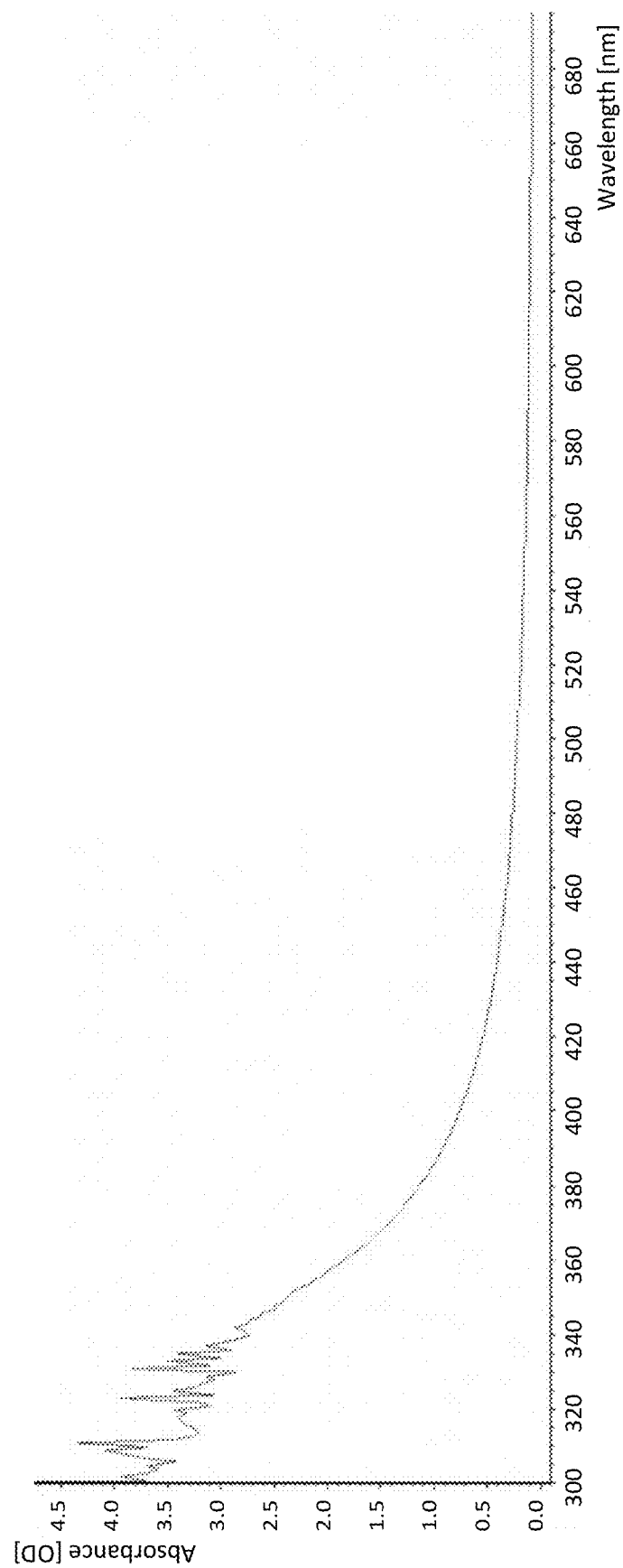
FIG. 27: represents a noisy spectrum indicating precipitate in solution (given as atypical example of unstable bacterial extract).
Figure 28:
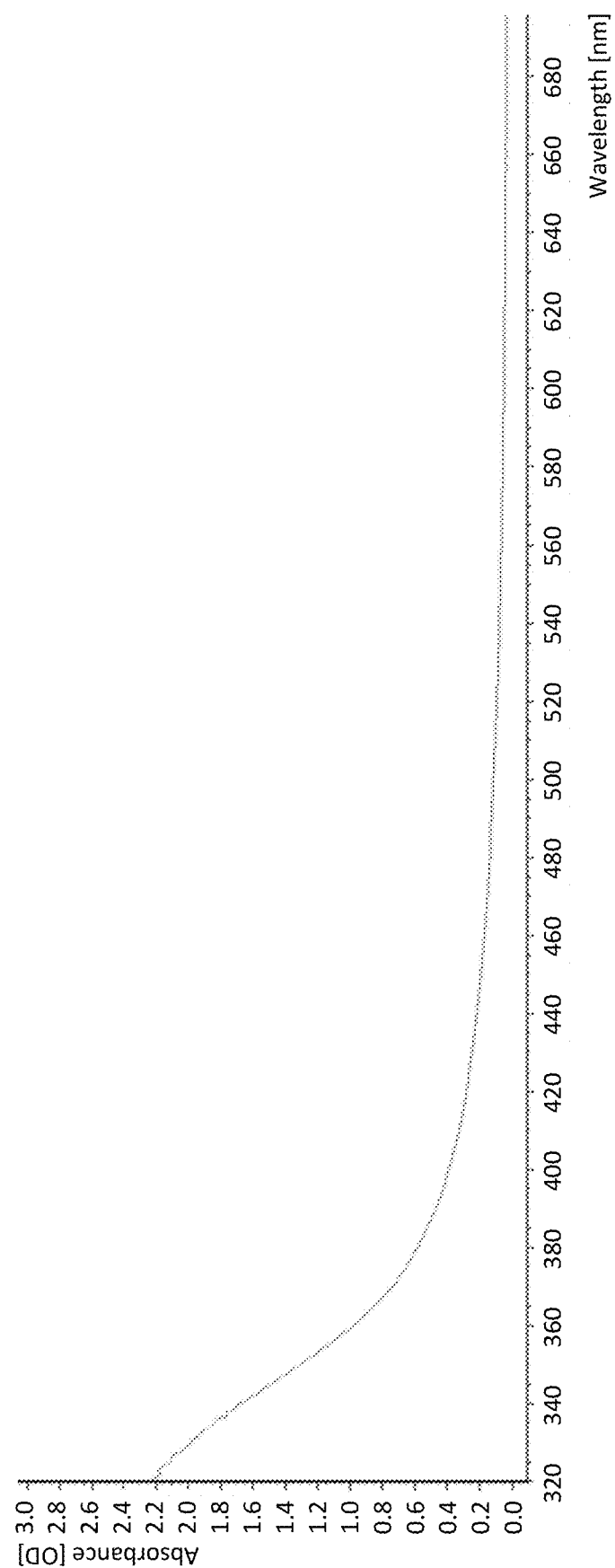
FIG. 28: represents a smooth spectrum indicating clear solution (given as a typical example of stable bacterial extract).

Neutralized filtrate solutions were put in stability at room temperature (20° C.+/−5° C.) or at 4° C. At each time point, absorbance of solutions was recorded between 300 and 700 nm. Spectrum profile were assessed visually as noisy (e.g. FIG. 27—indicating a precipitation in the solution) or smooth (e.g. FIG. 27). Absorbance were extracted at 320 nm for a quantitative evaluation.

j) Results at Release:

All E2-Filtrate solutions were frozen after process and were thawed at 4° C. overnight before analysis.

Example 1.6.3. Analytical Characterization of Process 4 *Lactobacillus Fermentum* I 3929p Final Samples at Release (T0)

TABLE 5

Process 4 samples results

| Test | Sample | Result | Unit |
|---|---|---|---|
| Dry weight (total) | Process 4-E1-lysate | 27.7 | [mg/g] |
| Dry weight (supernatant) | Process 4-E1-lysate | 5.5 | [mg/g] |
| Dry weight (filtrate) | Process 4-E2-Filtrate | 1.5 | [mg/g] |
| Proteins total | Process 4-E2-Filtrate | 0.44 | [mg/mL] |
| Sugar total | Process 4-E2-Filtrate | 0.21 | [mg/mL] |
| Endotoxin LAL* | Process 4-E3-neutralized filtrate (propionic acid) | ND | [EU/mL] |
| DNA** | Process 4-E3-neutralized filtrate (propionic acid) | ND | [µg/mL] |
| RNA*** | Process 4-E3-neutralized filtrate (propionic acid) | ND | [µg/mL] |

ND = not detected;

*Endotoxin LAL: limit of detection = 0.1 EU/mL;

**DNA: limit of detection = 3.60 µg/mL, limit of quantification = 12.01 µg/mL;

***RNA: limit of detection = 4.29 µg/mL, limit of quantification = 14.32 µg/mL

TABLE 6

Process 4—Total Amino Acids

| Amino Acid | Concentration (µmol/mL) | %/AA (D vs L) |
|---|---|---|
| L-Asp | 0.00 | NA |
| D-Asp | 0.00 | NA |
| L-Glu | 0.17 | 100 |
| D-Glu | 0.00 | 0 |
| L-Ser | 0.00 | NA |
| D-Ser | 0.00 | NA |
| L-Thr | 0.00 | 0 |
| D-Thr | 0.31 | 100 |
| L-His | 0.00 | NA |
| Gly | 0.00 | NA |
| D-His | 0.00 | NA |
| L-Ala | 0.11 | NA |
| L-Arg | 0.04 | NA |
| D-Arg + D-Ala | 0.00 | NA |
| L-Tyr | 0.00 | NA |
| D-Tyr | 0.00 | NA |
| L-Val | 0.00 | NA |
| L-Met | 0.00 | NA |
| D-Met | 0.00 | NA |
| L-Cys | 0.00 | NA |
| D-Val | 0.00 | NA |
| L-Ile | 0.00 | NA |
| L-Phe | 0.00 | NA |
| D-Phe | 0.00 | NA |
| L-Leu | 0.32 | 100 |
| D-Ile | 0.00 | NA |
| D-Leu | 0.00 | 0 |
| L-Lys | 0.08 | 100 |
| D-Lys | 0.00 | 0 |

TABLE 7

Process 4-stability of solution through absorbance measurement

| Time points (Months) | | Process 4 | Propionic Acid | Hydrocloric Acid | Aspartic Acid | Formic Acid | Lactic Acid | 3-hydroxi-butanoic Acid | Ascorbic Acid | Acetic Acid | Pyruvic Acid | Glutamic Acid | HCL Industrial Batch 1619064 |
|---|---|---|---|---|---|---|---|---|---|---|---|---|---|
| T0 | | Abs [AU] | 0.837 | 0.833 | 0.809 | 0.841 | 0.846 | 0.835 | 0.815 | 0.84 | 0.844 | 0.794 | 2.865 |
| | | Evaluation | smooth | smooth | smooth | smooth | smooth | smooth | smooth | smooth | smooth | smooth | noisy |
| T1 | 4° C. | Abs [AU] | 0.852 | 0.847 | 0.829 | 0.857 | 0.857 | 0.851 | 0.836 | 0.869 | 0.866 | 0.807 | 3.17 |
| | | R (%) | 102% | 102% | 102% | 102% | 101% | 102% | 103% | 103% | 103% | 102% | 111% |
| | | Evaluation | smooth | smooth | smooth | smooth | smooth | smooth | smooth | smooth | smooth | smooth | noisy |
| | RT | Abs [AU] | 0.821 | 0.848 | 0.793 | 0.84 | 0.82 | 0.833 | 0.811 | 0.821 | 0.839 | 0.796 | 3.17 |
| | | R (%) | 98% | 102% | 98% | 100% | 97% | 100% | 100% | 98% | 99% | 100% | 111% |
| | | Evaluation | smooth | smooth | smooth | smooth | smooth | smooth | smooth | smooth | smooth | smooth | noisy |
| T3 | 4° C. | Abs [AU] | 0.838 | 0.844 | 0.817 | 0.832 | 0.862 | 0.84 | 0.835 | 0.851 | 0.86 | 0.803 | 3.148 |
| | | R (%) | 100% | 101% | 101% | 99% | 102% | 101% | 102% | 101% | 102% | 101% | 110% |
| | | Evaluation | smooth | smooth | smooth | smooth | smooth | smooth | smooth | smooth | smooth | smooth | noisy |
| | RT | Abs [AU] | 0.816 | 0.853 | 0.808 | 0.848 | 0.823 | 0.85 | 0.823 | 0.825 | 0.851 | 0.806 | 3.159 |
| | | R (%) | 97% | 102% | 100% | 101% | 97% | 102% | 101% | 98% | 101% | 102% | 110% |
| | | Evaluation | smooth | smooth | smooth | smooth | smooth | smooth | smooth | smooth | smooth | smooth | noisy |
| T6 | 4° C. | Abs [AU] | 0.884 | 0.866 | 0.804 | 0.837 | 0.834 | 0.819 | 0.816 | 0.839 | 0.836 | 0.778 | 3.046 |
| | | R (%) | 106% | 104% | 99% | 100% | 99% | 98% | 100% | 100% | 99% | 98% | 106% |
| | | Evaluation | smooth | smooth | smooth | smooth | smooth | smooth | smooth | smooth | smooth | smooth | noisy |
| | RT | Abs [AU] | 0.81 | 0.914 | 0.837 | 0.879 | 0.863 | 0.878 | 0.857 | 0.859 | 0.906 | 0.835 | 2.985 |
| | | R (%) | 97% | 110% | 103% | 105% | 102% | 105% | 105% | 102% | 107% | 105% | 104% |
| | | Evaluation | smooth | smooth | smooth | smooth | smooth | smooth | smooth | smooth | smooth | smooth | noisy |

Abs: absorbance at 320 nm; RT: room temperature (20° C. +/− 5° C.); Evaluation: visual evaluation of the spectrum Industrial batch described in WO 2008/109669 (OM-13-BV) neutralized with hydrochloric acid (HCL industrial Batch 1619064) presented precipitate starting already at T0 immediately after neutralization.

Process 4—E4—neutralized filtrates were physically stable at 4° C. or room temperature for at least 6 months. They are considered as stable in those conditions for 12 months.

Mip3-Alpha (CCL20) Results Obtained During Stability:

Chemokine (C—C motif) ligand 20 (CCL20) or liver activation regulated chemokine (LARC) or Macrophage Inflammatory Protein-3 (MIP-3-alpha, CCL20) is a small cytokine belonging to the CC chemokine family. It is strongly chemotactic for lymphocytes and weakly attracts neutrophils. CCL20 is implicated in the formation and function of mucosal lymphoid tissues via chemoattraction of lymphocytes and dendritic cells towards the epithelial cells surrounding these tissues. CCL20 elicits its effects on its target cells by binding and activating the chemokine receptor CCR6.

THP-1 cell line was purchased from ATCC collection, #TIB-202. THP-1 cell line was derived from peripheral blood of 1-year old male with acute monocytic leukemia. Vials of a THP-1 Working Cell Bank used in this bioassay as macrophage-like cells after differentiation.

Neutralized filtrate solutions were put in stability at room temperature (20° C.+/−5° C.) or at 4° C. Samples were taken at different time points and frozen for a further bioassay. All the solutions (T0 and stability time points) were thawed at 4° C. overnight before analysis.

Differentiation: THP-1 cells were differentiated using Phorbol 12-Myristate 13-Acetate (PMA) to have a final concentration of 100 ng/mL of PMA in the cells suspension (1×10$^6$ cells/mL). 100.0 µL/well of PMA cells suspension was distributed in each well of the 96 wells cell culture plate. Cells were incubated 72 hours at 37° C.

Stimulation: A serial dilution in 10 points (serial dilution in 3.16-fold) was performed with culture medium in a deepweel plate: from 2 µg/mL to 0.06 µg/mL of PAM3CSK4 (reference positive control for MIP-3α secretion). A serial dilution in 6 points (serial dilution in 3.16-fold) was performed with culture medium in a deepweel plate: 200 µL of Test Sample into the first well of the deepwell+400 µL of culture medium, then 190 µL was diluted with 410 µL of culture medium (3.16-fold). 100 µL/w of supernatants was removed from plate with cells. 100.0 µL/w of culture medium was distributed into each well of plate with cells. The plate was incubated 24 hours at 37° C.

Harvesting supernatant: 75 µL of supernatant in each well was harvested and distributed it into a 96 PP microplate. The plate was sealed and stored in ultra-low freezer until the ELISA assay was performed. ELISA test: The microplate wells were coated with 100.0 µL/well anti-human MIP-3α (capture antibody). The plate was cover with sealing foil and incubated appropriately. After completion of the incubation, washing steps was performed with an automatic microplate washer. The day of saturation step, the supernatant plate was thawed at +4° C. Saturation step: 250.0 µL/well of reagent diluent was added (1% BSA in PBS) and plates were incubated as appropriate. During the saturation step, serial dilutions for supernatants and standards MIP-3α were prepared. A standard curve was run on each ELISA plate. After completion of the incubation, washing steps were performed, and samples distribution was done into the wells, plates were incubated as appropriate. After completion of the incubation, washing steps were performed and Biotinylated goat anti-human MIP-3α (Detection antibody step) was distributed. Plates were incubated as appropriate. After completion of the incubation, washing steps were performed and Streptavidin-HRP conjugate was distributed was distributed. Plates were incubated as appropriate. After completion of the incubation, washing steps were performed, addition of the enzyme substrate was done, and OD was read at 450 nm. The blank reduction and wavelength correction at 540 nm were performed in accordance with the supplier recommendations of the ELISA kit.

Process 4—bioassay results during stability shows that Process 4—E3—neutralized filtrate were stable during at least 1 month at room temperature (20° C.+/−5° C.) or 4° C.

Example 1.7 Poly-Alkaline Lysates Mixture of 18 E. coli Strains

Example 1.7.1. Process No 5 Poly-Alkaline Lysates Mixture of 18 E. coli Strains (OM314C)

Alkaline lysis: A part of *E. coli* mixture of 18 strains alkaline lysate as described in WO2008/109667 was recovered in production and was stored in a 2500 mL mini-cask (reference: Semadeni no 6863).

A sample corresponding to the lysate at the end of the lysis (called "process 5-E1-lysate") was carried out at this step.

Filtering 1: The installation for the filtration of the product was prepared in accordance with the diagram (FIG. 2). The filtration system consists of 2 filtration loops. A first microfiltration (called MF) consisting of a tank (vessel 2 on FIG. 2), a pump (pump 1 on FIG. 2) and a filtration system with a cut-off point of 0.45 µm (micro-filter on FIG. 2). The second loop, ultrafiltration (called UF), consists of a tank (vessel 3 on FIG. 2), a pump (pump 2 on FIG. 2) and a filtration system with a cut-off point of 30 kDa (ultrafiltration filter on FIG. 2). The filtration took place at the laboratory scale with an implemented volume of 2000 mL.

Before starting the process, we had to ensure that the filtration system was reproducible over batches. To verify the correct filterability of the product, an NWP (Normalized Water Permeability) was performed on the filtration system.

The lysate used for the production was first diluted 4 times with purified water (500.8 g of lysate and 1502.7 g of purified water). The product was stirred to have a product vortex of 1 cm. The temperature of the product was cooled to room temperature while waiting the filtering process to start. In this process there was a pH adjustment at pH 10.5-10.8 (pH: 10.68 adjusted with 2.1 mL of pure pyruvic acid).

Initial concentration: The product used for the first step of filtration had the following parameters (pH: 10.68, temperature 29° C., stirred to have a product vortex of 1 cm). The MF loop pump (pump 1 on FIG. 2) was started at 40% of the process speed to charge the system with the product. Once this step was completed, the recirculation of the product on the MF loop started and the pump speed was increased regularly to reach 75% of the process speed. Recirculation allows the hydrophilic filtration system to be conditioned by eliminating the air bubbles present in the system.

When the flow rate and the pressure were stable, the filtration system was considered as conditioned. Then, the permeate valve of the MF loop was opened in order to perform an initial concentration of the product with a concentration factor to 0.5 (pressure input: 200 mbar, permeate flow rate: 89 mL/min). During the initial concentration, the pump (pump 1 on FIG. 2) speed was gradually increased to 100% (100 rpm corresponding to 600 mL/min) of the process speed.

Parallel to this step, the UF loop was conditioned. The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Diafiltration: When the 0.5 concentration factor was reached, the UF permeate was opened in order to start the diafiltration of the product (pressure input: 786 mbar, permeate flow rate: 80 mL/min). In order to have an optimal extraction ofthe product, the MF TMP (Trans Membrane Pressure) which was controlled by valve 1 on FIG. 2, must be set at 850 mbar (pressure input: 950 mbar, permeate flow rate: 60 mL/min). During the diafiltration, the speed of the UF pump (pump 2 on FIG. 2) was set to reach an UF permeate flow equal to the permeate flow MF. Indeed, the volume on the MF tank (vessel 2 on FIG. 2) had to remain as stable as possible during the diafiltration step.

The diafiltration was performed by cycle. At the end of the initial concentration, there was a volume present in the MF tank (vessel 2 on FIG. 2). Once this volume passed through the MF filtration system, one cycle was realized. In this process, the diafiltration needed 5 cycles.

Final concentration: At the end of the 5 diafiltration cycles, the UF pump was stopped. When the MF input pressure started to increase, the MF pump was shut down. At the end of this first filtration step, the product of interest contained elements smaller than 0.45 µm in size.

Filtering 2: The product of interest harvested (mass: 1146.3 g) then undergone a second stage of 5 cycles purification on the UF loop with cut-off point 30 kDa (vessel 3, pump 2 and ultrafiltration filter on FIG. 2). The permeate was waste as mentioned on FIG. 2. The constant volume was maintained during this second filtering step of purification, by adding of NaOH 0.001 N solution at pH 10.0.

The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Once the filtration system conditioned, the UF permeate was opened in order to start the filtering 2 of the product (pressure input: 650 mbar, permeate flow rate: 76 mL/min). In order to have an optimal extraction of the product, the UF TMP (Trans Membrane Pressure) which was controlled by valves 2 and 3 on FIG. 2, must be set at 850 mbar (pressure input: 960 mbar, permeate flow rate: 105 mL/min).

During the filtering 2 step, the volume on the UF tank (vessel 3 on FIG. 2) had to remain as stable as possible. So, as the level of the UF tank (vessel 3 on FIG. 2) decreased, there was an addition of NaOH solution. The 5 cycles corresponding to a volume of NaOH solution added equivalent to 5 times the volume of product of interest harvested.

At the end of filtering 2 step, the final product was harvested (mass: 1042.7 g), and then separated into 2 equal parts. At the end of this second filtration step, the product of interest contained elements smaller than 0.45 µm and taller than 30 kDa in size. A sample corresponding to the filtrate before neutralization (called "process 5-E2-filtrate") was carried out at this step.

The first part of the filtrate was then neutralized with pyruvic acid 1/100 at pH 7.0±0.2 (pH: 7.08 adjusted with 3 mL of pyruvic acid 1/100), then sterilized under biosafety cabinet using a filtration with PES 0.2 µm sterilizing membrane.

A sample corresponding to the neutralized filtrate at the end of the process (called "process 5-E3-neutralized filtrate (pyruvic acid)", OM314C) was carried out at this step.

At the same time, the second part of the filtrate was subdivided into 9 equal parts. Each of these parts was then neutralized at 7.0±0.2 with hydrochloric 0.25% (pH: 7.09) or with organic acids (OM314C): formic 1/100 (pH: 7.11), acetic 1/100 (pH: 6.97), 3-hydroxy-butanoic 1/100 (pH:

7.03), aspartic 0.1% (pH: 7.09), lactic 1/100 (pH: 7.15), glutamic 0.1% (pH: 7.10), propionic 1/100 (pH: 7.10), pure ascorbic (pH: 7.04)). Finally, the different products were sterilized under biosafety cabinet using a filtration with PES 0.2 μm sterilizing membrane.

A sample corresponding to the different neutralized filtrates at the end of the process (called "process 5—E4-neutralized filtrate (name of acid)") was carried out at this step.

TABLE 8

Sample codes summary:

| | |
|---|---|
| Lysate | Process 5-E1-lysate |
| Filtrate | Process 5-E2-Filtrate |
| Standard Neutralized Filtrate | Process 5-E3-neutralized filtrate (pyruvic acid) |
| Acid 1 neutralized Filtrate | Process 5-E4- neutralized filtrate (hydrochloric acid) |
| Acid 2 neutralized Filtrate | Process 5-E4- neutralized filtrate (formic acid) |
| Acid 3 neutralized Filtrate | Process 5-E4- neutralized filtrate (acetic acid) |
| Acid 4 neutralized Filtrate | Process 5-E4- neutralized filtrate (3-hydroxy-butanoic acid) |
| Acid 5 neutralized Filtrate | Process 5-E4- neutralized filtrate (aspartic acid) |
| Acid 6 neutralized Filtrate | Process 5-E4- neutralized filtrate (lactic acid) |
| Acid 7 neutralized Filtrate | Process 5-E4- neutralized filtrate (glutamic acid) |
| Acid 8 neutralized Filtrate | Process 5-E4- neutralized filtrate (propionic acid) |
| Acid 9 neutralized Filtrate | Process 5-E4- neutralized filtrate (ascorbic acid) |

Example 1.7.2. Analytical Characterization

Analytical methods are described in 1.6.2
Analytical Characterization of Process 5 Final Samples at Release (T0)

E2-Filtrate solutions were frozen after process and were thawed at 4° C. overnight before

TABLE 9

Process 5-Analytical results

| Test | Sample | Result | Unit |
|---|---|---|---|
| Dry weight (total) | Process 5-E1-lysate | 11.6 | [mg/g] |
| Dry weight (supernatant) | Process 5-E1-lysate | 12.0 | [mg/g] |
| Dry weight (filtrate) | Process 5-E2-Filtrate | 8.0 | [mg/g] |
| Proteins total | Process 5-E2-Filtrate | 5.9 | [mg/mL] |
| Sugar total | Process 5-E2-Filtrate | 0.19 | [mg/mL] |
| Endotoxin LAL* | Process 5-E3-neutralized filtrate (pyruvic acid) | ND | [EU/mL] |
| DNA** | Process 5-E3-neutralized filtrate (pyruvic acid) | 13.2 | [μg/mL] |
| RNA*** | Process 5-E3-neutralized filtrate (pyruvic acid) | 6.9 | [μg/mL] |

ND = not detected;
*Endotoxin LAL: limit of detection = 0.1 EU/mL;
**DNA: limit of detection = 3.60 μg/mL, limit of quantification = 12.01 μg/mL;
***RNA: limit of detection = 4.29 μg/mL, limit of quantification = 14.32 μg/mL

TABLE 10

Process 5-Total Amino Acids after HCl hydrolysis

| Amino Acid | Concentration (μmol/mL) | %/AA (D vs L) |
|---|---|---|
| L-Asp | 0.74 | 62 |
| D-Asp | 0.46 | 38 |
| L-Glu | 1.17 | 69 |
| D-Glu | 0.52 | 31 |
| L-Ser | 0.29 | 51 |
| D-Ser | 0.28 | 49 |
| L-Thr | 0.44 | 14 |
| D-Thr | 2.69 | 86 |
| L-His | 0.00 | 0 |
| Gly | 0.21 | NA |
| D-His | 0.19 | 100 |
| L-Ala | 1.26 | NA |
| L-Arg | 0.94 | NA |
| D-Arg + D-Ala | 0.43 | NA |
| L-Tyr | 0.51 | 76 |
| D-Tyr | 0.16 | 24 |
| L-Val | 0.83 | 84 |
| L-Met | 0.31 | 100 |
| D-Met | 0.00 | 0 |
| L-Cys | 0.11 | NA |
| D-Val | 0.16 | 16 |
| L-Ile | 0.44 | 100 |
| L-Phe | 0.70 | 66 |
| D-Phe | 0.36 | 34 |
| L-Leu | 1.53 | 91 |
| D-Ile | 0.00 | 0 |
| D-Leu | 0.16 | 9 |
| L-Lys | 0.85 | 83 |
| D-Lys | 0.18 | 17 | a) Spectrophotometric Results Obtained During Stability

TABLE 11

Process 5-stability of solution through absorbance measurement

| Time points (Months) | Process 5 | | Pyruvic Acid | Hydrocloric Acid | Aspartic Acid | Formic Acid | Lactic Acid | 3-hydroxi-butanoic Acid | Ascorbic Acid | Acétic Acid | Propanoïc Acid | Glutamic Acid | HCL Industrial Batch 1619064 |
|---|---|---|---|---|---|---|---|---|---|---|---|---|---|
| T0 | | Abs [AU] | 1.668 | 1.559 | 1.273 | 1.634 | 1.567 | 1.591 | 1.602 | 1.59 | 1.847 | 1.394 | 2.865 |
| | | Evaluation | smooth | smooth | smooth | smooth | smooth | smooth | smooth | smooth | smooth | smooth | noisy |
| T1 | 4° C. | Abs [AU] | 1.687 | 1.592 | 1.259 | 1.622 | 1.589 | 1.589 | 2.262 | 1.599 | 1.605 | 1.405 | 3.17 |
| | | R (%) | 101% | 102% | 99% | 99% | 101% | 100% | 141% | 101% | 87% | 101% | 111% |
| | | Evaluation | smooth | smooth | smooth | smooth | smooth | smooth | noisy | smooth | smooth | smooth | noisy |
| | RT | Abs [AU] | 1.679 | 1.565 | 1.265 | 1.631 | 1.602 | 1.598 | 2.868 | 1.595 | 1.597 | 1.397 | 3.17 |
| | | R(%) | 101% | 100% | 99% | 100% | 102% | 100% | 179% | 100% | 86% | 100% | 111% |
| | | Evaluation | smooth | smooth | smooth | smooth | smooth | smooth | noisy | smooth | smooth | smooth | noisy |

TABLE 11-continued

Process 5-stability of solution through absorbance measurement

| Time points (Months) | | Process 5 | Pyruvic Acid | Hydrocloric Acid | Aspartic Acid | Formic Acid | Lactic Acid | 3-hydroxi-butanoic Acid | Ascorbic Acid | Acétic Acid | Propanoïc Acid | Glutamic Acid | HCL Industrial Batch 1619064 |
|---|---|---|---|---|---|---|---|---|---|---|---|---|---|
| T3 | 4° C. | Abs [AU] | 1.694 | 1.64 | 1.295 | 1.643 | 1.61 | 1.601 | 2.466 | 1.592 | 1.649 | 1.408 | 3.148 |
| | | R (%) | 102% | 105% | 102% | 101% | 103% | 101% | 154% | 100% | 89% | 101% | 110% |
| | | Evaluation | smooth | smooth | smooth | smooth | smooth | smooth | noisy | smooth | smooth | smooth | noisy |
| | RT | Abs [AU] | 1.693 | 1.601 | 1.285 | 1.655 | 1.62 | 1.622 | 3.094 | 1.657 | 1.63 | 1.433 | 3.159 |
| | | R (%) | 101% | 103% | 101% | 101% | 103% | 102% | 193% | 104% | 88% | 103% | 110% |
| | | Evaluation | smooth | smooth | smooth | smooth | smooth | smooth | noisy | smooth | smooth | smooth | noisy |
| T6 | 4° C. | Abs [AU] | 1.665 | 1.559 | 1.243 | 1.607 | 1.569 | 1.563 | 2.642 | 1.576 | 1.565 | 1.376 | 3.046 |
| | | R (%) | 100% | 100% | 98% | 98% | 100% | 98% | 165% | 99% | 85% | 99% | 106% |
| | | Evaluation | smooth | smooth | smooth | smooth | smooth | smooth | noisy | smooth | smooth | smooth | noisy |
| | RT | Abs [AU] | 1.707 | 1.657 | 1.337 | 1.728 | 1.672 | 1.691 | 2.964 | 1.683 | 1.686 | 1.427 | 2.985 |
| | | R (%) | 102% | 106% | 105% | 106% | 107% | 106% | 185% | 106% | 91% | 102% | 104% |
| | | Evaluation | smooth | smooth | smooth | smooth | smooth | smooth | noisy | smooth | smooth | smooth | noisy |

Abs: absorbance at 320 nm; RT: room temperature (20° C. +/− 5° C.); Evaluation: visual evaluation of the spectrum Industrial Batch 1619064 described in WO 2008/109669 OM-13-BV) was neutralized with hydrochloric acid presented precipitate starting at T0.

Except for ascorbic acid, Process 5—E4—neutralized filtrates were physically stable at 4° C. or room temperature for at least 6 months. They are considered as stable in those conditions for 12 months.

Figure 32:
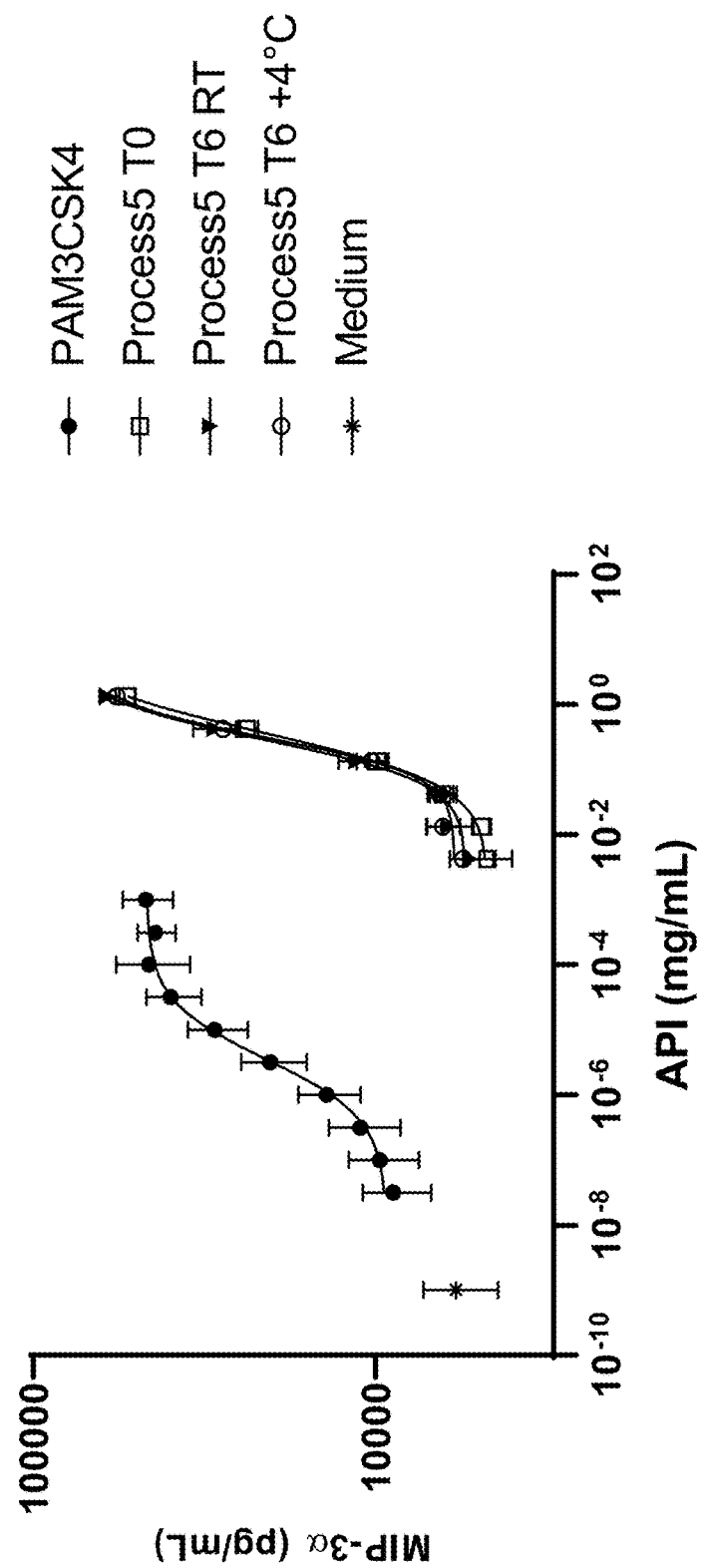
FIG. 32: Process 5—bioassay results during stability shows that Process 5—E3—neutralized filtrate (OM314A) exhibited a comparable bioactivity through MIP-3α secretion on THP-1 during at least 5 months at room temperature (20° C.+/−5° C.) or 4° C. Process 5 T0 was compared to T5 samples stored at 4° C. and at room temperature (RT) for 4 months.

Mip3-Alpha (CCL20) Results Obtained During Stability:

FIG. 32: Process 5—bioassay results during stability shows that Process 5—E3—neutralized filtrate exhibited a comparable bioactivity through MIP-3α secretion on THP-1 during at least 5 months at room temperature (20° C.+/−5° C.) or 4° C. Process 5 T0 was compared to T5 samples stored at 4° C. and at room temperature (RT) for 4 months.

Example 1.8 Process 3: *Streptococcus* pn. 7466 Alkaline Lysate (OM314A)

Example 1.8.1 Process 3: *Streptococcus* pn. 7466

Alkaline Lysis: 2794 kg of *Streptococcus pneunomiae* 7466 biomass (batch 1418123—boxes 34 and 35) were thawed overnight at room temperature in a lysis barrel. 240 g of NaOH 10 N and 4293 g of NaCl solution at 8 g/L were added to have a total weight of lysis of 7327 g. The alkaline lysis was transferred in a 37° C.±2.5° C. warm room under stirring 150 rpm±5 rpm for 8 days. After 3 h 00±30 min of lysis, the J0 OD was controlled. The sample was diluted 100 times and read with a spectrophotometer at 700 nm (read OD: 0.258 and final OD: 25.8). Each working day, the stirring (150 rpm±5 rpm), the warm room temperature (37.0° C.±2.5° C.) and the pH were controlled (J1 pH: 12.63/J2 pH: 12.62/J5 pH: 12.59/J6 pH: 12.65/J7 pH: 12.69/J8 pH: 12.71). If the pH did not enter into the process range, an adjustment with NaOH 10 N had to be perform (J1: 10 mL of NaOH 10 N/J2: 10 mL of NaOH 10 N/J5: 10 mL of NaOH 10 N/J6: 10 mL of NaOH 10 N/J7: 10 mL of NaOH 10 N).

At the end of the lysis, the J8 OD was controlled. The sample was diluted 5 times and read with a spectrophotometer at 700 nm (read OD: 0.092 and final OD: 0.46). The delta OD between J0 and J8 had to be superior to 12.8 (Delta OD: 25.34).

A part of this *Streptococcus pneunomiae* 7466 lysis was recovered and was stored in a 2500 mL mini-cask (reference: Semadeni no 6863). A sample corresponding to the lysate at the end of the lysis (called "process 3-E1-lysate") was carried out at this step.

Filtering 1: The installation for the filtration of the product was prepared in accordance with the diagram (FIG. 2). The filtration system consists of 2 filtration loops. A first microfiltration (called MF) consisting of a tank (vessel 2 on FIG. 2), a pump (pump 1 on FIG. 2) and a filtration system with a cut-off point of 0.45 μm (micro-filter on FIG. 2). The second loop, ultrafiltration (called UF), consists of a tank (vessel 3 on FIG. 2), a pump (pump 2 on FIG. 2) and a filtration system with a cut-off point of 10 kDa (ultrafiltration filter on FIG. 2). The filtration took place at the laboratory scale with an implemented volume of 2000 mL.

Before starting the process, we had to ensure that the filtration system was reproducible over batches. To verify the correct filterability of the product, an NWP (Normalized Water Permeability) was performed on the filtration system. The lysate used for the production was first diluted 2 times with purified water (1000.0 g of lysate and 1000.0 g of purified water). The product was stirred to have a product vortex of 1 cm. The temperature of the product was cooled to room temperature while waiting the filtering process to start. In this process there was a pH adjustment at pH 10.5-10.8 (pH: 10.68 adjusted with 15 mL of pure 3-hydroxy-butanoic acid).

Initial concentration: The product used for the first step of filtration had the following parameters (pH: 10.68), temperature 29° C., stirred to have a product vortex of 1 cm). The MF loop pump (pump 1 on FIG. 2) was started at 40% of the process speed to charge the system with the product. Once this step was completed, the recirculation of the product on the MF loop started and the pump speed was increased regularly to reach 75% of the process speed. Recirculation allows the hydrophilic filtration system to be conditioned by eliminating the air bubbles present in the system.

When the flow rate and the pressure were stable, the filtration system was considered as conditioned. Then, the permeate valve of the MF loop was opened in order to perform an initial concentration of the product with a concentration factor to 0.5 (pressure input: 210 mbar, permeate flow rate: 50 mL/min). During the initial concentration, the pump (pump 1 on FIG. 2) speed was gradually increased to 100% (100 rpm corresponding to 600 mL/min) of the process speed.

Parallel to this step, the UF loop was conditioned. The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Diafiltration: When the 0.5 concentration factor was reached, the UF permeate was opened in order to start the diafiltration of the product (pressure input: 680 mbar, permeate flow rate: 47 mL/min). In order to have an optimal extraction of the product, the MF TMP (Trans Membrane Pressure) which was controlled by valve 1 on FIG. 2, must be set at 850 mbar (pressure input: 995 mbar, permeate flow rate: 46 mL/min). During the diafiltration, the speed of the UF pump (pump 2 on FIG. 2) was set to reach an UF permeate flow equal to the permeate flow MF. Indeed, the volume on the MF tank (vessel 2 on FIG. 2) had to remain as stable as possible during the diafiltration step.

The diafiltration was performed by cycle. At the end of the initial concentration, there was a volume present in the MF tank (vessel 2 on FIG. 2). Once this volume passed through the MF filtration system, one cycle was realized. In this process, the diafiltration needed 5 cycles.

Final concentration: At the end of the 5 diafiltration cycles, the UF pump was stopped. When the MF input pressure started to increase, the MF pump was shut down. At the end of this first filtration step, the product of interest contained elements smaller than 0.45 μm in size.

Filtering 2: The product of interest harvested (mass: 945.7 g) then undergone a second stage of 5 cycles purification on the UF loop with cut-off point 10 kDa (vessel 3, pump 2 and ultrafiltration filter on FIG. 2). The permeate was waste as mentioned on FIG. 2. The constant volume was maintained during this second filtering step of purification, by adding of NaOH 0.001 N solution at pH 10.0.

The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Once the filtration system conditioned, the UF permeate was opened in order to start the filtering 2 of the product (pressure input: 690 mbar, permeate flow rate: 37 mL/min). In order to have an optimal extraction of the product, the UF TMP (Trans Membrane Pressure) which was controlled by valves 2 and 3 on FIG. 2, must be set at 850 mbar (pressure input: 945 mbar, permeate flow rate: 52 mL/min).

During the filtering 2 step, the volume on the UF tank (vessel 3 on FIG. 2) had to remain as stable as possible. So, as the level of the UF tank (vessel 3 on FIG. 2) decreased, there was an addition of NaOH solution. The 5 cycles corresponding to a volume of NaOH solution added equivalent to 5 times the volume of product of interest harvested.

At the end of filtering 2 step, the final product was harvested (mass: 931.7 g), and then separated into 2 equal parts. At the end of this second filtration step, the product of interest contained elements smaller than 0.45 μm and taller than 10 kDa in size.

A sample corresponding to the filtrate before neutralization (called "process 3-E2-filtrate") was carried out at this step.

The first part of the filtrate was then neutralized with 3-hydroxy-butanoic acid 1/100 at pH 7.2 0.2 (pH: 7.25 adjusted with 10 mL of 3-hydroxy-butanoic acid 1/100), then sterilized under biosafety cabinet using a filtration with PES 0.2 μm sterilizing membrane.

A sample corresponding to the neutralized filtrate at the end of the process (called "process 3-E3-neutralized filtrate (3-hydroxy-butanoic acid)") was carried out at this step.

At the same time, the second part of the filtrate was subdivided into 9 equal parts. Each of these parts was then neutralized at 7.2±0.2 with hydrochloric 2.5% (pH: 7.19) or with organic acids (OM314A): formic 1/100 (pH: 7.16), acetic 1/100 (pH: 7.16), pyruvic 1/100 (pH: 7.14), aspartic 1/100 (pH: 7.19), lactic 1/100 (pH: 7.06), glutamic 0.1% (pH: 7.13), propionic 1/100 (pH: 7.20), pure ascorbic (pH: 7.20)). Finally, the different products were sterilized under biosafety cabinet using a filtration with PES 0.2 μm sterilizing membrane.

A sample corresponding to the different neutralized filtrates at the end of the process (called "process 3—E4-neutralized filtrate (name of acid)") was carried out at this step.

TABLE 12

| Sample with codes, summary: | |
|---|---|
| Lysate | Process 3-E1-lysate |
| Filtrate | Process 3-E2-Filtrate |
| Standard NeutralizedFiltrate | Process 3-E3-neutralized filtrate (3-hydroxy-butanoic acid) |
| Acid 1 neutralized Filtrate | Process 3-E4-neutralized filtrate (hydrochloric acid) |
| Acid 2 neutralized Filtrate | Process 3-E4-neutralized filtrate (formic acid) |
| Acid 3 neutralized Filtrate | Process 3-E4-neutralized filtrate (acetic acid) |
| Acid 4 neutralized Filtrate | Process 3-E4-neutralized filtrate (pyruvic acid) |
| Acid 5 neutralized Filtrate | Process 3-E4-neutralized filtrate (aspartic acid) |
| Acid 6 neutralized Filtrate | Process 3-E4-neutralized filtrate (lactic acid) |
| Acid 7 neutralized Filtrate | Process 3-E4-neutralized filtrate (glutamic acid) |
| Acid 8 neutralized Filtrate | Process 3-E4-neutralized filtrate (propionic acid) |
| Acid 9 neutralized Filtrate | Process 3-E4-neutralized filtrate (ascorbic acid) |

Example 1.8.2 Analytical Characterization

Analytical methods are described in 1.6.2

Analytical Characterization of Process 3 Final Samples at Release (T0)

E2-Filtrate solutions were frozen after process and were thawed at 4° C. overnight before analysis. Results at release (T0):

TABLE 13

| Test | Sample | Result | Unit |
|---|---|---|---|
| Dry weight (total) | Process 3-E1-lysate | 38.0 | [mg/g] |
| Dry weight (supernatant) | Process 3-E1-lysate | 38.8 | [mg/g] |
| Dry weight (filtrate) | Process 3-E2-Filtrate | 12.1 | [mg/g] |
| Proteins total | Process 3-E2-Filtrate | 9.9 | [mg/mL] |
| Sugar total | Process 3-E2-Filtrate | 0.67 | [mg/mL] |
| Endotoxin LAL* | Process 3-E3-neutralized filtrate (3-hydroxy-butanoic acid) | ND | [EU/mL] |
| DNA** | Process 3-E3-neutralized filtrate (3-hydroxy-butanoic acid) | 9.5 | [µg/mL] |
| RNA*** | Process 3-E3-neutralized filtrate (3-hydroxy-butanoic acid) | ND | [µg/mL] |

ND = not detected;
*Endotoxin LAL: limit of detection = 0.1 EU/mL;
**DNA: limit of detection = 3.60 µg/mL, limit of quantification = 12.01 µg/mL;
***RNA: limit of detection = 4.29 µg/mL, limit of quantification = 14.32 µg/mL.

TABLE 14

Process 3-Total Amino Acids after HCl hydrolysis

| Amino Acid | Concentration (µmol/mL) | %/AA (D vs L) |
|---|---|---|
| L-Asp | 1.39 | 53 |
| D-Asp | 1.25 | 47 |
| L-Glu | 2.11 | 59 |
| D-Glu | 1.44 | 41 |
| L-Ser | 0.33 | 48 |
| D-Ser | 0.36 | 52 |
| L-Thr | 0.56 | 13 |
| D-Thr | 3.71 | 87 |
| L-His | 0.00 | 0 |
| Gly | 0.46 | NA |
| D-His | 0.24 | 100 |
| L-Ala | 2.00 | NA |
| L-Arg | 1.00 | NA |
| D-Arg + D-Ala | 0.80 | NA |
| L-Tyr | 0.66 | 68 |
| D-Tyr | 0.31 | 32 |
| L-Val | 1.74 | 89 |
| L-Met | 0.42 | 100 |
| D-Met | 0.00 | 0 |
| L-Cys | 0.21 | NA |
| D-Val | 0.22 | 11 |
| L-Ile | 0.80 | 76 |
| L-Phe | 1.38 | 69 |
| D-Phe | 0.62 | 31 |
| L-Leu | 2.30 | 81 |
| D-Ile | 0.25 | 24 |
| D-Leu | 0.53 | 19 |
| L-Lys | 1.68 | 72 |
| D-Lys | 0.65 | 28 | a) Spectrophotometric Results Obtained During Stability

TABLE 15

Process 3-stability of solution through absorbance measurement

| Time points (Months) | Process 3 | | 3-hydroxi-butanoic Acid | Hydrocloric Acid | Aspartic Acid | Formic Acid | Lactic Acid | Propionic Acid | Ascorbic Acid | Acetic Acid | Pyruvic Acid | Glutamic Acid | HCL Industrial Batch 1619013 |
|---|---|---|---|---|---|---|---|---|---|---|---|---|---|
| T0 | | Abs [AU] | 1.105 | 1.056 | 0.74 | 1.125 | 1.087 | 1.099 | 1.267 | 1.142 | 1.258 | 0.888 | 3.038 |
| | | Evaluation | smooth | smooth | smooth | smooth | smooth | smooth | smooth | smooth | smooth | smooth | noisy |
| T1 | 4° C. | Abs [AU] | 1.087 | 1.064 | 1.151 | 1.114 | 1.117 | 1.119 | 2.049 | 1.128 | 1.294 | 0.898 | 3.196 |
| | | R (%) | 98% | 101% | 156% | 99% | 103% | 102% | 162% | 99% | 103% | 101% | 105% |
| | | Evaluation | smooth | smooth | smooth | smooth | smooth | smooth | noisy | smooth | smooth | smooth | noisy |
| | RT | Abs [AU] | 1.134 | 1.121 | 0.757 | 1.17 | 1.143 | 1.165 | 3.488 | 1.243 | 1.372 | 0.951 | 3.033 |
| | | R (%) | 103% | 106% | 102% | 104% | 105% | 106% | 275% | 109% | 109% | 107% | 100% |
| | | Evaluation | smooth | smooth | smooth | smooth | smooth | smooth | noisy | smooth | smooth | smooth | noisy |
| T3 | 4° C. | Abs [AU] | 1.104 | 1.112 | 0.738 | 1.166 | 1.124 | 1.141 | 3.302 | 1.155 | 1.316 | 0.891 | 3.127 |
| | | R (%) | 100% | 105% | 100% | 104% | 103% | 104% | 261% | 101% | 105% | 100% | 103% |
| | | Evaluation | smooth | smooth | smooth | smooth | smooth | smooth | noisy | smooth | smooth | smooth | noisy |
| | RT | Abs [AU] | 1.165 | 1.162 | 1.235 | 1.223 | 1.179 | 1.219 | 3.445 | 1.229 | 1.388 | 0.948 | 3.127 |
| | | R (%) | 105% | 110% | 167% | 109% | 108% | 111% | 272% | 108% | 110% | 107% | 103% |
| | | Evaluation | smooth | smooth | smooth | smooth | smooth | smooth | noisy | smooth | smooth | smooth | noisy |

Figure 31:
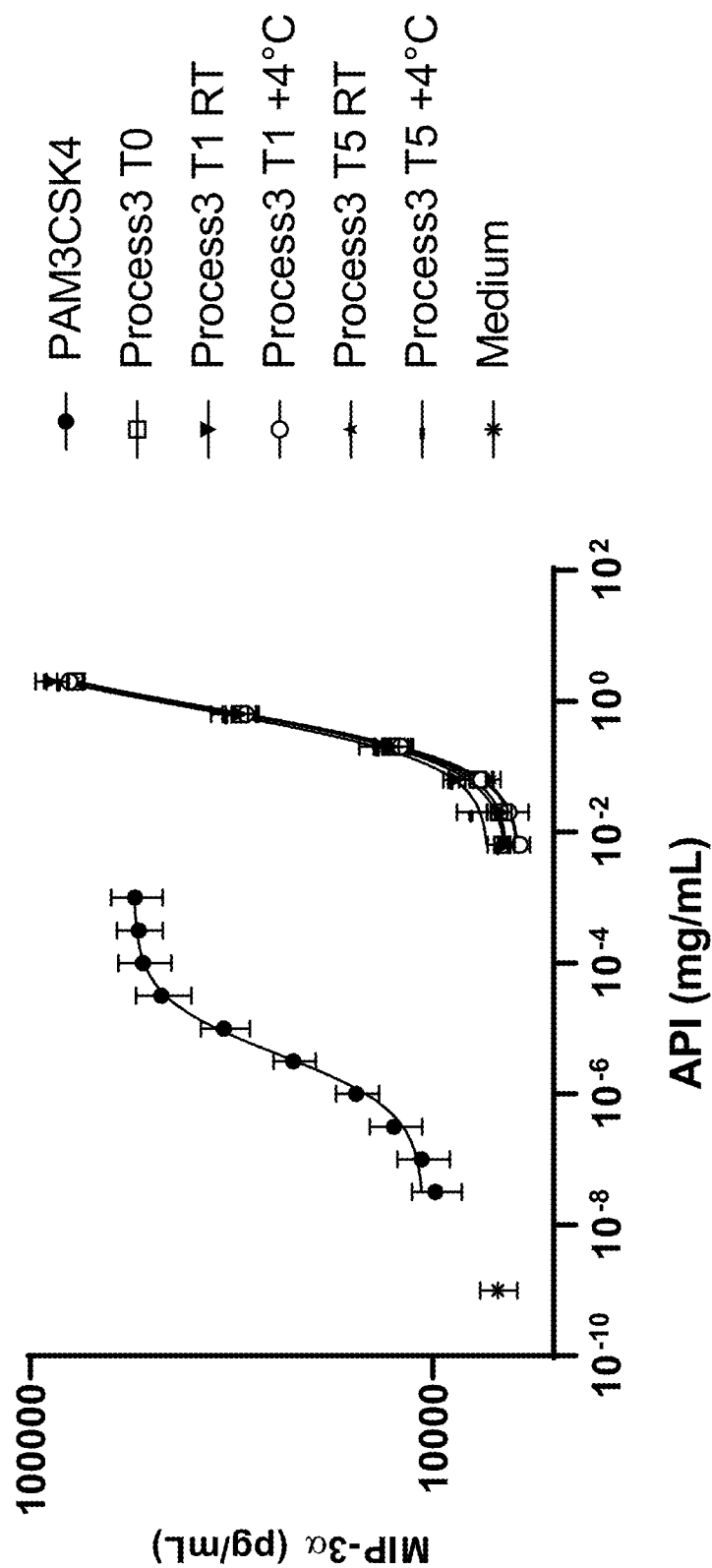
FIG. 31: Process 3—bioassay results during stability shows that Process 3—E3—neutralized filtrate (OM314A) exhibited a comparable bioactivity through MIP-3α secretion on THP-1 during at least 5 months at room temperature (20° C.+/−5° C.) or 4° C. Process 3 T0 was compared to T5 samples stored at 4° C. and at room temperature (RT) for 5 month.

Abs: absorbance at 320 nm; RT: room temperature (20° C. +/− 5° C.); Evaluation: visual evaluation of the spectrum Industrial Batch 1619064 described in WO 2008/109669 was neutralized with hydrochloric acid and presented precipitate starting at TO. Except for ascorbic acid, Process 3—E4—neutralized filtrates were physically stable at 4° C. or room temperature for at least 3 months.

b) Mip3-Alpha (CCL20) Results Obtained During Stability:

FIG. 31: Process 3—bioassay results during stability shows that Process 3—E3—neutralized filtrate exhibited a comparable bioactivity through MIP-3α secretion on THP-1 during at least 5 months at room temperature (20° C.+/−5° C.) or 4° C. Process 3 TO was compared to T5 samples stored at 4° C. and at room temperature (RT) for 5 months.

Example 1.9, 21 Strain Polylysate Stable Bacterial Extract OM314A)

Example 1.9.1 Process 1 for Stabilizing a 21 Strain Polylysate Bacterial Extract Formulation Lysis: A part of 21 strain polylysate was recovered in production and was stored in a 2500 mL mini-cask (reference: Semadeni no 6863).

A sample corresponding to the lysate at the end of the lysis (called "process 1-E1-lysate") was carried out at this step.

Filtering 1: The installation for the filtration of the product was prepared in accordance with the diagram (FIG. 2). The filtration system consists of 2 filtration loops. A first microfiltration (called MF) consisting of a tank (vessel 2 on FIG. 2), a pump (pump 1 on FIG. 2) and a filtration system with a cut-off point of 0.45 μm (micro-filter on FIG. 2). The second loop, ultrafiltration (called UF), consists of a tank (vessel 3 on FIG. 2), a pump (pump 2 on FIG. 2) and a filtration system with a cut-off point of 10 kDa (ultrafiltration filter on FIG. 2). The filtration took place at the laboratory scale with an implemented volume of 2000 mL.

Before starting the process, we had to ensure that the filtration system was reproducible over batches. To verify the correct filterability of the product, an NWP (Normalized Water Permeability) was performed on the filtration system.

The lysate used for the production was first diluted 2 times with purified water (1000.6 g of lysate and 999.9 g of purified water). The product was stirred to have a product vortex of 1 cm. The temperature of the product was cooled to room temperature while waiting the filtering process to start. In this process there was a pH adjustment at pH 10.5-10.8 (pH: 10.77 adjusted with pure aspartic acid).

Initial concentration: The product used for the first step of filtration had the following parameters (pH: 10.77), temperature 25° C., stirred to have a product vortex of 1 cm). The MF loop pump (pump 1 on FIG. 2) was started at 40% of the process speed to charge the system with the product. Once this step was completed, the recirculation of the product on the MF loop started and the pump speed was increased regularly to reach 75% of the process speed. Recirculation allows the hydrophilic filtration system to be conditioned by eliminating the air bubbles present in the system.

When the flow rate and the pressure were stable, the filtration system was considered as conditioned. Then, the permeate valve of the MF loop was opened in order to perform an initial concentration of the product with a concentration factor to 0.5 (pressure input: 300 mbar, permeate flow rate: 43 mL/min). During the initial concentration, the pump (pump 1 on FIG. 2) speed was gradually increased to 100% (100 rpm corresponding to 600 mL/min) of the process speed.

Parallel to this step, the UF loop was conditioned. The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Diafiltration: When the 0.5 concentration factor was reached, the UF permeate was opened in order to start the diafiltration of the product (pressure input: 730 mbar, permeate flow rate: 58 mL/min). In order to have an optimal extraction ofthe product, the MF TMP (Trans Membrane Pressure) which was controlled by valve 1 on FIG. 2, must be set at 850 mbar (pressure input: 1010 mbar, permeate flow rate: 58 mL/min).

During the diafiltration, the speed of the UF pump (pump 2 on FIG. 2) was set to reach an UF permeate flow equal to the permeate flow MF. Indeed, the volume on the MF tank (vessel 2 on FIG. 2) had to remain as stable as possible during the diafiltration step.

The diafiltration was performed by cycle. At the end of the initial concentration, there was a volume present in the MF tank (vessel 2 on FIG. 2). Once this volume passed through the MF filtration system, one cycle was realized. In this process, the diafiltration needed 5 cycles.

Final concentration: At the end of the 5 diafiltration cycles, the UF pump was stopped. When the MF input pressure started to increase, the MF pump was shut down. At the end of this first filtration step, the product of interest contained elements smaller than 0.45 μm in size.

Filtering 2: The product of interest harvested (mass: 1232.7 g) then undergone a second stage of 5 cycles purification on the UF loop with cut-off point 10 kDa (vessel 3, pump 2 and ultrafiltration filter on FIG. 2). The permeate was waste as mentioned on FIG. 2. The constant volume was maintained during this second filtering step of purification, by adding of NaOH 0.001 N solution at pH 10.0.

The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Once the filtration system conditioned, the UF permeate was opened in order to start the filtering 2 of the product (pressure input: 655 mbar, permeate flow rate: 37 mL/min). In order to have an optimal extraction of the product, the UF TMP (Trans Membrane Pressure) which was controlled by valves 2 and 3 on FIG. 2, must be set at 850 mbar (pressure input: 917 mbar, permeate flow rate: 57 mL/min).

During the filtering 2 step, the volume on the UF tank (vessel 3 on FIG. 2) had to remain as stable as possible. So, as the level of the UF tank (vessel 3 on FIG. 2) decreased, there was an addition of NaOH solution. The 5 cycles corresponding to a volume of NaOH solution added equivalent to 5 times the volume of product of interest harvested.

At the end of filtering 2 step, the final product was harvested (mass: 1237.0 g), and then separated into 2 equal parts. At the end of this second filtration step, the product of interest contained elements smaller than 0.45 μm and taller than 10 kDa in size.

A sample corresponding to the filtrate before neutralization (called "process 1-E2-filtrate") was carried out at this step.

The first part of the filtrate was then neutralized with aspartic acid 0.1% at pH 7.2±0.2 (pH: 7.20 adjusted with 65 mL of aspartic acid 0.1%), then sterilized under biosafety cabinet using a filtration with PES 0.2 μm sterilizing membrane.

A sample corresponding to the neutralized filtrate at the end of the process (called "process 1-E3-neutralized filtrate (aspartic acid)" OM314A) was carried out at this step.

At the same time, the second part of the filtrate was subdivided into 9 equal parts. Each of these parts was then neutralized at 7.2±0.2 with hydrochloric 0.25% (pH: 7.19) or with organic acids (OM314A): formic 1/100 (pH: 7.16), acetic 1/100 (pH: 7.20), pyruvic 1/100 (pH: 7.12), 3-hydroxy-butanoic 1/100 (pH: 7.17), lactic 1/100 (pH: 7.19), glutamic 0.1% (pH: 7.09), propionic 1/100 (pH: 7.11), pure ascorbic (pH: 7.20)). Finally, the different products were sterilized under biosafety cabinet using a filtration with PES 0.2 μm sterilizing membrane.

A sample corresponding to the different neutralized filtrates at the end of the process (called "process 1—E4-neutralized filtrate (name of acid)", OM314A) was carried out at this step.

TABLE 16

Sample summary:

| | |
|---|---|
| Lysate | Process 1-E1-lysate |
| Filtrate | Process 1-E2-Filtrate |
| Standard Neutralized Filtrate | Process 1-E3-neutralized filtrate (aspartic acid) |
| Acid 1 neutralized Filtrate | Process 1-E4-neutralized filtrate (hydrochloric acid) |
| Acid 2 neutralized Filtrate | Process 1-E4-neutralized filtrate (formic acid) |
| Acid 3 neutralized Filtrate | Process 1-E4-neutralized filtrate (acetic acid) |
| Acid 4 neutralized Filtrate | Process 1-E4-neutralized filtrate (pyruvic acid) |
| Acid 5 neutralized Filtrate | Process 1-E4-neutralized filtrate (3-hydroxy-butanoic acid) |
| Acid 6 neutralized Filtrate | Process 1-E4-neutralized filtrate (lactic acid) |
| Acid 7 neutralized Filtrate | Process 1-E4-neutralized filtrate (glutamic acid) |
| Acid 8 neutralized Filtrate | Process 1-E4-neutralized filtrate (propionic acid) |
| Acid 9 neutralized Filtrate | Process 1-E4-neutralized filtrate (ascorbic acid) |

Example 1.9.2. Analytical Characterization

Analytical methods are described in 1.6.2 a) Results at Release:

E2-Filtrate solutions were frozen after process and were thawed at 4° C. overnight before analysis.

TABLE 17

Process 1-Analytical results

| Test | Sample | Result | Unit |
|---|---|---|---|
| Dry weight (total) | Process 1-E1-lysate | 31.3 | [mg/g] |
| Dry weight (supernatant) | Process 1-E1-lysate | 30.0 | [mg/g] |
| Dry weight (filtrate) | Process 1-E2-Filtrate | 9.1 | [mg/g] |
| Proteins total | Process 1-E2-Filtrate | 7.3 | [mg/mL] |
| Sugar total | Process 1-E2-Filtrate | 0.10 | [mg/mL] |
| Endotoxin LAL* | Process 1-E3-neutralized filtrate (aspartic acid) | ND | [EU/mL] |
| DNA** | Process 1-E3-neutralized filtrate (aspartic acid) | 10.4 | [μg/mL] |
| RNA*** | Process 1-E3-neutralized filtrate (aspartic acid) | ND | [μg/mL] |

ND = not detected;
*Endotoxin LAL: limit of detection = 0.1 EU/mL;
**DNA: limit of detection = 3.60 μg/mL, limit of quantification = 12.01 μg/mL;
***RNA: limit of detection = 4.29 μg/mL, limit of quantification = 14.32 μg/mL

TABLE 18

Process 1-Total Amino Acids after acid hydrolysis

| Amino Acid | Concentration (μmol/mL) | %/AA (D vs L) |
|---|---|---|
| L-Asp | 1.17 | 60 |
| D-Asp | 0.77 | 40 |
| L-Glu | 1.59 | 68 |
| D-Glu | 0.75 | 32 |
| L-Ser | 0.39 | 55 |
| D-Ser | 0.32 | 45 |
| L-Thr | 0.46 | 11 |
| D-Thr | 3.56 | 89 |
| L-His | 0.00 | 0 |
| Gly | 0.32 | NA |
| D-His | 0.35 | 100 |
| L-Ala | 1.71 | NA |
| L-Arg | 0.83 | NA |
| D-Arg + D-Ala | 0.50 | NA |
| L-Tyr | 0.61 | 77 |
| D-Tyr | 0.19 | 23 |
| L-Val | 1.23 | 90 |
| L-Met | 0.28 | 100 |
| D-Met | 0.00 | 0 |
| L-Cys | 0.11 | NA |
| D-Val | 0.13 | 10 |
| L-Ile | 0.61 | 77 |
| L-Phe | 1.03 | 73 |
| D-Phe | 0.38 | 27 |
| L-Leu | 1.83 | 88 |
| D-Ile | 0.19 | 23 |
| D-Leu | 0.26 | 12 |
| L-Lys | 1.82 | 81 |
| D-Lys | 0.42 | 19 |

Spectrophotometric Results Obtained During Stability

TABLE 19

Process 1-stability of solution through absorbance measurement

| Time points (Months) | | Process 1 | Aspartic Acid | Hydrocloric Acid | Propionic Acid | Formic Acid | Lactic Acid | 3-hydroxi-butanoic Acid | Ascorbic Acid | Acetic Acid | Pyruvic Acid | Glutamic Acid | *Industrial Batch 1619013 |
|---|---|---|---|---|---|---|---|---|---|---|---|---|---|
| T0 | | Abs [AU] | 1.317 | 1.496 | 1.54 | 1.553 | 1.519 | 1.509 | 1.646 | 1.504 | 1.638 | 1.294 | 2.73 |
| | | Evaluation | smooth | smooth | smooth | smooth | smooth | smooth | smooth | smooth | smooth | smooth | noisy |
| T1 | 4° C. | Abs [AU] | 1.329 | 1.496 | 1.552 | 1.574 | 1.53 | 1.528 | 2.144 | 1.543 | 1.66 | 1.325 | 3.032 |
| | | R (%) | 101% | 100% | 101% | 101% | 101% | 101% | 130% | 103% | 101% | 102% | 111% |
| | | Evaluation | smooth | smooth | smooth | smooth | smooth | smooth | noisy | smooth | smooth | smooth | noisy |
| | RT | Abs [AU] | 1.397 | 1.579 | 1.589 | 1.634 | 1.591 | 1.602 | 3.043 | 1.602 | 1.727 | 1.365 | 3.152 |
| | | R (%) | 106% | 106% | 103% | 105% | 105% | 106% | 185% | 107% | 105% | 105% | 115% |
| | | Evaluation | smooth | smooth | smooth | smooth | smooth | smooth | noisy | smooth | smooth | smooth | noisy |
| T3 | 4° C. | Abs [AU] | 1.397 | 1.587 | 1.574 | 1.599 | 1.545 | 1.532 | 2.457 | 1.603 | 1.692 | 1.347 | 3.441 |
| | | R (%) | 106% | 106% | 102% | 103% | 102% | 102% | 149% | 107% | 103% | 104% | 126% |
| | | Evaluation | smooth | smooth | smooth | smooth | smooth | smooth | noisy | smooth | smooth | smooth | noisy |
| | RT | Abs [AU] | 1.438 | 1.66 | 1.679 | 1.705 | 1.687 | 1.693 | 2.831 | 1.688 | 1.769 | 1.423 | 3.232 |
| | | R (%) | 109% | 111% | 109% | 110% | 111% | 112% | 172% | 112% | 108% | 110% | 118% |
| | | Evaluation | smooth | smooth | smooth | smooth | smooth | smooth | noisy | smooth | smooth | smooth | noisy |

Figure 29:
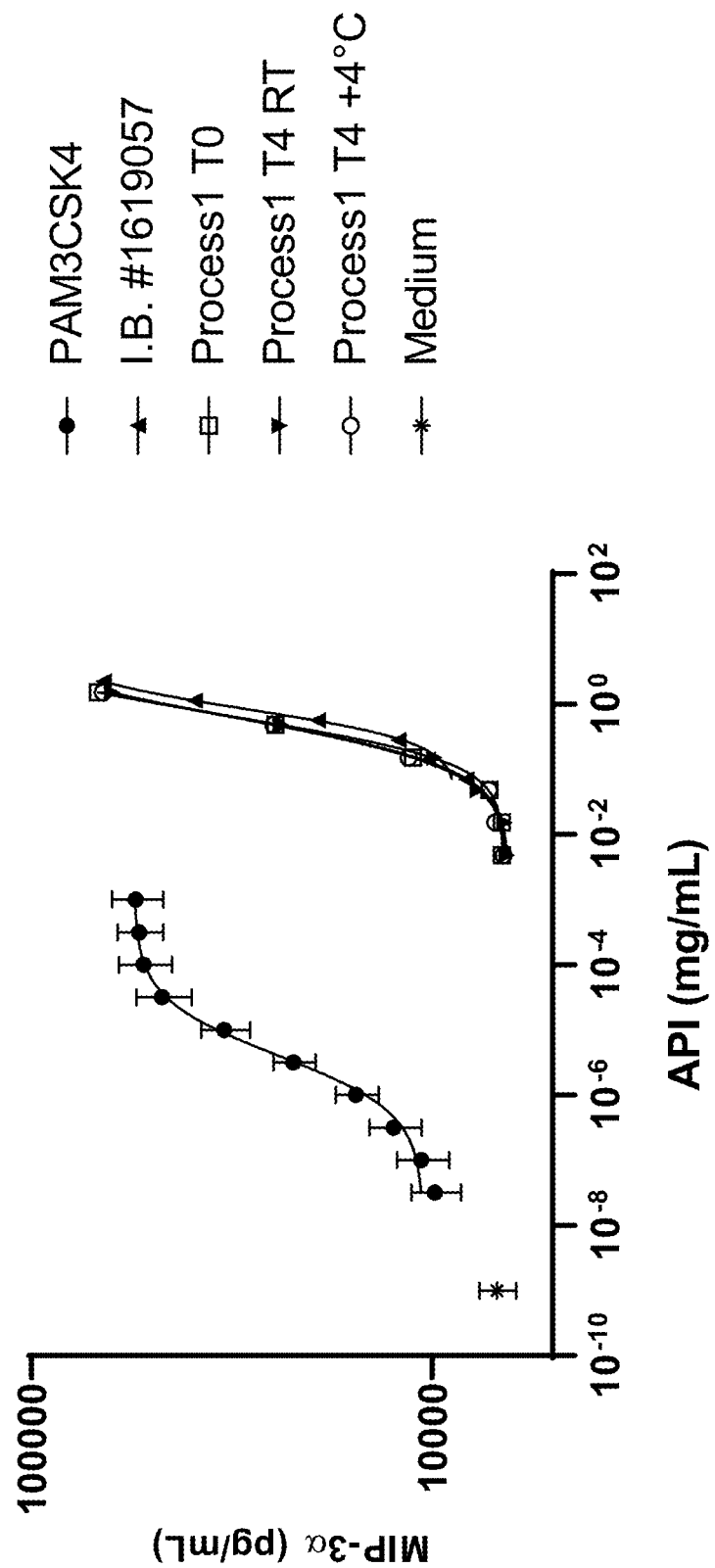
FIG. 29: Process 1—bioassay results during stability shows that Process 1—E3—neutralized filtrate (OM314A) exhibited a comparable bioactivity through MIP-3α secretion on THP-1 during at least 4 months at room temperature (20° C.+/−5° C.) or 4° C. Process 1 T0 was compared to T4 samples stored at 4° C. and at room temperature (RT) for 4 month.

Abs: absorbance at 320 nm; RT: room temperature (20° C. +/− 5° C.); Evaluation: visual evaluation of the spectrum Industrial Batch 1619064 described as 21 strain lysates in WO 2008/109669 was neutralized with hydrochloric acid and presented precipitate starting at T0. Except for ascorbic acid, Process 1—E4-neutralized filtrates were physically stable at 4° C. or room temperature for at least 3 months.

b) Mip3-Alpha (CCL20) Results Obtained During Stability:

FIG. 29: Process 1—bioassay results during stability shows that Process 1—E3—neutralized filtrate exhibited a comparable bioactivity through MIP-3α secretion on THP-1 during at least 4 months at room temperature (20° C.+/−5° C.) or 4° C. Process 1 T0 was compared to T4 samples stored at 4° C. and at room temperature (RT) for 4 months.

Example 1.9 *Haemophilus influenzae* 8467 (OM314A)

Example 1.10.1 Process 2: *Haemophilus influenzae* 8467

Lysis: 13396 kg of *Haemophilus* influenza 8467 biomass (batch 1419110—boxes 10, 11, 12 and 13) were thawed overnight at room temperature in a lysis barrel. 692 g of NaOH 10 N and 12920 g of NaCl solution at 8 g/L were added to have a total weight of lysis of 27008 g. The alkaline lysis was transferred in a 37° C.±2.5° C. warm room under stirring 150 rpm±5 rpm for 5 days. After 3 h 00±30 min of lysis, the J0 OD was controlled. The sample was diluted 200 times and read with a spectrophotometer at 700 nm (read OD: 0.273 and final OD: 54.6). Each working day, the stirring (150 rpm±5 rpm), the warm room temperature (37.0° C.±2.5° C.) and the pH were controlled (J1 pH: 11.87/J2 pH: 11.74/J5 pH: 11.45). If the pH did not enter into the process range, an adjustment with NaOH 10 N had to be perform (J1: 20 mL of NaOH 10 N/J2: 20 mL of NaOH 10 N). At the end of the lysis, the J8 OD was controlled. The sample was diluted 100 times and read with a spectrophotometer at 700 nm (read OD: 0.169 and final OD: 16.9). The delta OD between J0 and J5 had to be superior to 13.1 (Delta OD: 37.7). A part of this *Haemophilus* influenza 8467 lysis was recovered and was stored in a 2500 mL mini-cask (reference: Semadeni no 6863). A sample corresponding to the lysate at the end of the lysis (called "process 2-E1-lysate") was carried out at this step.

Filtering 1: The installation for the filtration of the product was prepared in accordance with the diagram (FIG. 2). The filtration system consists of 2 filtration loops. A first microfiltration (called MF) consisting of a tank (vessel 2 on FIG. 2), a pump (pump 1 on FIG. 2) and a filtration system with a cut-off point of 0.45 μm (micro-filter on FIG. 2). The second loop, ultrafiltration (called UF), consists of a tank (vessel 3 on FIG. 2), a pump (pump 2 on FIG. 2) and a filtration system with a cut-off point of 10 kDa (ultrafiltration filter on FIG. 2). The filtration took place at the laboratory scale with an implemented volume of 2000 mL.

Before starting the process, we had to ensure that the filtration system was reproducible over batches. To verify the correct filterability of the product, an NWP (Normalized Water Permeability) was performed on the filtration system.

The lysate used for the production was first diluted 4 times with purified water (499.9 g of lysate and 1500.2 g of purified water). The product was stirred to have a product vortex of 1 cm. The temperature of the product was cooled to room temperature while waiting the filtering process to start. In this process there was no pH adjustment, so the filtering process started immediately.

Initial concentration: The product used for the first step of filtration had the following parameters (pH: 11.23), temperature 32° C., stirred to have a product vortex of 1 cm). The MF loop pump (pump 1 on FIG. 2) was started at 40% of the process speed to charge the system with the product. Once this step was completed, the recirculation of the product on the MF loop started and the pump speed was increased regularly to reach 75% of the process speed. Recirculation allows the hydrophilic filtration system to be conditioned by eliminating the air bubbles present in the system.

When the flow rate and the pressure were stable, the filtration system was considered as conditioned. Then, the permeate valve of the MF loop was opened in order to perform an initial concentration of the product with a concentration factor to 0.5 (pressure input: 325 mbar, permeate flow rate: 45 mL/min). During the initial concentration, the pump (pump 1 on FIG. 2) speed was gradually increased to 100% (100 rpm corresponding to 600 mL/min) of the process speed.

Parallel to this step, the UF loop was conditioned. The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Diafiltration: When the 0.5 concentration factor was reached, the UF permeate was opened in order to start the diafiltration of the product (pressure input: 880 mbar, permeate flow rate: 63 mL/min). In order to have an optimal extraction of the product, the MF TMP (Trans Membrane Pressure) which was controlled by valve 1 on FIG. 2, must be set at 850 mbar (pressure input: 1163 mbar, permeate flow rate: 68 mL/min).

During the diafiltration, the speed of the UF pump (pump 2 on FIG. 2) was set to reach an UF permeate flow equal to the permeate flow MF. Indeed, the volume on the MF tank (vessel 2 on FIG. 2) had to remain as stable as possible during the diafiltration step.

The diafiltration was performed by cycle. At the end of the initial concentration, there was a volume present in the MF tank (vessel 2 on FIG. 2). Once this volume passed through the MF filtration system, one cycle was realized. In this process, the diafiltration needed 5 cycles.

Final concentration: At the end of the 5 diafiltration cycles, the UF pump was stopped. When the MF input pressure started to increase, the MF pump was shut down. At the end of this first filtration step, the product of interest contained elements smaller than 0.45 µm in size.

Filtering 2: The product of interest harvested (mass: 1039.1 g) then undergone a second stage of 5 cycles purification on the UF loop with cut-off point 10 kDa (vessel 3, pump 2 and ultrafiltration filter on FIG. 2). The permeate was waste as mentioned on FIG. 2. The constant volume was maintained during this second filtering step of purification, by adding of NaOH 0.001 N solution at pH 10.0.

The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Once the filtration system conditioned, the UF permeate was opened in order to start the filtering 2 of the product (pressure input: 650 mbar, permeate flow rate: 44 mL/min). In order to have an optimal extraction of the product, the UF TMP (Trans Membrane Pressure) which was controlled by valves 2 and 3 on FIG. 2, must be set at 850 mbar (pressure input: 960 mbar, permeate flow rate: 72 mL/min).

During the filtering 2 step, the volume on the UF tank (vessel 3 on FIG. 2) had to remain as stable as possible. So, as the level of the UF tank (vessel 3 on FIG. 2) decreased, there was an addition of NaOH solution. The 5 cycles corresponding to a volume of NaOH solution added equivalent to 5 times the volume of product of interest harvested.

At the end of filtering 2 step, the final product was harvested (mass: 1033.9 g), and then separated into 2 equal parts. At the end of this second filtration step, the product of interest contained elements smaller than 0.45 µm and taller than 10 kDa in size.

A sample corresponding to the filtrate before neutralization (called "process 2-E2-filtrate") was carried out at this step.

The first part of the filtrate was then neutralized with propionic acid 1/100 at pH 7.2±0.2 (pH: 7.18 adjusted with 4.2 mL of propionic acid 1/100), then sterilized under biosafety cabinet using a filtration with PES 0.2 µm sterilizing membrane.

A sample corresponding to the neutralized filtrate at the end of the process (called "process 2-E3-neutralized filtrate (propionic acid)" 0M314A) was carried out at this step.

At the same time, the second part of the filtrate was subdivided into 9 equal parts. Each of these parts was then neutralized at 7.2±0.2 with hydrochloric 0.25±0 (pH: 7.09) or with organic acids (0M314A): formic 1/100 (pH: 7.13), acetic 1/100 (pH: 7.20), pyruvic 1/100 (pH: 7.15), aspartic 0.1% (pH: 7.12), lactic 1/100 (pH: 7.19), glutamic 0.1% (pH: 7.21), 3-hydroxy-butanoic 1/100 (pH: 7.16), pure ascorbic (pH: 7.25)). Finally, the different products were sterilized under biosafety cabinet using a filtration with PES 0.2 µm sterilizing membrane.

A sample corresponding to the different neutralized filtrates at the end of the process (called "process 2—E4-neutralized filtrate (name of acid)") was carried out at this step.

TABLE 20

| Sample codes summary: | |
| --- | --- |
| Lysate | Process 2-E1-lysate |
| Filtrate | Process 2-E2-Filtrate |
| Standard Neutralized Filtrate | Process 2-E3-neutralized filtrate (propionic acid) |
| Acid 1 neutralized Filtrate | Process 2-E4-neutralized filtrate (hydrochloric acid) |
| Acid 2 neutralized Filtrate | Process 2-E4-neutralized filtrate (formic acid) |
| Acid 3 neutralized Filtrate | Process 2-E4-neutralized filtrate (acetic acid) |
| Acid 4 neutralized Filtrate | Process 2-E4-neutralized filtrate (pyruvic acid) |
| Acid 5 neutralized Filtrate | Process 2-E4-neutralized filtrate (aspartic acid) |
| Acid 6 neutralized Filtrate | Process 2-E4-neutralized filtrate (lactic acid) |
| Acid 7 neutralized Filtrate | Process 2-E4-neutralized filtrate (glutamic acid) |
| Acid 8 neutralized Filtrate | Process 2-E4-neutralized filtrate (3-hydroxy-butanoic acid) |
| Acid 9 neutralized Filtrate | Process 2-E4-neutralized filtrate (ascorbic acid) |

Example 1.10.2. Analytical Characterization

Analytical methods are described in 1.6.2
Results at Release (T0):

E2-Filtrate solutions were frozen after process and were thawed at 4° C. overnight before analysis.

TABLE 21

Process 2-Analytical results

| Test | Sample | Result | Unit |
|---|---|---|---|
| Dry weight (total) | Process 2-E1-lysate | 24.5 | [mg/g] |
| Dry weight (supernatant) | Process 2-E1-lysate | 21.2 | [mg/g] |
| Dry weight (filtrate) | Process 2-E2-Filtrate | 8.4 | [mg/g] |
| Proteins total | Process 2-E2-Filtrate | 7.7 | [mg/mL] |
| Sugar total | Process 2-E2-Filtrate | 0.20 | [mg/mL] |
| Endotoxin LAL* | Process 2-E3-neutralized filtrate (propionic acid) | 16.2 | [EU/mL] |
| DNA** | Process 2-E3-neutralized filtrate (propionic acid) | ND | [µg/mL] |
| RNA*** | Process 2-E3-neutralized filtrate (propionic acid) | ND | [µg/mL] |

ND = not detected;
*Endotoxin LAL: limit of detection = 0.1 EU/mL;
**DNA: limit of detection = 3.60 µg/mL, limit of quantification = 12.01 µg/mL;
***RNA: limit of detection = 4.29 µg/mL, limit of quantification = 14.32 µg/mL

TABLE 22

Process 2-Total Amino Acids after acid hydrolysis

Figure 30:
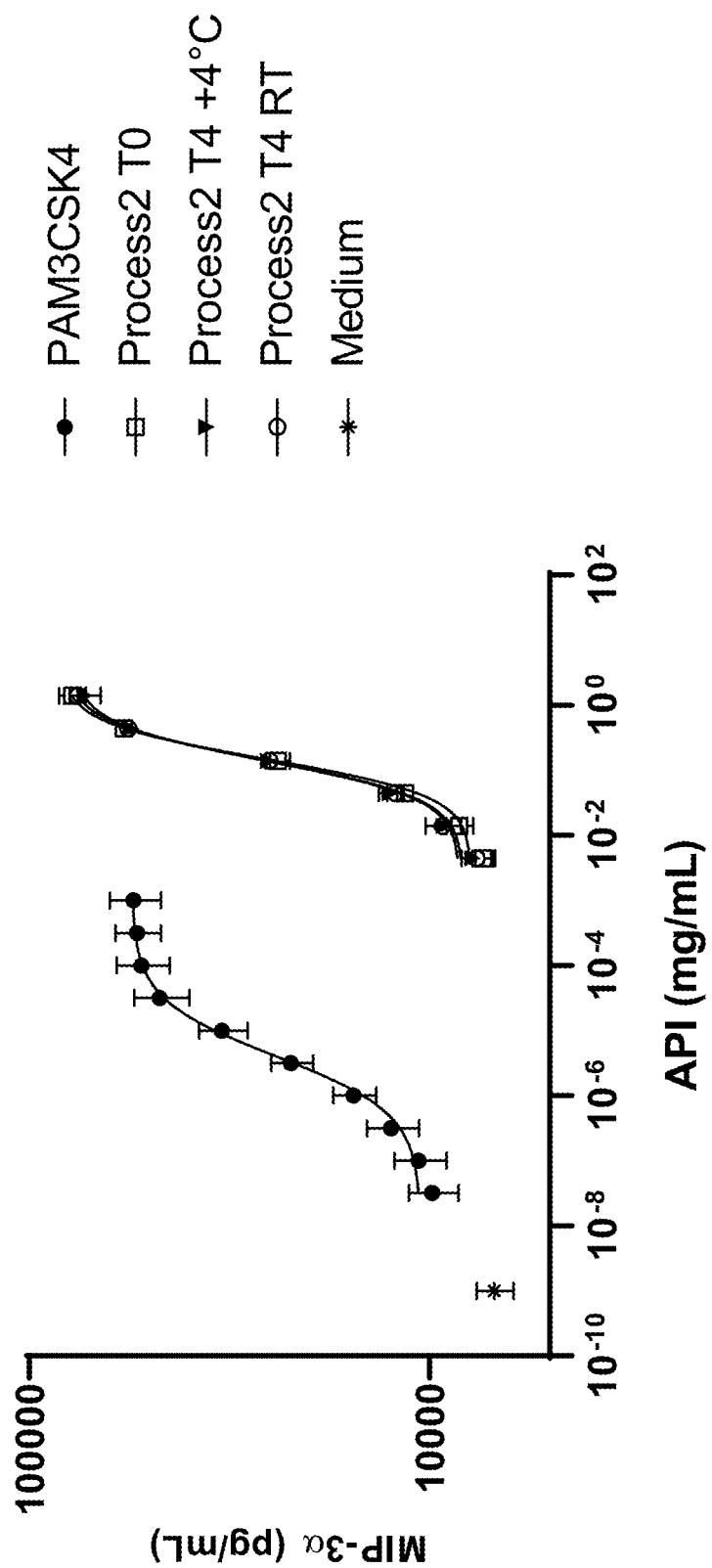
FIG. 30: Process 2—bioassay results during stability shows that Process 2—E3—neutralized filtrate (OM314A) exhibited a comparable bioactivity through MIP-3α secretion on THP-1 during at least 4 months at room temperature (20° C.+/−5° C.) or 4° C. Process 2 T0 was compared to T4 samples stored at 4° C. and at room temperature (RT) for 4 month.

| Amino Acid | Concentration (µmol/mL) | %/AA (D vs L) |
|---|---|---|
| L-Asp | 0.87 | 77 |
| D-Asp | 0.26 | 23 |
| L-Glu | 1.25 | 87 |
| D-Glu | 0.18 | 13 |
| L-Ser | 0.40 | 54 |
| D-Ser | 0.34 | 46 |
| L-Thr | 0.47 | 17 |
| D-Thr | 2.31 | 83 |
| L-His | 0.00 | NA |
| Gly | 0.21 | NA |
| D-His | 0.00 | NA |
| L-Ala | 1.18 | NA |
| L-Arg | 1.07 | NA |
| D-Arg + D-Ala | 0.11 | NA |
| L-Tyr | 0.51 | 85 |
| D-Tyr | 0.09 | 15 |
| L-Val | 0.68 | 100 |
| L-Met | 0.41 | 100 |
| D-Met | 0.00 | 0 |
| L-Cys | 0.08 | NA |
| D-Val | 0.00 | 0 |
| L-Ile | 0.58 | 100 |
| L-Phe | 0.63 | 84 |
| D-Phe | 0.12 | 16 |
| L-Leu | 1.31 | 100 |
| D-Ile | 0.00 | 0 |
| D-Leu | 0.00 | 0 |
| L-Lys | 1.67 | 94 |
| D-Lys | 0.12 | 6 | a) Mip3-Alpha (CCL20) Results Obtained During Stability:

FIG. 30: Process 2—bioassay results during stability shows that Process 2—E3—neutralized filtrate exhibited a comparable bioactivity through MIP-3α secretion on THP-1 during at least 4 months at room temperature (20° C.+/−5° C.) or 4° C. Process 2 T0 was compared to T4 samples stored at 4° C. and at room temperature (RT) for 4 month.

Example 1.11-21 Strain Bacterial Lysate Extract 30 kDa (BE30 kD, OM314A)

Example 1.11.1 Process 6: 21 Strain Bacterial Lysate Extract 30 kDa (BE30 kD. OM314A)

Lysis: A part of 21 strain bacterial polylysate (Industrial Batch 1619064 described as 21 strain lysates in WO 2008/109669) was recovered in production and was stored in a 2500 mL mini-cask (reference: Semadeni no 6863).

Filtering 1: The installation for the filtration of the product was prepared in accordance with the diagram (FIG. 2). The filtration system consists of 2 filtration loops. A first microfiltration (called MF) consisting of a tank (vessel 2 on FIG. 2), a pump (pump 1 on FIG. 2) and a filtration system with a cut-off point of 0.45 µm (micro-filter on FIG. 2). The second loop, ultrafiltration (called UF), consists of a tank (vessel 3 on FIG. 2), a pump (pump 2 on FIG. 2) and a filtration system with a cut-off point of 30 kDa (ultrafiltration filter on FIG. 2). The filtration took place at the laboratory scale with an implemented volume of 2000 mL.

Before starting the process, we had to ensure that the filtration system was reproducible over batches. To verify the correct filterability of the product, an NWP (Normalized Water Permeability) was performed on the filtration system.

The lysate used for the production was first diluted 2 times with purified water (1000.2 g of lysate and 1000.1 g of purified water). The product was stirred to have a product vortex of 1 cm. The temperature of the product was cooled to room temperature while waiting the filtering process to start. In this process there was a pH adjustment at pH 10.5-10.8 (pH: 10.73 adjusted with pure aspartic acid).

Initial concentration: The product used for the first step of filtration had the following parameters (pH: 10.73), temperature 25° C., stirred to have a product vortex of 1 cm). The MF loop pump (pump 1 on FIG. 2) was started at 40% of the process speed to charge the system with the product. Once this step was completed, the recirculation of the product on the MF loop started and the pump speed was increased regularly to reach 75% of the process speed. Recirculation allows the hydrophilic filtration system to be conditioned by eliminating the air bubbles present in the system.

When the flow rate and the pressure were stable, the filtration system was considered as conditioned. Then, the permeate valve of the MF loop was opened in order to perform an initial concentration of the product with a concentration factor to 0.5 (pressure input: 235 mbar, permeate flow rate: 52 mL/min). During the initial concentration, the pump (pump 1 on FIG. 2) speed was gradually increased to 100% (100 rpm corresponding to 600 mL/min) of the process speed.

Parallel to this step, the UF loop was conditioned. The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Diafiltration: When the 0.5 concentration factor was reached, the UF permeate was opened in order to start the diafiltration of the product (pressure input: 734 mbar, permeate flow rate: 52 mL/min). In order to have an optimal extraction ofthe product, the MF TMP (Trans Membrane Pressure) which was controlled by valve 1 on FIG. 2, must be set at 850 mbar (pressure input: 1010 mbar, permeate flow rate: 48 mL/min).

During the diafiltration, the speed of the UF pump (pump 2 on FIG. 2) was set to reach an UF permeate flow equal to the permeate flow MF. Indeed, the volume on the MF tank (vessel 2 on FIG. 2) had to remain as stable as possible during the diafiltration step.

The diafiltration was performed by cycle. At the end of the initial concentration, there was a volume present in the MF tank (vessel 2 on FIG. 2). Once this volume passed through the MF filtration system, one cycle was realized. In this process, the diafiltration needed 5 cycles.

Final concentration: At the end of the 5 diafiltration cycles, the UF pump was stopped. When the MF input pressure started to increase, the MF pump was shut down. At the end of this first filtration step, the product of interest contained elements smaller than 0.45 μm in size.

Filtering 2: The product of interest harvested (mass: 1179.6 g) then undergone a second stage of 5 cycles purification on the UF loop with cut-off point 30 kDa (vessel 3, pump 2 and ultrafiltration filter on FIG. 2). The permeate was waste as mentioned on FIG. 2. The constant volume was maintained during this second filtering step of purification, by adding of NaOH 0.001 N solution at pH 10.3.

The UF loop pump (pump 2 on FIG. 2) was started at 40% of the process speed to charge the system with the product. Once this step was completed, the recirculation of the product on the UF loop started and the pump speed was increased regularly to reach 75% of the process speed. Recirculation allows the hydrophilic filtration system to be conditioned by eliminating the air bubbles present in the system.

Once the filtration system conditioned, the UF permeate was opened in order to start the filtering 2 of the product (pressure input: 670 mbar, permeate flow rate: 67 mL/min). In order to have an optimal extraction of the product, the UF TMP (Trans Membrane Pressure) which was controlled by valves 2 and 3 on FIG. 2, must be set at 850 mbar (pressure input: 920 mbar, permeate flow rate: 88 mL/min). During the filtering 2 step, the volume on the UF tank (vessel 3 on FIG. 2) had to remain as stable as possible. So, as the level of the UF tank (vessel 3 on FIG. 2) decreased, there was an addition of NaOH solution. The 5 cycles corresponding to a volume of NaOH solution added equivalent to 5 times the volume of product of interest harvested.

At the end of filtering 2 step, the final product was harvested (mass: 1070.5 g). At the end of this second filtration step, the product of interest contained elements smaller than 0.45 μm and taller than 30 kDa in size.

The filtrate was then neutralized with aspartic acid 0.1% at pH 7.2±0.2 (pH: 7.19 adjusted with 180 mL of aspartic acid 0.1%), then sterilized under biosafety cabinet using a filtration with PES 0.2 μm sterilizing membrane.

A sample corresponding to the neutralized filtrate at the end of the process (called "process 6-E3-neutralized filtrate (aspartic acid)", OM314A) was carried out at this step.

Example 2: Stable Formulations for Intranasal, Intratracheal, Inhalation and Perioral Use Example 2.1: Intranasal Formulation of OM314A Stabilized Bacterial Extract High molecular fraction (>10 kD) of the organic acid stabilized OM314A bacterial extract was adjusted to pH 7.5 at a final concentration of 5 mg dry weight/mL (range 1 to 20 mg/mL) using sterile saline (0.9% NaCl in water for injection) and sterilized by 0.2 μm filtration. The final solution was added to nasal spray medical device vial (10 mL, range 1 to 25 mL) with a typical dose of 0.05 mL containing 0.25 mg of the organic acid stabilized OM bacterial extract (range 0.025 to 0.1 mL per dose).

Therapeutic dose: single daily dose as well as bi-daily dose range from 0.025 to 0.1 mL per administration containing from 0.05 to 1 mg can be reached with these formulations.

Example 2.2: Intranasal Formulation of *Lactobacillus fermentum* Stabilized Bacterial Extract 20 (OM314B)

High molecular fraction (>10 kD) of the organic acid stabilized *Lactobacillus fermentum* bacterial extract (OM314B) was adjusted to pH 7.5 at a final concentration of 5 mg dry weight/mL (range 1 to 20 mg/mL) using sterile saline (0.9% NaCl in water for injection) and terilized by 0.2 μm filtration. The final solution was added to nasal spray medical device vial (10 mL, range 1 to 25 mL) with a typical dose of 0.05 mL containing 0.25 mg of the organic acid stabilized *Lactobacillus fermentum* purified bacterial extract (range 0.025 to 0.1 mL per dose).

Therapeutic dose: single daily dose as well as bi-daily dose range from 0.025 to 0.1 mL per administration containing from 0.05 to 1 mg can be reached with these formulations.

Example 2.3: Intranasal Formulation of *Escherichia coli* Stabilized Bacterial Extract (OM314C)

High molecular fraction (>10 kD) of the organic acid stabilized *Escherichia coli* bacterial extract was adjusted to pH 7.5 at a final concentration of 5 mg dry weight/mL (range 1 to 20 mg/mL) using sterile saline (0.9% NaCl in water for injection) and sterilized by 0.2 μm filtration. The final solution was added to nasal spray medical device vial (10 mL, range 1 to 25 mL) with a typical dose of 0.05 mL containing 0.25 mg of the organic acid stabilized *Escherichia coli* purified bacterial extract (range 0.025 to 0.1 mL per dose).

Therapeutic dose: single daily dose as well as bi-daily dose range from 0.025 to 0.1 mL per administration containing from 0.05 to 1 mg can be reached with these formulations.

Example 2.4: Inhalation Formulation as Liquid Droplet Spray of OM314A Bacterial Stabilized Extract High molecular fraction (>10 kD) of the organic acid stabilized OM314A bacterial extract was adjusted to pH 7.5 at a final concentration of 5 mg dry weight/mL (range 1 to 20 mg/mL) using sterile saline (0.9% NaCl in water for injection) and sterilized by 0.2 μm filtration. The final solution was added to a spray-inhalator medical device vial (10 mL, range 1 to 25 mL) with atypical dose of 0.1 mL containing 0.5 mg of the organic acid stabilized OM bacterial extract (range 0.05 to 0.4 mL per dose).

Therapeutic dose: single daily dose as well as bi-daily dose range from 0.05 to 0.4 mL per administration containing from 0.05 to 8 mg can be reached with these formulations.

Example 2.5: Inhalation Formulation as Liquid Droplet Spray of *Lactobacillus fermentum* Bacterial Stabilized Extract (OM314B)

High molecular fraction (>10 kD) of the organic acid stabilized *Lactobacillus fermentum* bacterial extract (OM314B) was adjusted to pH 7.5 at a final concentration of 5 mg dry weight/mL (range 1 to 20 mg/mL) using sterile saline (0.9% NaCl in water for injection) and sterilized by 0.2 μm filtration. The final solution was added to a spray-inhalator medical device vial (10 mL, range 1 to 25 mL) with atypical dose of 0.1 mL containing 0.5 mg of the organic acid stabilized *Lactobacillus fermentum* purified bacterial extract (range 0.05 to 0.4 mL per dose).

Therapeutic dose: single daily dose as well as bi-daily dose range from 0.05 to 0.4 mL per administration containing from 0.05 to 8 mg can be reached with these formulations.

Example 2.6: Inhalation Formulation as Solid Particles of OM314A Stabilized Bacterial Extract High molecular fraction (>10 kD) of the organic acid stabilized OM314A bacterial extract was adjusted to pH 7.5 at a final concentration of 10 mg dry weight/mL (range 1 to 20 mg/mL) using sterile saline (0.9% NaCl in water for injection), one or more excipients from the list* and sterilized by 0.2 μm filtration. In one example, a solution of 10 mg/mL of the bacterial extract was mixed with mannitol (25 mg/mL), lactose (25 mg/mL) and Mg stearate (1 mg/mL).

After spray drying the powder is compressed into tablets (12 mg tablets). Crushable tablets are distributed into a medical device (particle size range 1 to 7 μm) and inhalation dose from a 12 mg tablet was 2 mg bacterial extract.

Typical excipients for inhalation but not limited to are: lactose, glucose, mannitol, trehalose, Mg stearate, DPPC, DSPC, DMPC, cholesterol, leucine, trileucine, Poloxamer, bile salts, chitosan, trimethylchitosan, PLGA (see G. Pilcer, K. Amighi, International Journal of Pharmaceutics, 2010, 392, 1-19 for a review)

Example 2.7: Inhalation Formulation as Solid Particles of *Lactobacillus fermentum* Stabilized Bacterial Extract (OM314B)

High molecular fraction (>10 kD) of the organic acid stabilized *Lactobacillus fermentum* bacterial extract (OM314B) was adjusted to pH 7.5 at a final concentration of 10 mg dry weight/mL (range 1 to 20 mg/mL) using sterile saline (0.9% NaCl in water for injection), one or more excipients from the list* and sterilized by 0.2 μm filtration. In one example, a solution of 10 mg/mL of the bacterial extract was mixed with mannitol (25 mg/mL), lactose (25 mg/mL) and Mg stearate (1 mg/mL). After spray drying the powder is compressed into tablets (12 mg tablets). Crushable tablets are distributed into a medical device (particle size range 1 to 7 μm) and inhalation dose from a 12 mg tablet was 2 mg bacterial extract.

Typical excipients for inhalation but not limited to are: lactose, glucose, mannitol, trehalose, Mg stearate, DPPC, DSPC, DMPC, cholesterol, leucine, trileucine, Poloxamer, bile salts, chitosan, trimethylchitosan, PLGA (see G. Pilcer, K. Amighi, International Journal of Pharmaceutics, 2010, 392, 1-19 for a review).

Example 3: Evidence of a Higher Stability of the Novel Bacterial Extract Formulations Extracts prepared according to examples 1.1, 1,2, 1.3, 1.4 and formulations according to examples 2.1, 2.2, 2.3, 2.4, 2.5 are adjusted to pH 6.6, 6.7, 6.8, 6.9, 7.0, 7.1, 7.2, 7.3, 7.4, 7.5, 7.6 using the different organic acids selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, and a combination thereof.

10 Stability of the bacterial extracts stored at 5° C.±3° C. and at room temperature 20° C. to 25° C. are observed visually for the presence of a precipitate at different time points from day 0 (between 15 min and 120 min after pH adjustment) and after 30, 60, 90, 180, 360 days.

Quantification is performed using visible-spectrophotometry by measuring their absorbance at 550, 600, 650, 700 nm determined at different time points from day 0 (between 15 min and 120 min after pH adjustment) and after 30, 60, 90, 180, 360 days. Spectrophotometry is performed against a water sample.

Stability is expressed as a change in absorbance is depending on the process, on the organic acid or organic acid combination used as well as on the final pH value.

Example 4: Prophylactic and Curative Efficacy of OM Intranasal Versus Oral Administration in an Animal Model of Sub-Lethal Bacterial Infection Following Primo Influenza Infection A stable perioral form of the OM bacterial extract (bacterial extract from 21 strain lysates) has been prepared extemporaneously for the purpose of experimentally testing perioral administration of the OM bacterial extract in animal models. This extemporaneous perioral form was stable over time but results provided insights and evidenced substantial therapeutic benefits of the perioral administrations.

Figure 3:
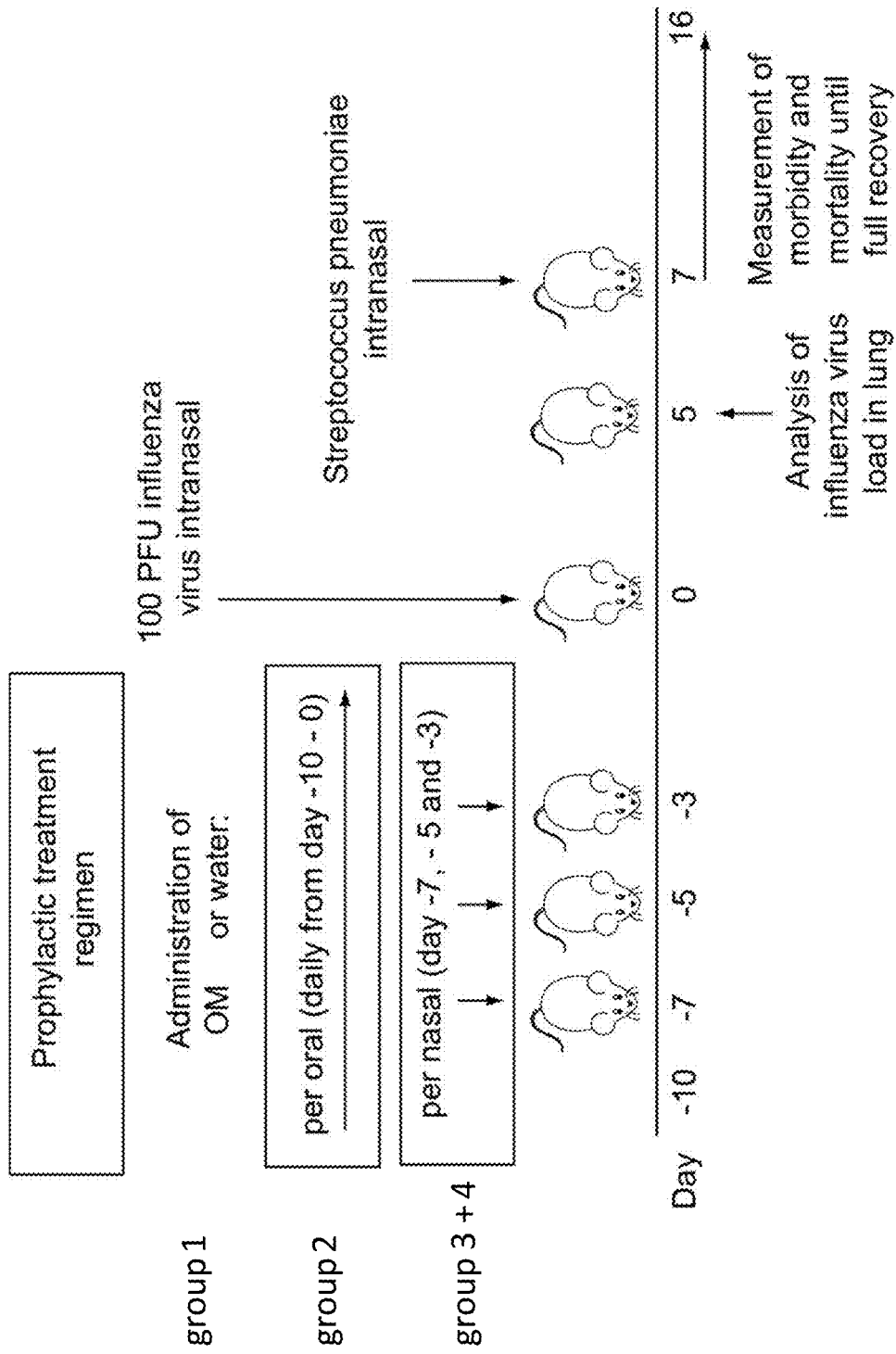
FIG. 3: shows the study design of a superinfection experiment: viral lung infection followed by bacterial lung infection. Dosing schedule of OM bacterial extract administration by oral route (groups 2) versus intranasal route (groups 3 and 4) and saline intranasal (group 1) is shown.

The efficacy of intranasal administration of the extemporaneous perioral OM bacterial extract in reducing viral titer in the lung tissue after influenza viral infection and (2) reducing morbidity and mortality of superinfected animals (animals treated with sublethal influenza viral infection followed by sublethal bacterial infection) was compared to that of the oral administration of the OM bacterial extract (FIG. 3).

Female BALB/c mice (8 weeks old, Charles River Laboratories) were anesthetized by intraperitoneal injection of ketamine and xylasol and inoculated intranasally with 100 PFU of Influenza strain A/Puerto Rico8/34 in a volume of 50 ul PBS. On day 6 post influenza infection bacterial starter cultures were initiated, followed by expansion to log phase growth on day 7 post influenza infection.

For oral administration, 320 μL of the OM concentrate was administered per gavage yielding in 360 mg/kg of active principle of OM lyophilisate per animal/day, which yielded into a daily administration of 7.2 mg active principle per mouse (FIG. 3). For intranasal administration of LPS (within the scope of performing a COPD model), the dose used was 7 microgram LPS per dose per nasal. In the literature, the administration of 1 microgram of LPS per nasal, has been reported to protect against allergic inflammation. The test schedule is recapitulated in the following Table 23:

TABLE 23

| | |
|---|---|
| Day −10 to −1 | Administration of water control per oral (Group 1). |
| Day −10 to −1 | Administration of OM bacterial extract per oral (Group 2) |
| Day −7, −5 and −3 | Administration of extemporaneous intranasal OM bacterial extract (Groups 3 and 4) |

TABLE 23-continued

| | |
|---|---|
| Day 0 | Sublethal infection with influenza A virus (100 PFU per nasal, influenza strain H1N1 PR/8/34) |
| Day 5 | Sacrifice 5 animals per group for analysis (Groups 1 to 4) |
| Day 5 | Interim bleed (12 animals per group, Groups 1 to 4) |
| Day 7 | Sub-lethal infection with *Streptococcus pneumoniae* (15 animals per group, Groups 1 to 4) |
| Day 0, 7-12 | Daily measurement of weight, temperature, clinical score and lethality (12 animals per group, Groups 1 to 4) |
| Day 12-16 | Every second day measurement of weight, temperature, clinical score and lethality until animals are fully recovered (all remaining animals) |

Figure 4:
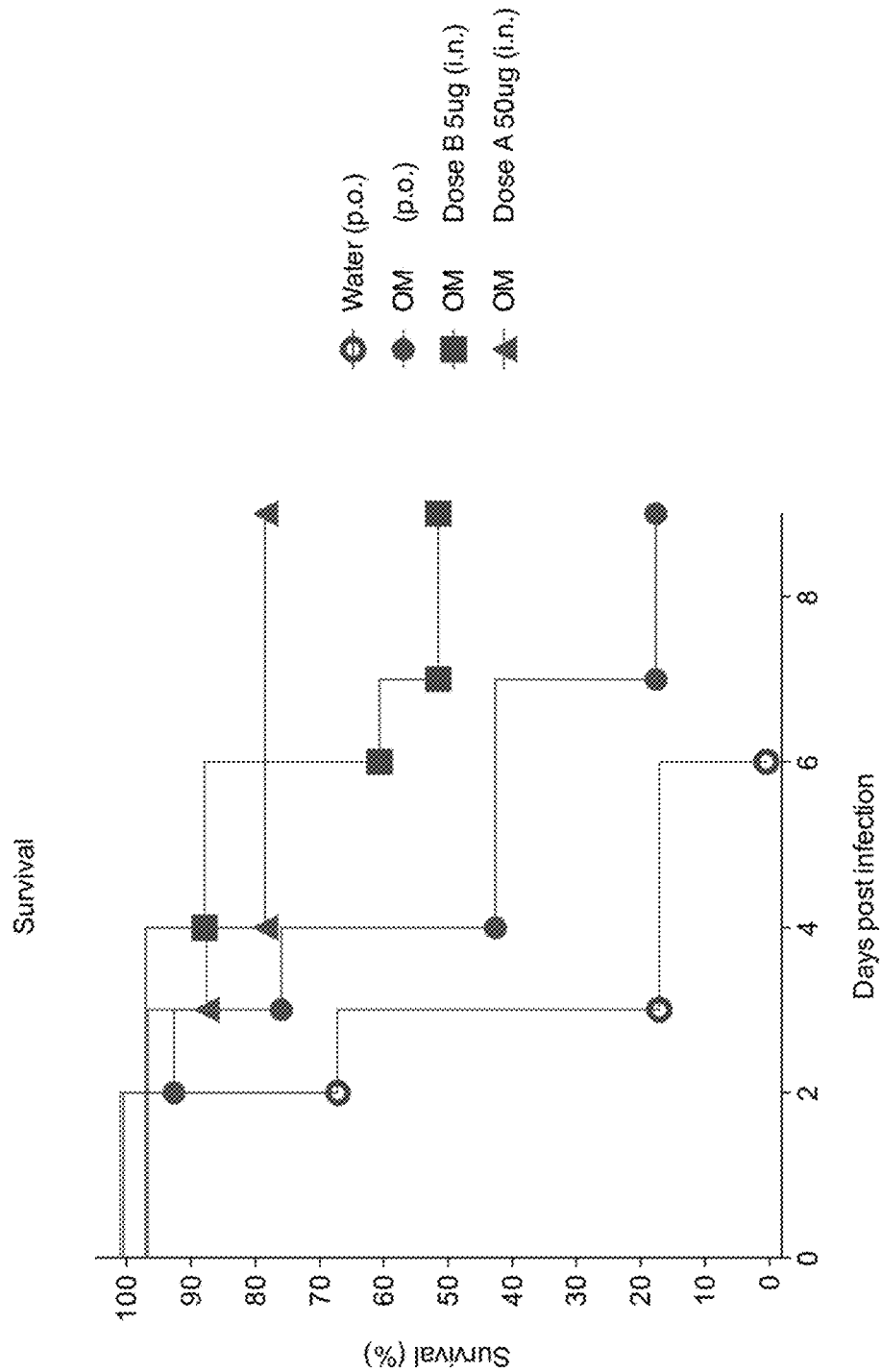
FIG. 4: shows the results obtained after superinfection and showing that intranasal OM bacterial extract treatment (i.n. dose A=50 micrograms and dose B=5 micrograms) yielded a significant increase of survival rate compared to oral (p.o. 7 milligrams) OM bacterial extract and saline control treated animals.
Figure 5:
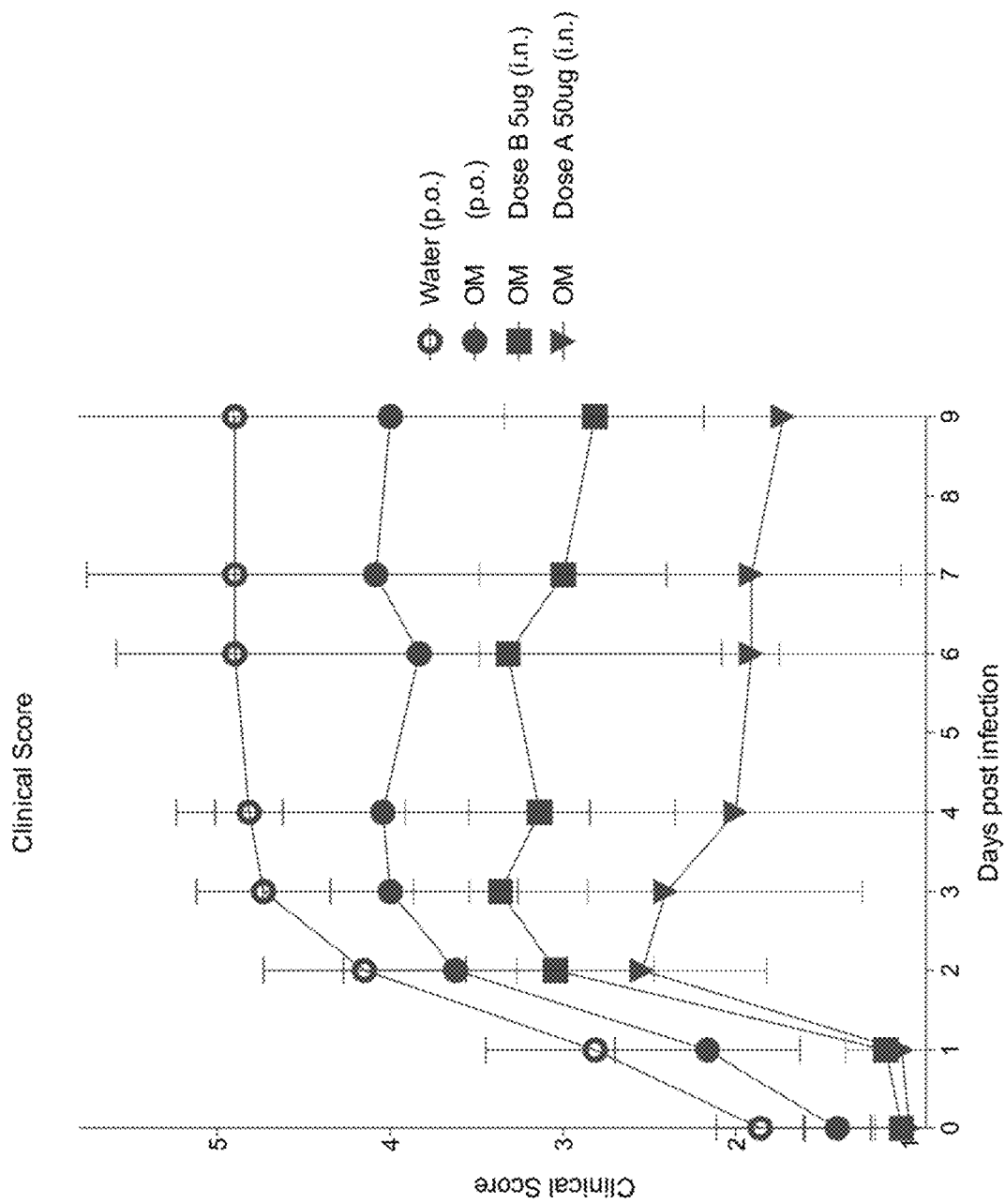
FIG. 5: shows the results obtained after superinfection and showing that prophylactic intranasal OM bacterial extract treatment yielded a significant alleviation of morbidity and mortality following post-influenza bacterial infection summarized here with the clinical score measurement after administration of both intranasal (i.n.) 5 and 50 micrograms OM bacterial extract versus oral (p.o.) 7 milligram OM bacterial extract all compared to the saline control group.
Figure 6:
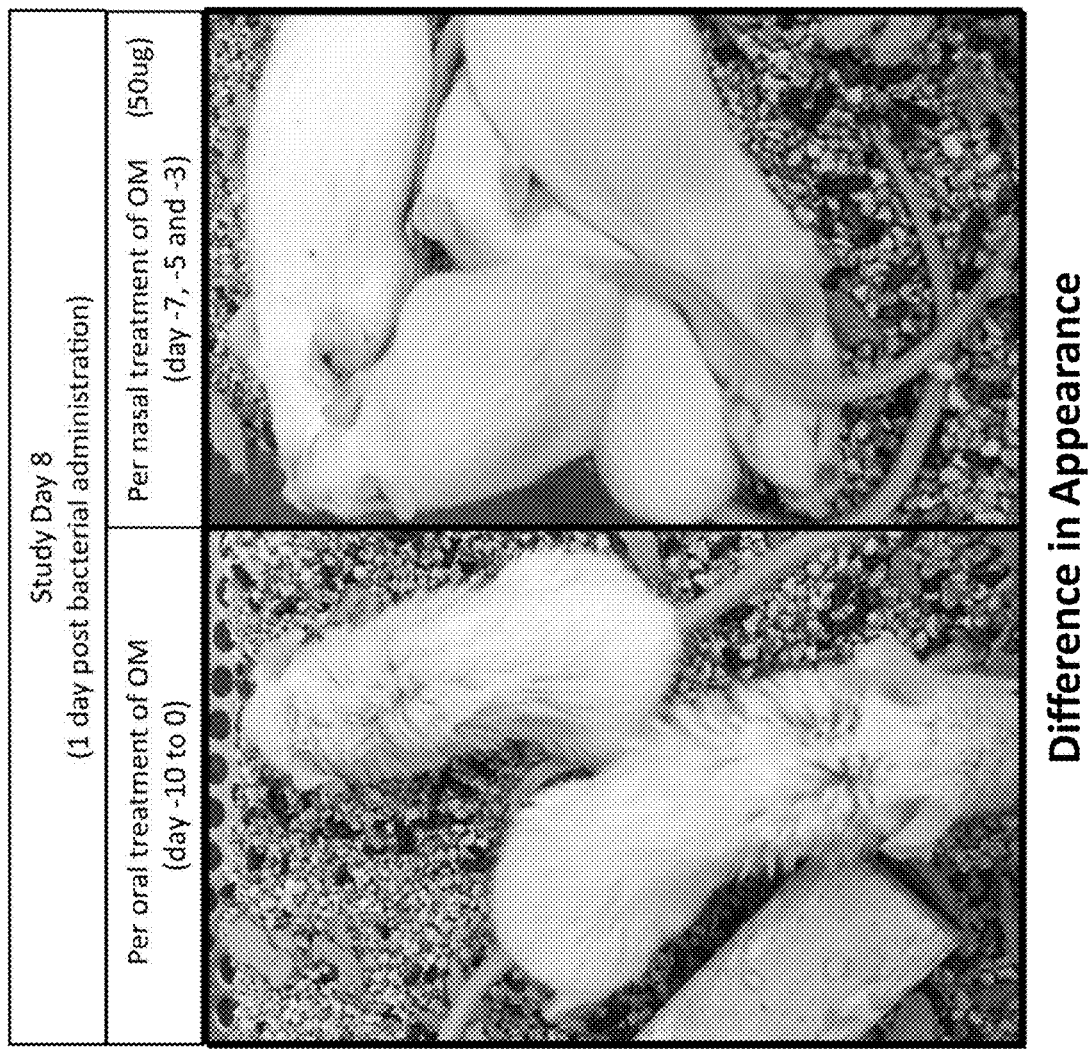
FIG. 6: is a photograph illustrating the difference of comorbidity signs one day post bacterial infection (day 8 from scheme FIG. 3) observed in mice treated with 7 milligram OM bacterial extract via oral route (here illustrated as transient rough hair coat) versus 50 microgram OM bacterial extract via intranasal route (showing healthy animals).

Statistics were performed using GraphPad Prism version 5.0d. A Student's t-test was performed on viral load. Two-way ANOVA was performed on the weight, temperature and clinical score. Curve comparisons were made for survival. Overall, OM bacterial extract treatment protected mice against morbidity and mortality in the superinfection model. This protective effect was most noticeable with the intranasal treatment suggesting that mucosal administration of OM bacterial extract could greatly improve its efficacy (FIGS. 4, 5) and comorbidity following secondary bacterial infection (FIG. 6).

Figure 10:
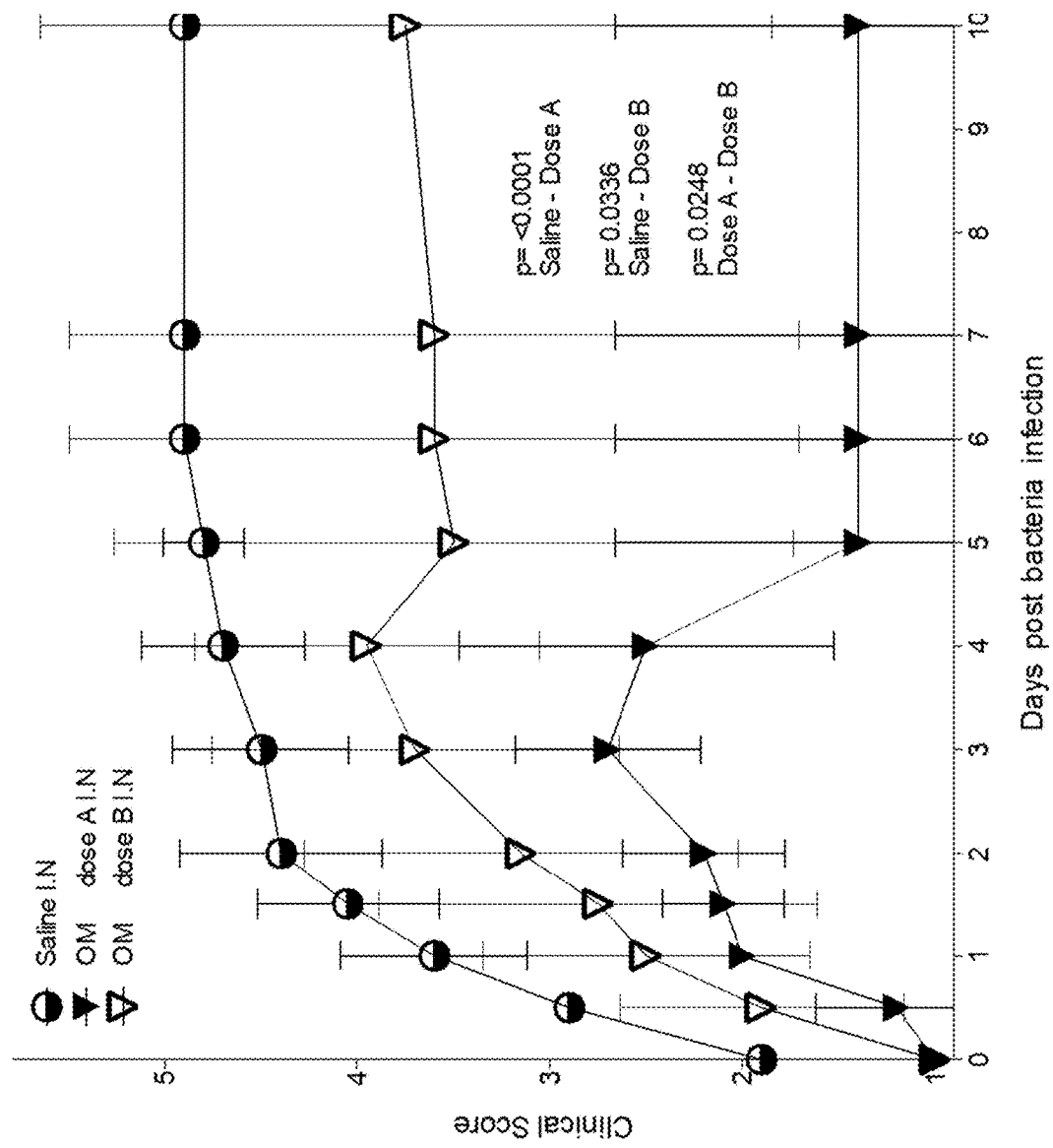
FIG. 10: is a graph showing that intranasal prophylactic OM bacterial extract treatment yielded a significant alleviation of morbidity and mortality following post-influenza bacterial infection summarized here with the clinical score measurement after administration of both intranasal 5 micrograms (dose A) and 50 micrograms (dose B) OM bacterial extract versus saline control group. Clinical efficacy was proportional to the dose.
Figure 12:
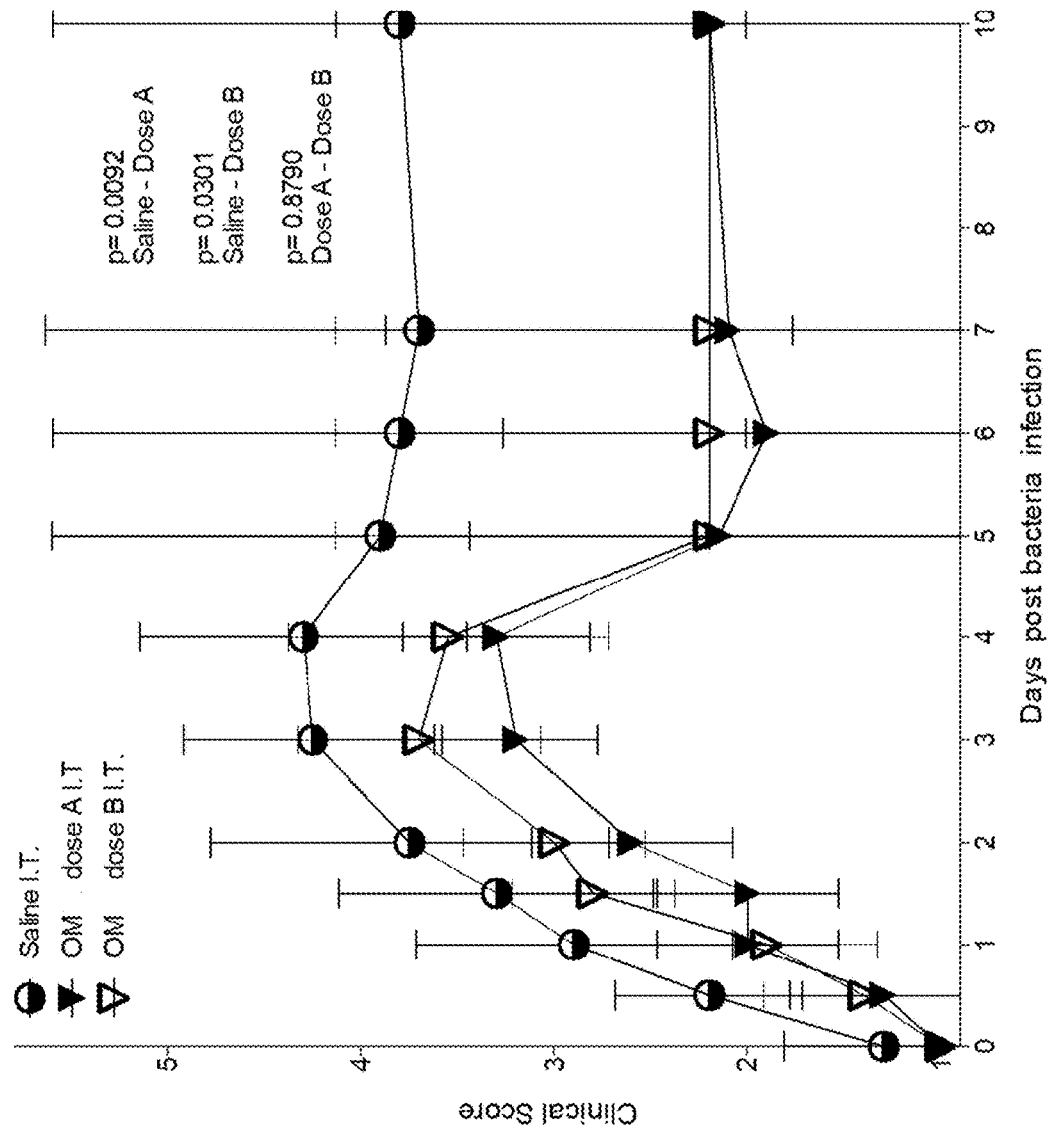
FIG. 12: is a graph showing that prophylactic intratracheal OM bacterial extract treatment yielded a significant alleviation of morbidity and mortality summarized here with the clinical score measurement after administration of 50 micrograms (dose A.I.T) and 5 micrograms (dose B.IT) doses.

Example 5: Prophylactic Efficacy of Intranasal and Intratracheal OM Bacterial Extract Administration in an Animal Model of Sub-Lethal Bacterial Infection Following Primo Influenza Infection This study outlined in FIG. 7 evidenced the efficacy of intranasal and intratracheal administration of OM bacterial extract (bacterial extract from 21 strain lysates) as prophylactic treatment regimen for (1) reducing viral titer in the lung tissue after influenza viral infection (FIG. 8) and (2) reducing morbidity and mortality of superinfected animals (animals treated with sublethal influenza viral infection followed by sublethal bacterial infection) as evidenced by the clinical scores (FIGS. 10 and 12). Two different doses of OM bacterial extract were tested, DOSE A (50 microgram of active ingredient per administration) and DOSE B (5 microgram of active ingredient per administration). Female BALB/c mice (8 weeks old, Charles River Laboratories) were anesthetized by intraperitoneal injection of ketamine and xylasol and inoculated intranasally with 100 PFU of Influenza strain A/Puerto Rico8/34 in a volume of PBS.

The mice were divided into 6 groups of 15 each. Group 1 was administered saline drops, via intranasal (i.n.) route at day d7, d5, and d3 (prophylactic control). Group 2 was administered a prophylactic dose A of OM bacterial extract via the intranasal route, at day d7, d5, and d3. Group 2 was administered a prophylactic dose B of OM bacterial extract via the intranasal (i.n.) route, at day-7, -5, and -3. Group 4 was a saline spray administered intratracheally (i.t.) at day-7, -5, and -3. Group 5 was administered a prophylactic dose A of OM bacterial extract via the intratracheal route, at day-7, -5, and -3. Group 6 was administered prophylactic dose B of OM bacterial extract via the intratracheal route, at day-7, -5, and -3. OM bacterial extract administration with 50 microgram active ingredient (DOSE A, yielding in 2.2 microliter of OM bacterial extract concentrate) and with 5 microgram active ingredient (DOSE B yielding in 0.22 microliter of OM bacterial extract concentrate) per mouse/per time point.

On day 6 post influenza infection bacterial starter cultures were initiated, followed by expansion to log phase growth on day 7 post influenza infection.

Figure 7:
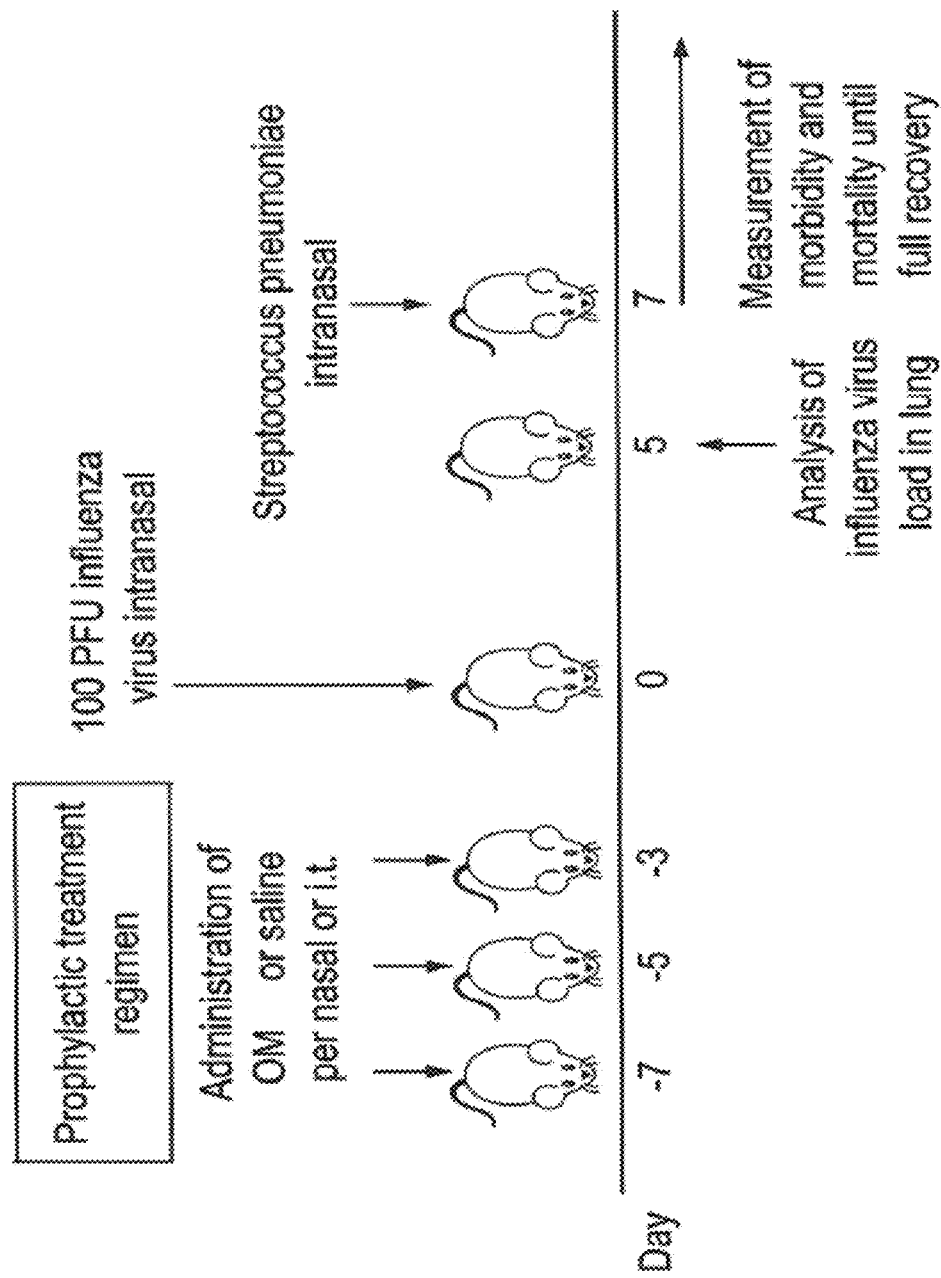
FIG. 7: shows the study design of a superinfection experiment: viral lung infection followed by bacterial lung infection. Dosing regimen of OM bacterial extract administration by intranasal (per nasal) route versus intratracheal (i.t.) route versus saline controls is shown in the figure.

The study design and dosing schedule is showed in FIG. 7 as well as in the following Table 24.

TABLE 24

| | |
|---|---|
| Day -7, -5, -3 | Administration of saline intranasal (Group 1) or intratracheal (Group 4) |
| Day -7, -5, -3 | Administration of OM bacterial extract intranasal (Groups 2 and 3) or intratracheal (Groups 5 and 6). |
| Day 0 | Sublethal infection with influenza A virus (100 PFU per nasal, influenza strain H1N1 PR/8/34). |
| Day 5 | Sacrifice 5 animals per group for analysis (Groups 1-6). |
| Day 7 | Sublethal infection with *Streptococcus pneumoniae* (10 animals per group, Groups 1-6) |
| Day 7 | Sublethal infection with *Streptococcus pneumoniae* (12 animals per group, Groups 1-3). |
| Days 0, 7-12 | Daily measurement of weight, temperature, clinical score and lethality (10 animals per group, Groups 1-6). |
| Day >12 | Every second or third day measurement of weight, temperature, clinical score and lethality until animals are fully recovered (all remaining animals) |

Animals were anesthetized by intraperitoneal injection of ketamine and xylasol and OM bacterial extract was administered intranasally or intratracheally diluted in saline with either 50 microgram active ingredient (DOSE A, yielding in 2.2 microliter of OM bacterial extract concentrate) or with 5 microgram active ingredient (DOSE B yielding in 0.22 microliter of OM bacterial extract concentrate) in a total volume of 50 microliter.

Animals were anesthetized by intraperitoneal injection of ketamine and xylasol and OM bacterial extract was administered intranasally or intratracheally diluted in saline with either 50 microgram active ingredient (DOSE A, yielding in 2.2 microliter of OM bacterial extract concentrate) or with 5 microgram active ingredient (DOSE B yielding in 0.22 microliter of OM bacterial extract concentrate) in a total volume of 50 microliter.

Statistics were performed using GraphPad Prism version 5.0d. A Student's I-test was performed on viral load. Two-way ANOVA was performed on the weight, temperature and clinical score.

Figure 8:
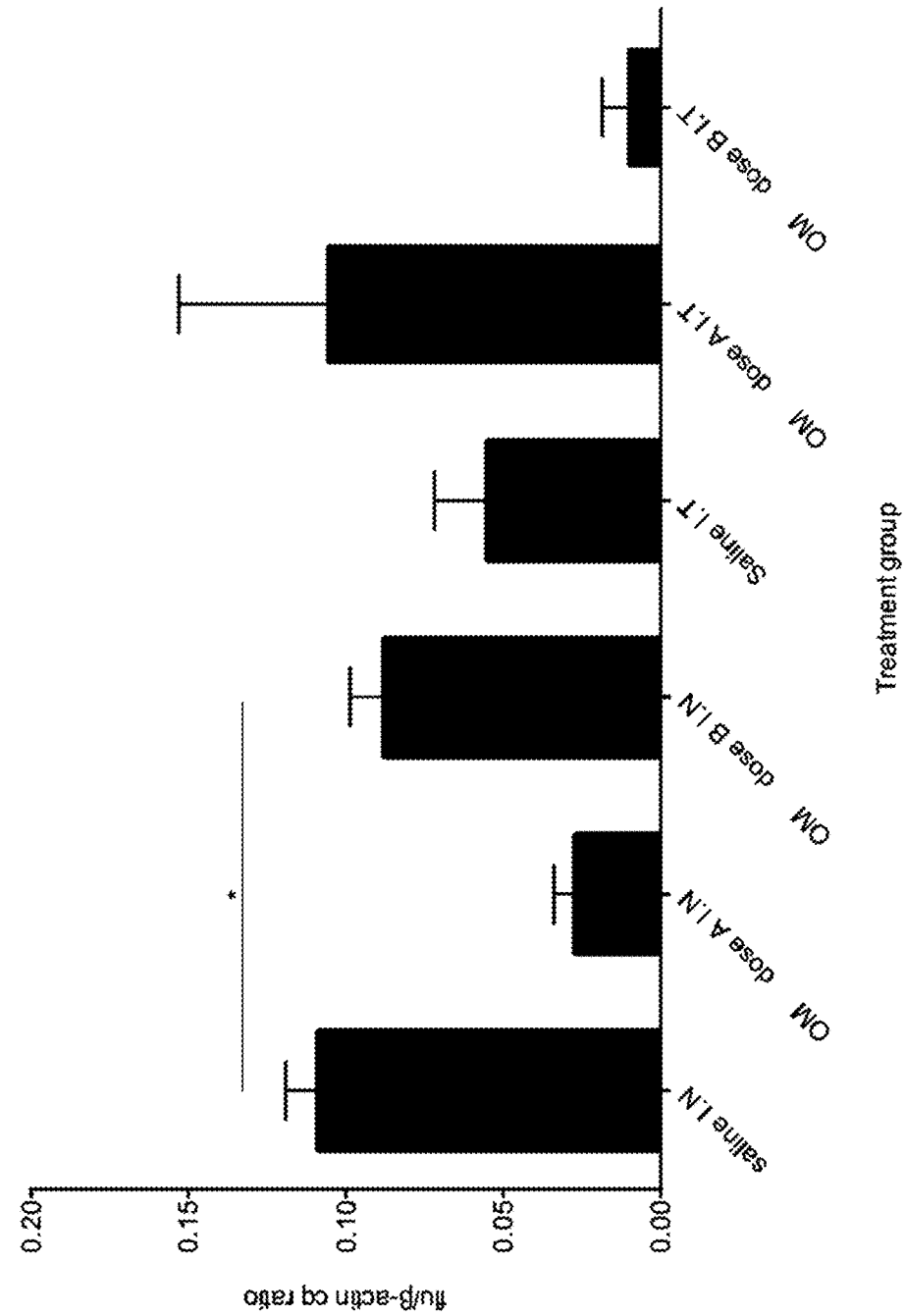
FIG. 8: is a graph showing the viral titer in lung tissue after day 5 post OM bacterial extract at doses A (50 micrograms) and B (5 micrograms) via intranasal (i.n.) and intratracheal (i.t.) administrations versus intranasal (i.n.) and intratracheal (i.t.) saline controls.

Curve comparisons were made for survival (FIGS. 8 and 10).

Prophylactic treatment of animals via intranasal administration of OM bacterial extract (OM dose B I.N.: 5 microgram and OM dose A I.N.: 50 microgram doses) yielded in a reduction of viral titer in the lung tissue measured at 5 days post-PR8 infection (FIG. 8). This reduction was more predominant in 50 microgram dose OM bacterial extract by intranasal route while 5 micrograms was enough to clear viral particles by the intratracheal route.

Figure 9:
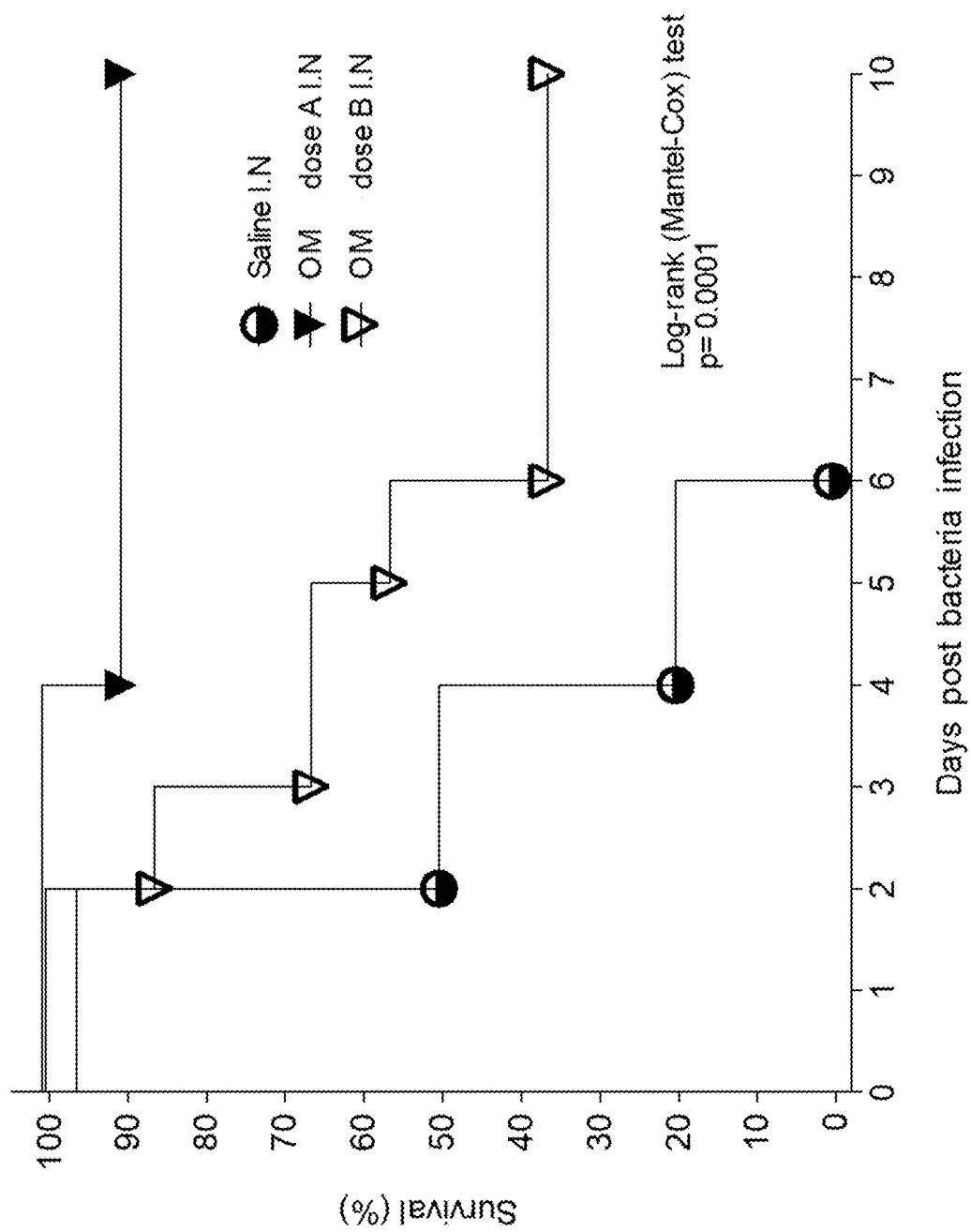
FIG. 9: is a graph showing the survival rate of mice treated by intranasal route with OM bacterial extract with 50 micrograms (dose AIN) and 5 micrograms (dose BIN) or with saline (IN.).

Similar to the viral titer results, prophylactic intranasal OM bacterial extract treatment yielded a significant alleviation of morbidity and mortality following post-influenza bacterial infection. The 50 microgram dose OM bacterial extract per nasal treatment yielded 90% survival (OM dose A I.N.), 5 microgram dose OM bacterial extract per nasal treatment yielded 40% survival (OM dose B I.N.), whereas saline control per nasal (saline I.N.) treatment did not protect the animals who died day 6 post infection (FIG. 9). Comparable to the survival results, clinical score and weight loss measurements were significantly reduced in animals treated with a 50 microgram dose of OM bacterial extract compared to saline treated animals (FIG. 9). In line with the 50 microgram dose OM bacterial extract treated animals, 5 microgram dose treated animals also presented a reduced clinical score and weight loss compared to saline control animals; however with lower efficacy for the 5 microgram intranasal dose.

Figure 11:
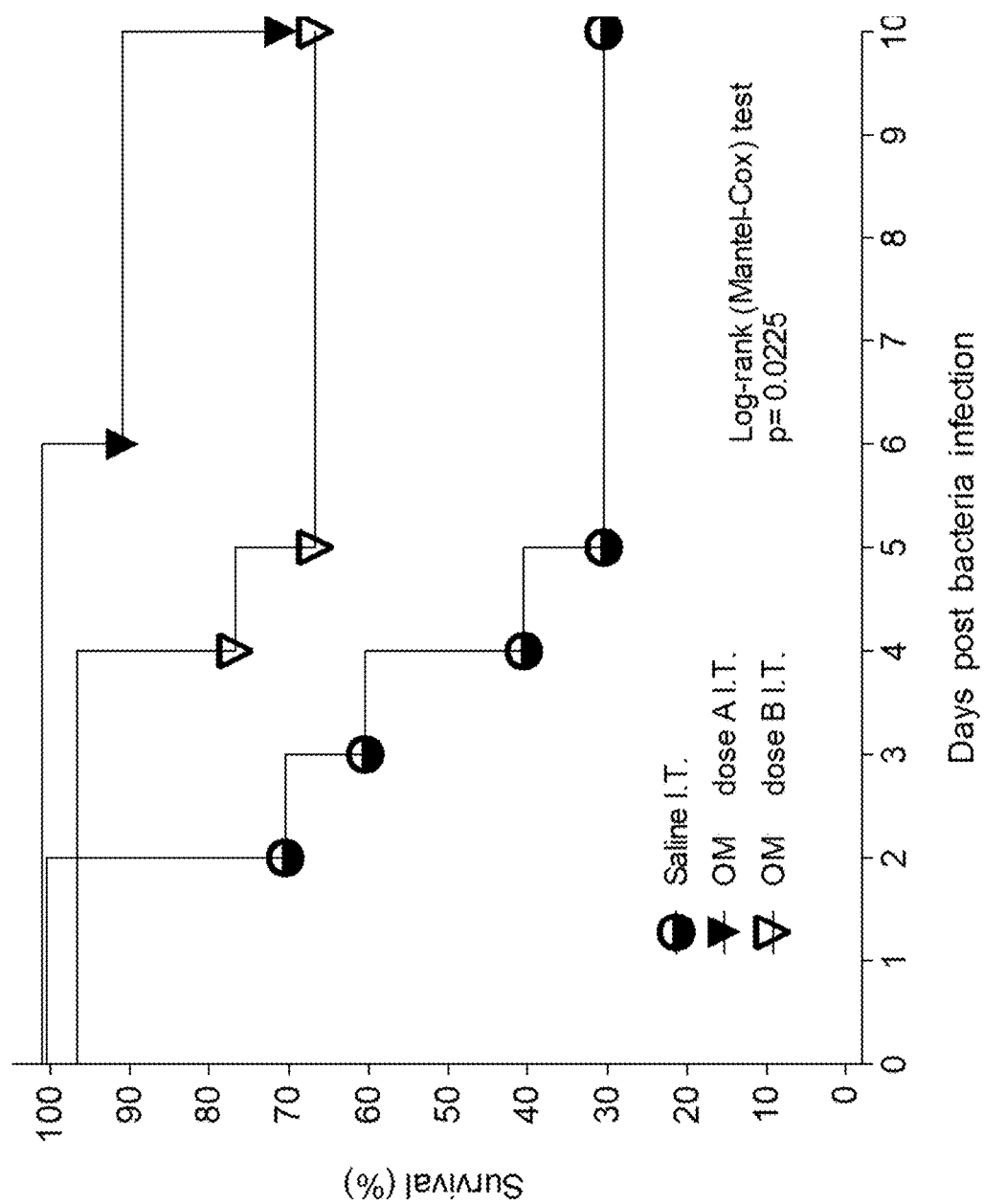
FIG. 11: is a graph showing survival of mice after administration of OM bacterial extract or saline following intratracheal route. 50 micrograms (dose A I.T) and 5 micrograms (dose B IT) OM bacterial extract.

Prophylactic 5 microgram dose OM bacterial extract intratracheal treatment of animals yielded the best reduction of viral titer in the lung tissue measured at 5 days post-PR8 infection compared to viral titer measurements found in control saline intratracheal treated animals (FIG. 8). With regards to morbidity and mortality, both intratracheal 50 microgram dose (OM dose A I.T.) and 5 microgram dose (OM dose B I.T.) of OM bacterial extract treatment yielded in an increased survival rate (70%) compared to saline control treated animals (30%) with a dose proportional effect up to day 10. (FIG. 11). This is summarized with the clinical score measurement equally reduced for both, intratracheal 50 microgram and 5 microgram doses of OM bacterial extract treated animals, compared to the saline control group (FIG. 12).

In summary, prophylactic per nasal OM bacterial extract administration resulted in a significant reduction of morbidity and mortality of super-infected animals and in reduced viral titer in lung tissue following influenza infection. This result was particularly clear following a 50 microgram dose OM bacterial extract treatment regimen administered via intranasal route. Surprisingly, prophylactic intratracheal OM bacterial extract treatment resulted in the best alleviation of morbidity and mortality with higher efficacy using the 5 microgram dose which could be explained by the deeper surface lung exposure.

Figure 13:
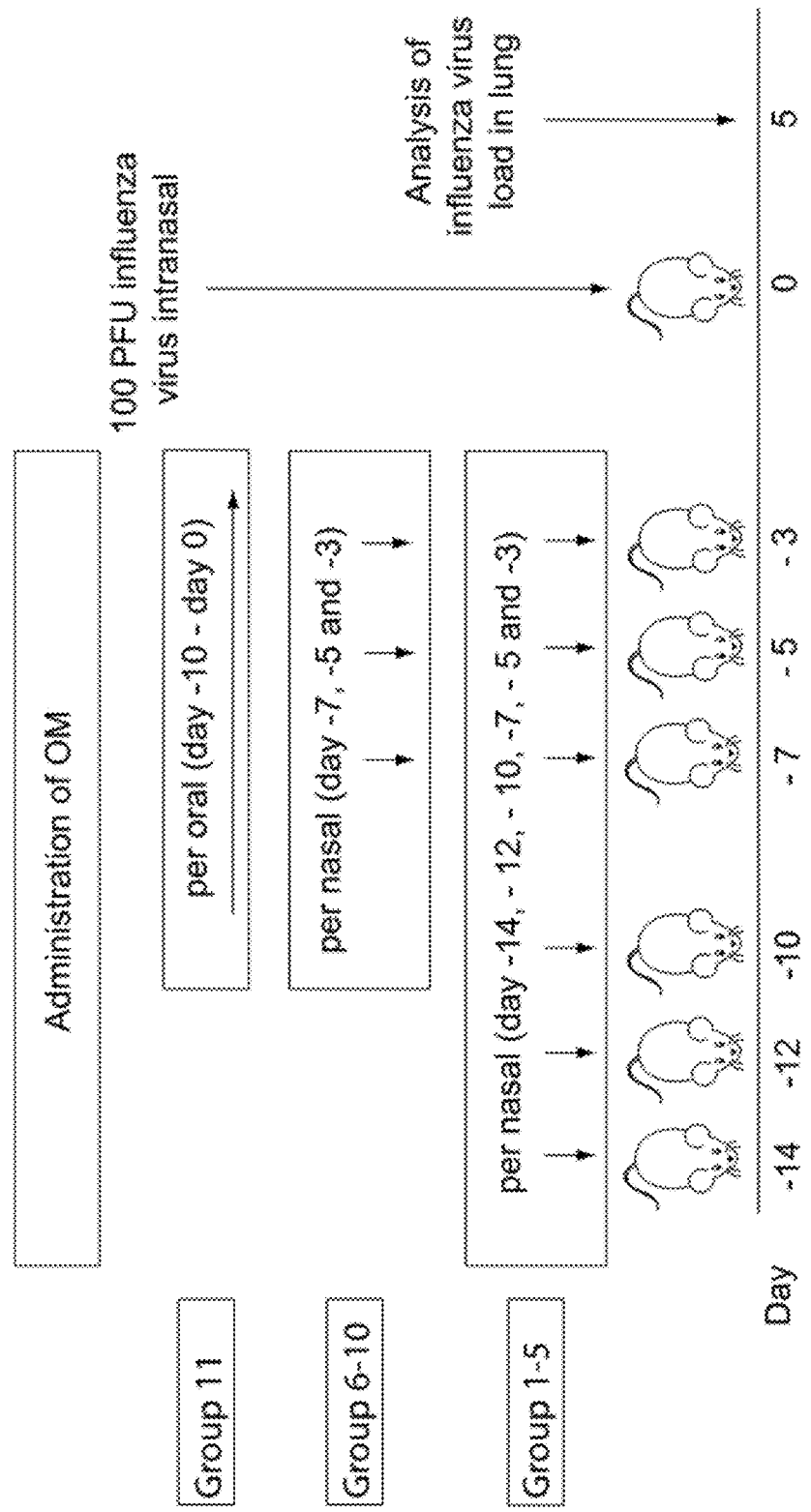
FIG. 13: shows the study design of a superinfection experiment: viral lung infection followed by bacterial lung infection using different doses and regimens following intranasal (per nasal) and per oral administration of OM bacterial extract compared to control group followed by the analysis of influenza virus load in the lungs. Groups 1 to 11 are described in Table 6.

These results clearly demonstrated that both intranasal and intratracheal administrations were highly efficacious routes of administration for OM bacterial extract therapeutic treatment for respiratory diseases, such as asthma, COPD and other pathogens.

acclimatized to facility for 7 days prior to initiation of study (Study Day 0). Animals were 8 weeks old on Study Day 0. Potable water and food were available ad libitum. Mice were divided into 13 groups: Groups 1 to 11 received active substance OM bacterial extract (OM) intranasally. Group 12 was water control (320 L water control, per oral, daily, day −10 to day −1) and Group 13 was negative control (sub-lethal influenza viral infection only). Tables 25 and 26 show the different groups and treatment protocols schematized in FIG. 13.

TABLE 25

| Group | Treatment groups dose/schedule/route |
|---|---|
| 1 | 2.5 microgram, d−14, −12, −10, −7, −5, −3, intranasal |
| 2 | 5 microgram, d−14, −12, −10, −7, −5, −3, intranasal |
| 3 | 25 microgram, d−14, −12, −10, −7, −5, −3, intranasal |
| 4 | 50 microgram, d−14, −12, −10, −7, −5, −3, intranasal |
| 5 | 100 microgram, d−14, −12, −10, −7, −5, −3, intranasal |
| 6 | 2.5 microgram, d−7, −5, −3, intranasal |
| 7 | 5 microgram, d−7, −5, −3, intranasal |
| 8 | 25 microgram, d−7, −5, −3, intranasal |
| 9 | 50 microgram, d−7, −5, −3, intranasal |
| 10 | 100 microgram, d−7, −5, −3, intranasal |
| 11 | 7.2 mg per-oral, daily, day −10 to day −1 |

TABLE 26

| Group | Drug | Route | Day of administration prior to viral infection | Volume per administration (microliter) | Active Principle (microgram) | Volume of concentrated drug solution used to yield in targeted amount of active principles per administration | Saline solution (microliter) |
|---|---|---|---|---|---|---|---|
| 1 | OM | i.n. | −14, −12, −10, −7, −5, −3 | 50 | 2.5 | 0.11 | 49.89 |
| 2 | OM | i.n. | −14, −12, −10, −7, −5, −3 | 50 | 5 | 0.22 | 49.78 |
| 3 | OM | i.n. | −14, −12, −10, −7, −5, −3 | 50 | 25 | 1.1 | 48.9 |
| 4 | OM | i.n. | −14, −12, −10, −7, −5, −3 | 50 | 50 | 2.2 | 47.8 |
| 5 | OM | i.n. | 14, −12, −10, −7, −5, −3 | 50 | 100 | 4.4 | 45.6 |
| 6 | OM | i.n. | −7, −5, −3 | 50 | 2.5 | 0.11 | 49.89 |
| 7 | OM | i.n. | −7, −5, −3 | 50 | 5 | 0.22 | 49.78 |
| 8 | OM | i.n. | −7, −5, −3 | 50 | 25 | 1.1 | 48.9 |
| 9 | OM | i.n. | −7, −5, −3 | 50 | 50 | 2.2 | 47.8 |
| 10 | OM | i.n. | −7, −5, −3 | 50 | 100 | 4.4 | 45.6 |
| 11 | OM | p.o. | daily, −10 to −1 | 320 | 7200 | 320 | N/A |
| 12 | water | p.o. | daily, −10 to −1 | 320 | N/A | N/A | N/A |
| 13 | N/A | N/A | N/A | N/A | N/A | N/A | N/A | i.n. = intranasal; p.o. = per oral

Example 6: Novel Treatment Regimen for Intranasal Administration of Bacterial Extract According to the Present Invention in an Animal Model of Sub-Lethal Influenza Infection This study (FIG. 13) showed the efficacy of intranasal administration of extemporaneously prepared OM bacterial extract (bacterial extract from 21 strain lysates) in reducing viral titer in lung tissue after influenza viral infection. This study also evidenced a dose-response relationship of OM bacterial extract. This study further provided with a comparison of two different multiple-dose regimen (a 6-dose and a 3-dose), and with a comparison between intranasal treatment regimen and per oral administration. Female 7-week-old BALB/c mice (Specified Pathogen Free; SPF) were purchased from Charles River Laboratories and randomly allocated to cages totally 5 mice per cage. Mice were monitored weekly and On the days specified in the Study Protocol, above, mice were anesthetized utilizing a calibrated vaporizer system (VIP300, Provet, Vet.Med Center, Lyssach, CH) delivering the anesthetic agent, isofluoran Provet AG, Catalogue number: 2222) into a plexiglas chamber containing the mice. Anesthetized animals were then administered with a total volume of 50 microliter of OM bacterial extract test material, which was trickled over both nostrils utilizing a 100 ul micropipette.

The virus material (Influenza virus strain PR8 (A/Puerto Rico/8/34, H1N1) sourced from Virapur (San Diego)) was stored at −75° C.±10° C. and was defrosted prior to administration. Once defrosted, the material was diluted in cold PBS (4° C.) corresponding to 100 PFU/50 µl for A/PR/8/34. The diluted virus was kept on ice until administration to the mice. The animals were anaesthetized by intraperitoneal injection with 9.75 mg Xylasol and 48.75 mg Ketasol per kg body weight and each animal received 50 µl virus solution by intranasalinoculation.

On days 5 animals were sacrificed by lethal intraperitoneal injection with pentabarbitol (Streuli Pharma AG, Uznach, Cat: 1170139A) immediately followed by tissue isolation (lung). Lung lobes isolated were prepared for the quantification of viral load in lung tissue by quantitative PCR. Lung lobes isolated and RNA was prepared with TRI Reagent (Molecular Research Center) and then treated with DNase (Invitrogen) to avoid genomic DNA contamination before RNA was converted to cDNA by reverse transcription using SuperScript III (Invitrogen). cDNA was quantified by real-time PCR (iCycler; Bio-Rad) using SYBR Green (Stratagene) and samples were normalized with GAPDH expression levels. All graphs were generated with Graphpad Prism Version 6 and a one-way ANOVA was applied. Error bars represent Standard Error of the Mean (SEM).

Figure 14:
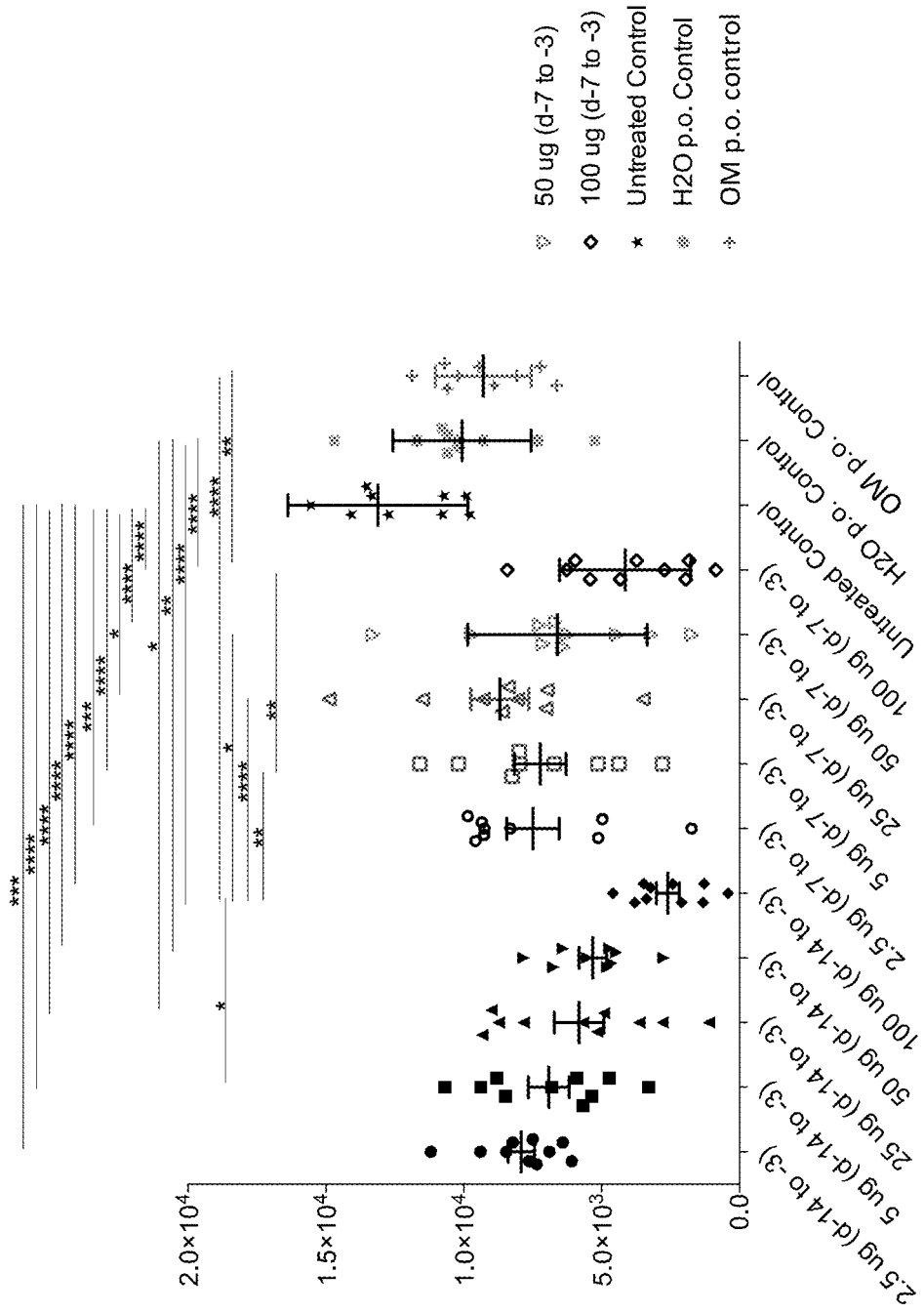
FIG. 14: is a graph showing the viral titer in lung tissue at day 5 post infection after preventive intranasal treatments with OM bacterial extracts and compared to oral treatment.

Results of this study clearly showed that intranasal administration of OM bacterial extract effectively protected mice against infection with influenza virus at any doses used in the study and with higher efficacy by intranasal route when compared with per oral route (FIG. 14). Compared to the untreated control, there was an apparent improvement of control of the virus in both the water and OM bacterial extract per oral groups. Furthermore, this protective effect was significantly dose dependent, from 5 microgram up to 100 microgram, the latest the highest dose assessed in this experiment. The groups receiving six rounds of intranasal administration of OM bacterial extract showed the best efficacy with the least variation, although mice which were administered OM bacterial extract only three times were also significantly protected against the virus. These data clearly confirmed previous experiments following intranasal administration demonstrating that OM bacterial extract provides the most efficacious route of administration. Since a clear dose response was evidenced with both 3 and 6 treatments of OM bacterial extract, one can conclude that this dose and regimen matter in this very effective prophylactic treatment against influenza in this mouse model. It can thus be anticipated that longer total treatment duration, higher frequency of perioral such as intranasal administration and higher doses are more effective.

Example 7: The Effects of the Bacterial Extract According to the Present Invention on the Expression of Rhinovirus Docking Proteins and on Type 1 and Type 2 Interferon Responses on Primary Human Epithelial Originating from Healthy Donors Previous data on the antiviral activity of extemporaneously prepared perioral OM bacterial extract (bacterial extract from 21 strain lysates) in human lung epithelial cells derived from healthy donors as well as COPD and asthma patient were published (Roth M et al, PLoS ONE 2017, 12(11), e0188010).

To follow-up anti-viral efficacy demonstrated in animal by OM bacterial extract via intratracheal route (direct lung exposure, examples 4, 5 and 6) the Applicant evaluated this direct lung exposure using primary bronchial epithelial cells from human lung origin (hBEC). To mimic results obtained in mice by the intratracheal route, human bronchial lung epithelial cells were directly exposed to new stable OM bacterial extract formulations from 21 strain lysates (OM314A (P1, P2, P3), OM314B (P4) and OM-314C (P5)) to assess anti-viral mounted efficacy response from lung cells. Considering the direct anti-viral effect on primary epithelial lung cells, these studies confirmed that lung is the primary target organ of OM bacterial extract as previously suggested by intranasal and intratracheal administrations in animals (Examples 4, 5 and 6).

In this study, Applicant evidenced on a molecular basis the results of cell exposition to OM bacterial extract and its protective effects on Rhinovirus infections. To this end, experiments on protein, mRNA expression and immunofluorescence were performed. Detection was conducted using ELISA and immunofluorescence techniques (direct cell counting with Trypan blue exclusion staining), as well as RT-PCR on human lung epithelial cell cultures originating from the lungs of several healthy donors, COPD patients and asthma patients.

BEC isolation and characterisation: small pieces of bronchial tissues (1×1×1 mm up to 2×2×2 mm) were placed into cell culture vessels, which were pre-wetted with BEC specific medium Cnt-PR-A (CellnTech, Bern, Switzerland). The medium was replaced every second day and cells were passaged by mechanical shaking of dividing cells. Cells were characterised by positive staining of E-Cadherin and Pan-Keratin, and negative staining for fibronectin (Roth M et al, PLoS One. 2017; 12:e0188010).

In this study, Applicant evidenced on a molecular basis the superior results of a selected set of new stable OM bacterial extract formulations and their preventive antiviral effects on Rhinovirus infection. Experimental readouts were quantitative viral load changes as well as anti-infective and anti-inflammatory mediators produced by hBECs, including but not limited to soluble mediators such as type 1- and type 2-interferon. These biological effects were measured by the following methods: mRNA detection by RT-PCR for viral load and detection of soluble mediator release by ELISA for type 1-interferon (IFN-beta and type II-interferon gamma). The determination of RV16 mRNA were performed for the different formulations listed in Table 27 with antiviral effect expressed as percentage mRNA to RV16 and mRNA expression rate of RV16.

Example 7.1: Antiviral Results

Figure 15:
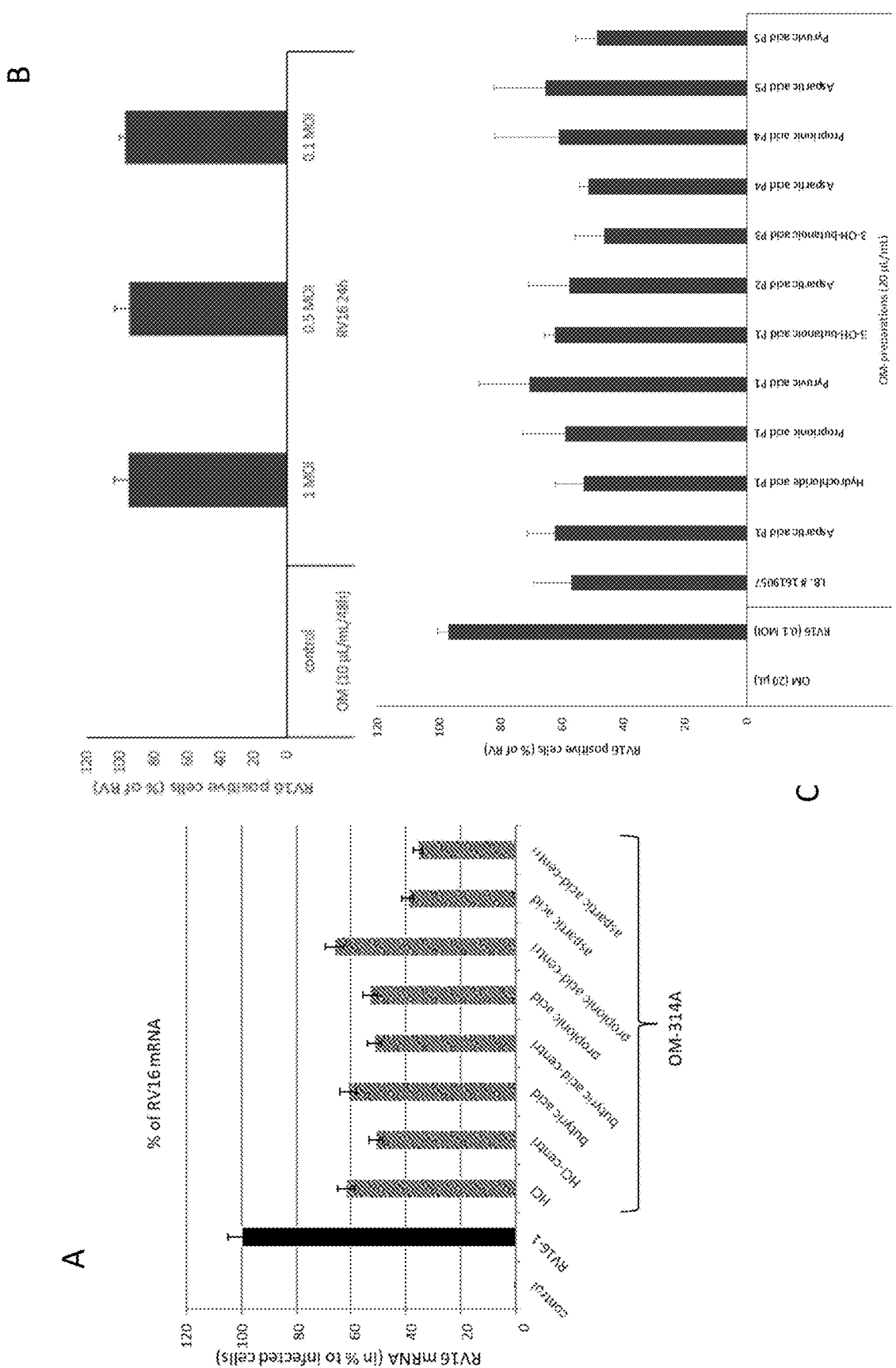
FIG. 15: Human Rhinovirus (RV16) infection rate in human primary bronchial epithelial cells (BECs) originating from lung biopsies of healthy donors pre-treated with various OM314A stable bacterial extracts. (A) Pre-treatment of B E C cells with OM314A containing organic acids or HCl was performed 1 day before infection with 1 Multiplicity Of Infection (MOI) RV-16. The mRNA Expression of RV-16 was used as an indicator of virus replication and expressed as relative value (percentage, FIG. 15A) versus RV16 (100%). Control 1 (0%) represented non-infected cells. RV16-1 represented BEC cells infected with RV16 for 24 hours. Bars represent mean±S.D. Samples tested: control 1, RV16; OM314A samples: HCL; 10 HCL centri.; butyric acid; butyric acid centri.; propionic acid; propionic acid centri.; aspartic acid; aspartic acid centri. Centri. indicates supernatant of the sample pair obtained after centrifugation and compared with its non-centrifuged counter pair. (B) RV16 protein positive human primary BECs (n=3) 24 hours after infection using 3 different viral concentrations. (C) Effect of pre-incubation (24 hours) with various OM314A preparations (20 μL/mL) on RV16 protein staining in BECs (n=3) 24 hours after infection with 0.1 MOI. Bars represent mean S.E.M.

Results obtained with the various new stable OM bacterial extract formulations tested (OM314A (P1, P2, P3), OM314B (P4) and OM-314C (P5)) show similar or improved antiviral effect over the standard OM bacterial extract HCl formulation (FIG. 15A). In this series, antiviral effects were tested with the new formulations where several acids were integrated into the manufacturing purification process (FIG. 15C). Compared to unstable liquid formulations labelled "HCl", new stable formulations demonstrated equivalent or better antiviral efficacy. Depending on the OM314A (P1, P2, P3), OM314B (P4) and OM-314C (P5) bacterial extract used and except in one case, equivalent or better efficacy than HCl formulation was demonstrated (compare percentage of RV16mRNA for HCL in FIG. 15A and I.B. in figure C with the other sample preparations).

TABLE 27

Percentage mRNA to RV16 and mRNA expression rate of RV16 corresponding to FIG. 15A

| Controls and OM314A | Percentage of RV16 mRNA | RV16 mRNA expression |
| --- | --- | --- |
| negative control | 0.18 | 0.0000016 |
| RV16-1 positive control | 100 | 0.0008809 |
| HCl | 61.7 | 0.0005436 |
| HCl-centri. | 51.0 | 0.0004492 |

TABLE 27-continued

Percentage mRNA to RV16 and mRNA expression rate of RV16 corresponding to FIG. 15A

| Controls and OM314A | Percentage of RV16 mRNA | RV16 mRNA expression |
|---|---|---|
| butyric acid | 61.0 | 0.0005377 |
| butyric acid-centri. | 51.6 | 0.0004546 |
| propionic acid | 53.2 | 0.0004687 |
| propionic acid-centri. | 66.1 | 0.0005820 |
| aspartic acid | 39.4 | 0.0003467 |
| aspartic acid-centri. | 35.6 | 0.0003136 |

Example 7.2: Type 1 and Type 2 Interferons

Figure 16:
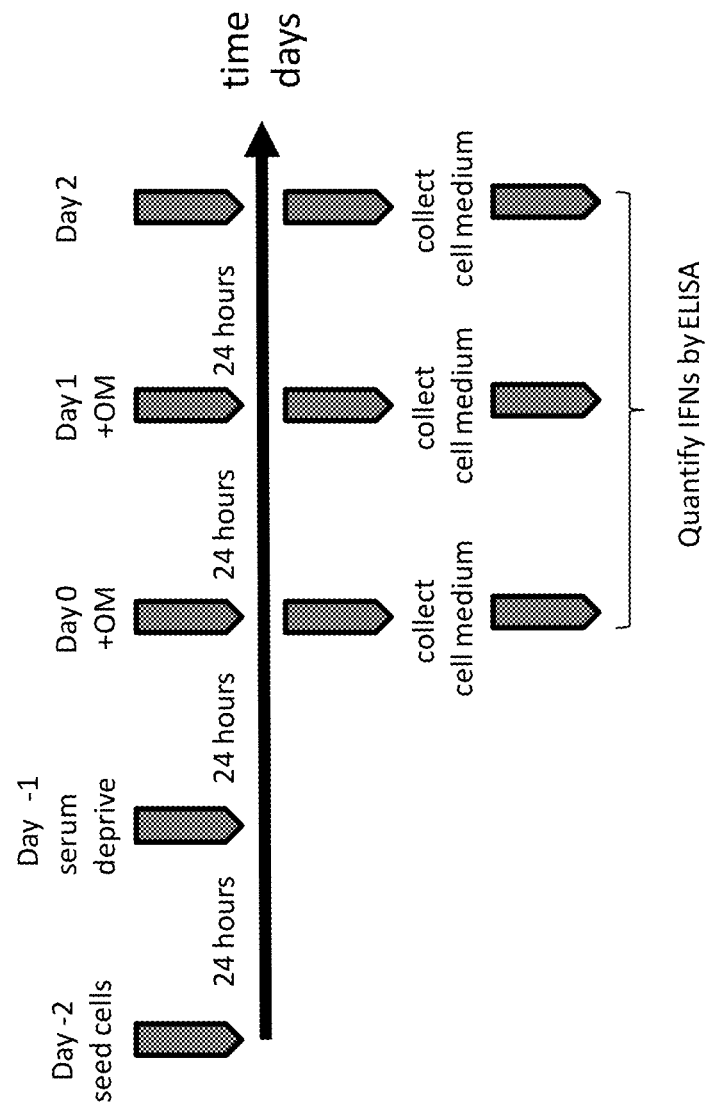
FIG. 16: Experimental scheme describing the protocol used to monitor interferon release from human BECs. Cells were seeded at Day-2, deprived from serum at Day-1 and stimulated for 24 h with OM314A samples (OM) as indicated in the FIGS. 17 and 18. Cell supernatants were collected at indicated times for the dosage of interferon beta and gamma using ELISA.

The induction of type 1 Interferon-beta production by the first generation of OM bacterial extract has been previously described in mice experimental cell models on primary bone marrow-derived dendritic cells (DCs) (Dang et al, Sci Rep. 2017 Mar. 6; 7:43844). Briefly, human BEC cells taken from healthy donors, asthma and COPD patients were seeded at Day-2, deprived from serum at Day-1 and stimulated for 0, 24 and 48 h with OM314A (P1, P2, P3), OM314B (P4) and OM-314C (P5) (concentration 10 microgram/mL) as indicated in the scheme (FIG. 16). Cell supernatants were then collected at indicated times for the dosage of interferon beta and gamma using ELISA.

Figure 17:
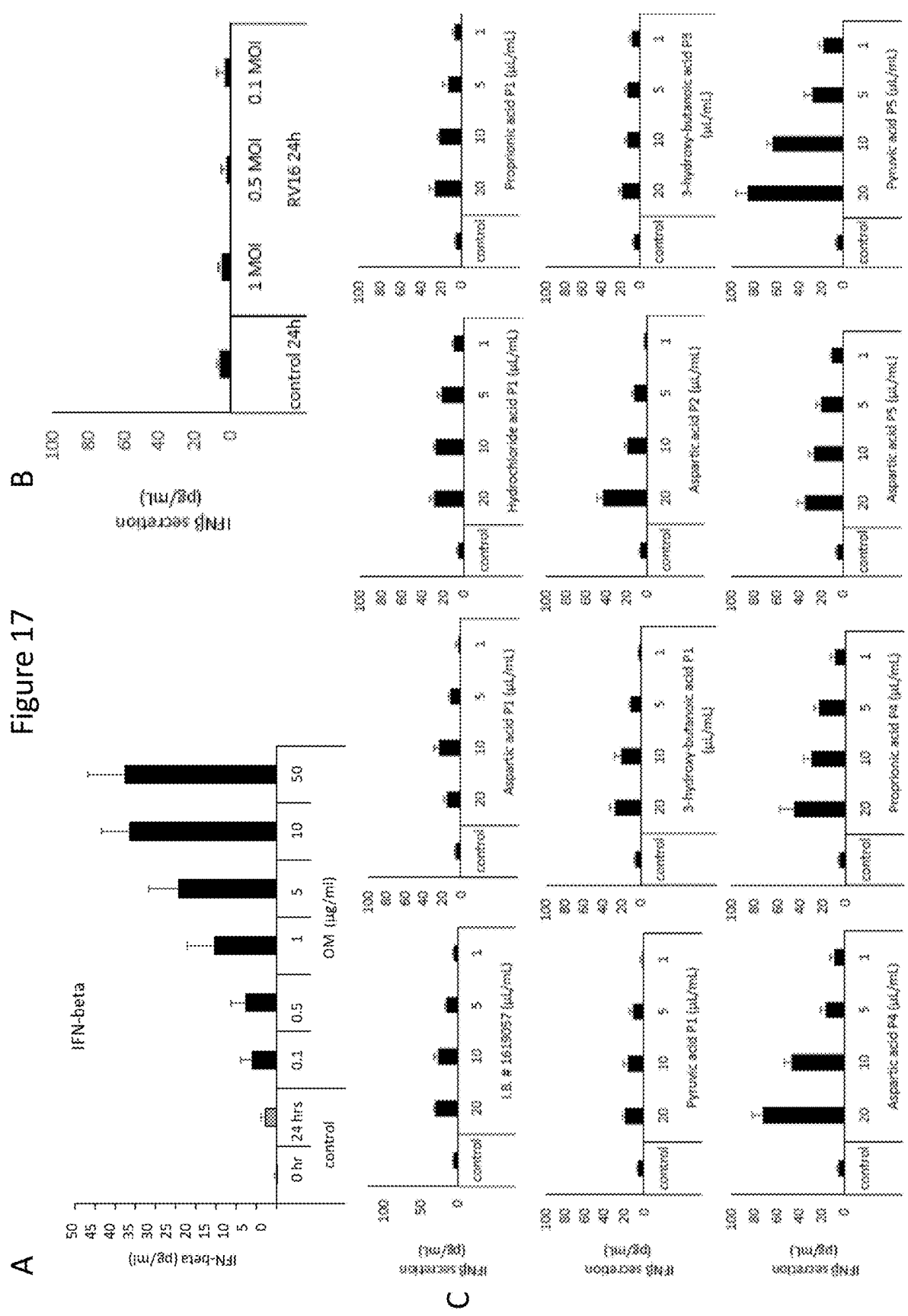
FIG. 17: (A) Dose response of type 1 interferon beta (IFN-beta) secretion by human BECs following 24 hours of incubation with OM bacterial extract neutralized with HCL (0.1 up to 50 microgram/ml). Bars represent mean of n=5 donors±S.D. *=p<0.01 compared to 24 hrs. (B) IFNβ secretion by human BEC (n=3) over 24 hours following RV16 infection. (C) Concentration-dependent effect of various OM314A (P1, P2, P3), OM314B (P4) and OM-314C (P5) preparations on the secretion of IFNβ by non-infected (n=3) human BECs. Bars represent mean±S.E.M of each condition.
Figure 18:
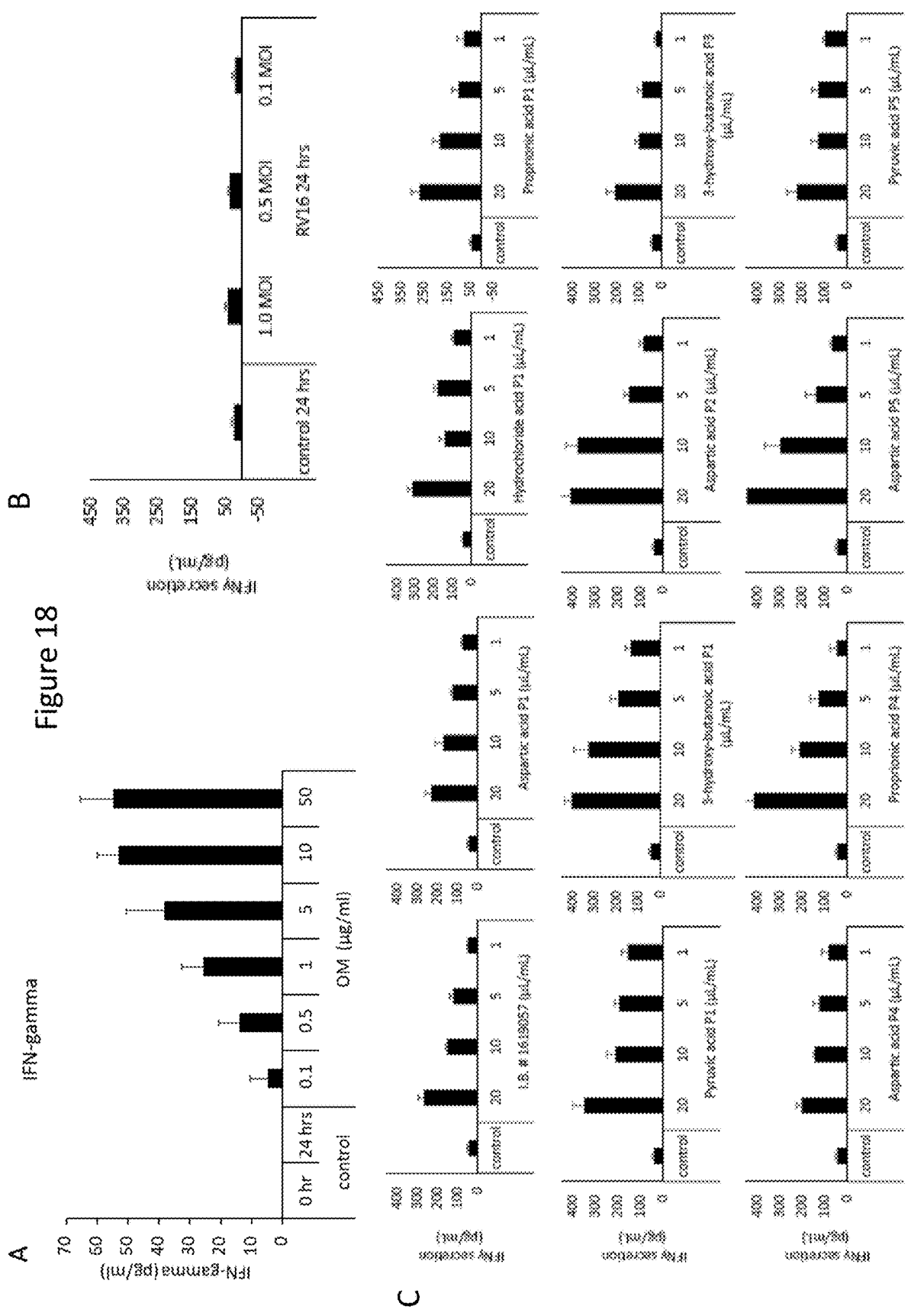
FIG. 18: (A) Dose response of type 2 interferon gamma (IFN-gamma) secretion by human lung-derived primary epithelial cell (BECs) following 24 hours of incubation with OM bacterial extract neutralized with HCL (0.1 up to 50 microgram/ml). Bars represent mean of n=5 donors± S.D. *=p<0.01 compared to 24 hrs controls. (B) IFNγ secretion by human BECs (n=3) over 24 hours following RV16 infection. (C) Concentration-dependent effect of various OM314A (P1, P2, P3), OM314B (P4) and OM-314C (P5) preparations on the secretion of IFNγ by non-infected human BECs. Bars represent mean S.E.M of each condition.

Compared to the original INF beta and gamma secretion by BECs using previous OM bacterial extract (FIGS. 17A and 18A, the newly OM314A (P1, P2, P3), OM314B (P4) and OM-314C (P5) stabilized product was able to induce type 1 Interferon beta and type 2 interferon gamma to similar or superior extend in FIGS. 17C and 18C (compare I.B. with the other product).Depending on the process used, some marked differences were observed. In this study, a dose range-induced interferon release of all OM314 stable bacterial extract was performed based on 5 donors. Mean interferon values of the 5 donors are shown in FIGS. 17B and 18B. Of note and in contrast to FIGS. 17A and 18A where IFNs-dependent release was obtained from OM bacterial extract concentrations, a maximum volume of 20 microliters was used in the FIGS. 17C and 18C, a volume corresponding to lower amount of the standard OM bacterial extract. Interferon alpha was neither induced by OM bacterial extracts nor induced by new stable OM314A (P1, P2, P3), OM314B (P4) and OM-314C (P5) on human BEC cells in vitro (not shown).

Example 8: The Protective, Anti-Viral Effects of the Bacterial Extract According to the Present Invention on the Changes of Expression of Beta β-Defensin-1 and ICAM-1 on Primary Human Epithelial Cells (BEC) Originating from Human Lung Biopsies Example 8.1: β-Defensin-1 and ICAM-1

As for EXAMPLE 8 and to further pursue in assessing the newly stable OM314A (P1, P2, P3), OM314B (P4) and OM-314C (P5) preparations following systematical comparison with previous data obtained with the original bacterial extract OM, we aimed at confirming previous data also published on human BECs but using other anti-viral hallmarks previously induced by OM bacterial extract (Roth et al. 2017). This is demonstrated in the FIG. 19 showing the capacity of newly stable OM314A (P1, P2, P3), OM314B (P4) and OM-314C (P5) preparations to induce anti-viral beta β-defensin-1 expression by human lung-derived primary epithelial cell (BECs) to the same or superior extend as the industrial batch (LB. #1619057). Identically, this anti-viral efficacy is also demonstrated with the decrease of the Rhino Virus ICAM-1 on the surface of these cells. The FIG. 20B shows the capacity of newly stable OM314A (P1, P2, P3), OM314B (P4) and OM-314C (P5) preparations to decrease ICAM-1 viral receptor expression by human BECs to the same extend as the industrial batch (LB. #1619057). Thus, in both cases confirming the capacity of this newly prepared stable bacterial extracts OM314 to maintain the potency and efficacy of the previous OM bacterial standards with similar or superior differences depending on the process, bacterial extract content.

Example 9: The Capacity of the Bacterial Extract According to the Present Invention to Activate the Adaptor and TLR-Dependent Effector Protein MyD88 Demonstrated and Monitored by the Release of TNFα from Mouse Bone Marrow-Derived Dendritic Cells Example 9.1: BMDC Preparation To further extend the investigation on the capacity of the newly prepared stable bacterial extracts OM314A (P1, P2, P3), OM314B (P4) and OM-314C (P5) to maintain the same or superior level of efficacy on the activation of innate immunity, we performed identical studies originally demonstrating the anti-inflammatory and modulatory effect of OM bacterial standards extensively exemplified in Dang et al. (Sci Rep. 2017 Mar. 6; 7:43844). To this end, one single but summarizing type of study was performed as it uses all necessary cellular component upon activation. A surface receptor (TLR), an effector protein mandatory for OM bacterial extract to induce protection (MyD88), and transcription factor to induce cytokine release upon its cleavage and translocation from the cytoplasm to the nucleus (NFkB) where transcription and cytokine release in the medium is measured (TNFα). To this end, primary bone marrow-derived dendritic cells were used from bones on mice. Bone Marrow (BM) cells were extracted from femurs and tibias of 6-10 weeks old wild-type C57/BL6 or various TLR knock-out mice (here shown only with TLR4 knockout (TLR4−/−) and WT mice) by flushing the bones with ice-cold PBS. Subsequent cell treatment of BMDM and their maturation and differentiation into dendritic cells (BMDC) was performed according to Dang et al. 2017. The purity of the culture was determined by staining the cells with anti-mouse CD11c and anti-mouse MHCII antibodies and the percentage of CD11c+MHCIIhigh cells was analyzed by flow cytometry.

Example 9.2: BMDC Stimulation and Measurement of Cytokine Release

Figure 21:
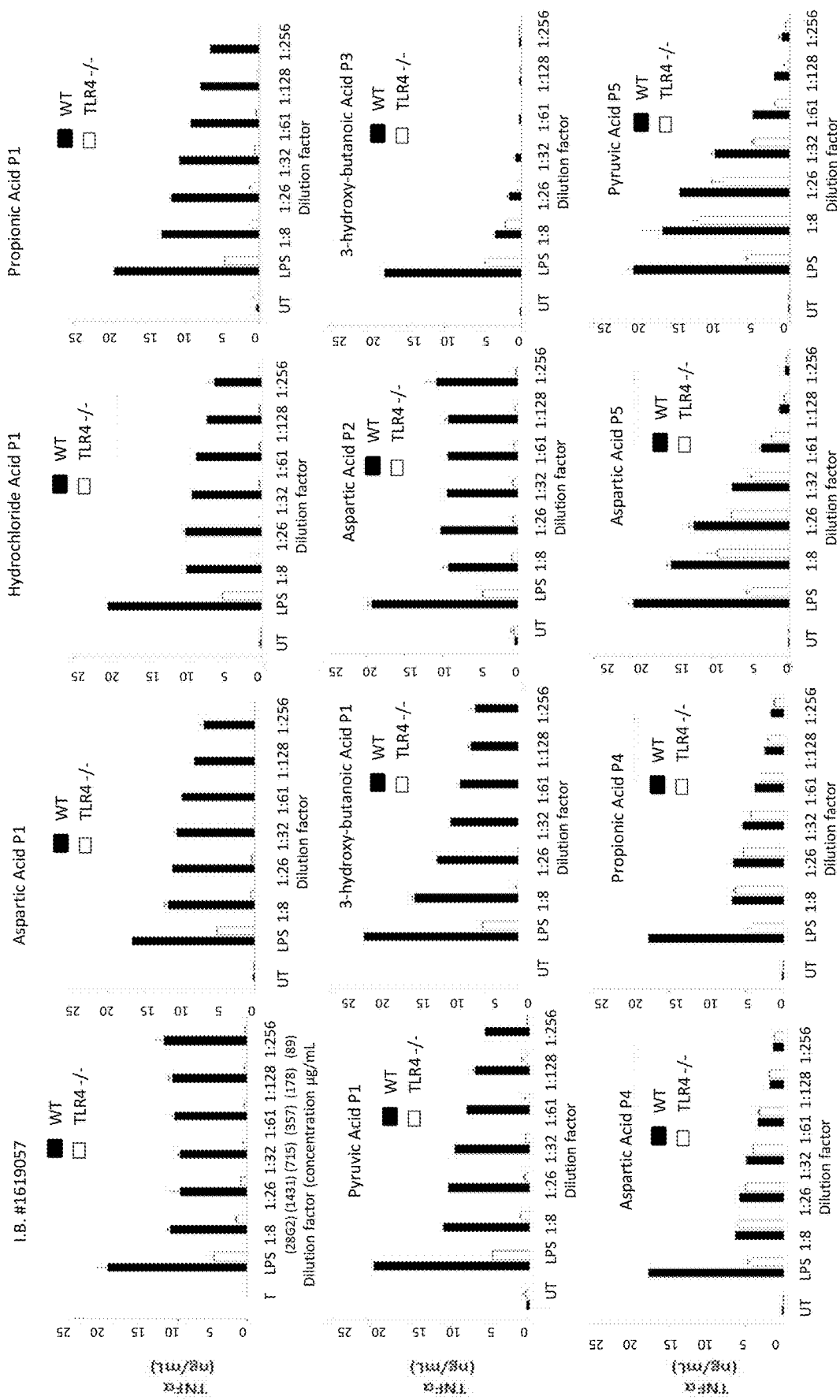
FIG. 21: Shows toll-like receptor (TLR)-4-dependent TNFα release from murine wild type (WT, black bars) or TLR-4 knock-out- (TLR4−/−, white bars) derived mouse Bone Marrow derived Dendritic Cells (BMDCs). Cells were stimulated with increasing dilutions of OM314A stable bacterial extract (P1, P2, P3), OM314B (P4) and OM-314C (P5) or with either LPS (2 μg/mL) or industrial batch (I.B #1619057) for controls using same set of dilutions. The level of concentrations of TNFα was measured in supernatants by ELISA following 16h of induction and according to manufacturer protocol.

BMDCs were plated in 96-well tissue culture plate at a density of $2\times10^5$ cells/well and stimulated for 16 h with LPS (4 µg/mL) from Enzo Life Sciences, or different concentrations of newly prepared stable bacterial extracts OM314A (P1, P2, P3), OM314B (P4) and OM-314C (P5). As reference in the FIG. 21, different concentrations (50-1600 µg/mL) of the Industrial Batch (LB. #16190560M) of the bacterial extract was used (upper left corner). Concentrations of TNF-α cytokine was measured in the cell-free supernatants by ELISA kits according to manufacturer's instructions using TNF-α kits from eBioscience, As this is exemplified in the FIG. 21, all newly prepared stable bacterial extracts OM314A (P1, P2), OM314B (P4) and OM-314C (P5) but one (3-hydroxy-butanoid-acid P3) were able to induce the secretion of TNF-α from BMDCs to the same extend as the control (LB.) from wild type normal mice. Interestingly, this secretion was either equivalent or better (dose-dependent) in some cases demonstrating the importance of the selective response of these different bacterial extract origins. Concomitantly, newly stable bacterial extract OM314A P3, P4 and P5 did not required TLR4 receptor to induce the release of TNF-α from BMDCs as this cytokine was also secreted in the absence of this TLR4 (TLR4−/−). LDA reveal that different organisms dominate different groups and that i) BE (bacterial extract from 21 strains lysates) prevents from deleterious bacterial groups in HFD mice and ii) increases group diversity EXAMPLE 10: The capacity of the perioral administration of bacterial extract according to the present invention to reverse gut dysbiosis in animals maintained on a High Fat Diet.

Example 10.1: The Importance of the Equilibrium of a Microbiota and Deleterious Consequences of Dysbiosis and Microbiome Analysis by Taxonomy Specific microbiota patterns are variable and dependent on many external factors such as diet, age, genetics, and medications (Dieterich et al. Med Sci (Basel). 2018; 6(4): 116. Published 2018 Dec. 14, doi:10.3390/medsci6040116). While research is still at the beginning of the era showing how the microbiome can contribute to the homeostasis, the elucidation of the precise mechanisms in which microbiome dysbiosis leads to certain medical conditions, the importance of maintaining a balanced microbiome is of paramount and urgent product are needed to restore such disequilibrium. Accordingly, restoration of an unfavorable population of intestinal flora to a favorable microbial ecosystem may prevent human disease (Young V B et al. BMJ 2017; 356: j831. In a study aimed at evaluating the lipotoxic effects of consumption of a high fat diet (HFD) in pregnancy, we have recently shown that consumption of a HFD for eight weeks leads to gut dysbiosis, oxidative stress, increased inflammation and increased risk of inflammation driven preterm birth (PTB). Accordingly, and in the present EXAMPLE, we set out to determine the ability of bacterial extract of the present invention to reverse HFD induced gut dysbiosis and associated harmful effects on metabolism and immune status. Results from taxonomy enabled the determination of Linear Discriminant Analysis (LDA) scores as indicated in the FIG. 22. This figure illustrates the bacterial lysate specific effect on specific micro-organisms. Undesirable Clostridiales, Firmucutes, Clostridia and Blautia species present in HFD control mice (HFD Sham) were restored in mice fed with bacterial extract (HFD-BE) and to a lesser extend also in the normal chow control diet mice (NCD-Sham). Furthermore, increase levels of desirable organisms that are depleted by consumption of a HFD were also identified in the microbiota content of mice fed with bacterial lysate (HFD-BE and NCD-BE). Unlike standard taxonomic analysis demonstrating increase and decrease of a selected set of species, the LDA score demonstrated in FIG. 22 illustrate distinct species of each of the 4 groups (NCD-Sham, NCD-BE, HFD-Sham, HFD-BE). LDA reveal that different organisms dominate different groups and that i) BE (bacterial extract from 21 strains lysates) prevents from deleterious bacterial groups in HFD mice and ii) increases group diversity, thus confirming the positive effect of the bacterial lysate from present invention.

Example 10.2: Methods, Animal, Food Consumption, Glucose Tolerance, Insulin Resistance and Diet Two different mouse strains were used throughout this study: C57BL/6 and CD1. C57BL/6 mice are an inbred strain with the advantage of being known to become obese, hyperglycemic and insulin resistant when fed a High Fat Diet (HFD). CD1 mice, on the other hand, have milder metabolic dysfunction after consuming a HFD, but have the advantage of being outbred, so any idiosyncratic response to the HFD will be avoided. Mice are purchased from Jackson Laboratories (Bar Harbor, ME, USA). An equal number of male and female mice of each strain are housed in individually ventilated cages in the Animal Care Center at 24° C., on a day and night cycle of 12 h each, and have ad libitum access to food and water. Diet with a 60% fat, high saturated fat content, fat derived primarily from lard and soybean oil are provided to HFD-mice and NCD containing 13.3% fat are provided to NCD-mice. Food and water are provided ad libitum. OM bacterial extracts are administered by perioral route by pipetting via intranasal route (0.05 mL) for 14 days or via oral route directly into the mouths (<0.15 mL) of the mice daily for four and eight weeks. Mice receiving "sham treatment" (negative controls) are administered by pipetting 0.05 mL of water (intranasal) once a day for 14 days or via oral route directly into the mouths (<0.15 mL) of the mice daily for four and eight weeks. Positive control. *Lactobacillus plantarum*, a probiotic that reverses gut dysbiosis is administered to positive control mice by adding 2×108 CFU/mL to their drinking water for six days. Analysis of OM bacterial extracts effects on gut microbiome: Fecal samples are collected and 16S rRNA are analyzed by sequencing. Following sequencing the functional genes in samples are characterized and differences between functional genes of microbial communities are analyzed using the Kyoto Encyclopedia of Genes and Genomes (KEGG) pathway analysis. Protein function classification of these genes is predicted using Cluster of Orthologous Group (COG) family information. Analysis of OM bacterial extracts effects on metabolic status: Glucose tolerance tests (GTTs) and insulin tolerance tests (ITTs) are performed on all mice at the beginning and at the end of the eight-week period. Mice are fasted for 8 h and then challenged with an intraperitoneal injection of 2.0 g/kg glucose with or without insulin and glucose levels will be measured at 0, 15, 30 and 60 min.

Figure 26:
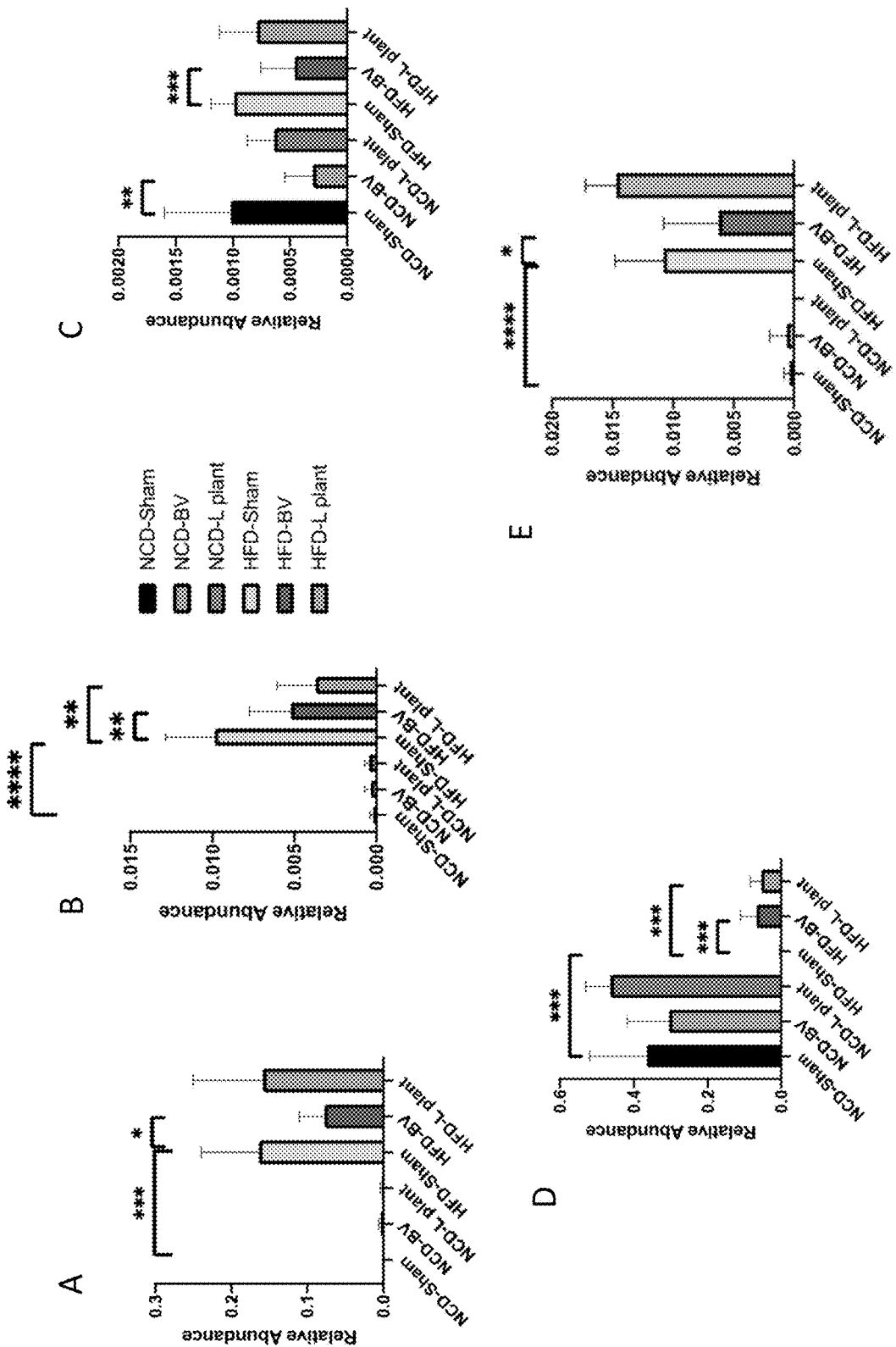
FIG. 26: shows the effect of bacterial extract from 21 bacterial lysates on various intestinal species. 16S ribosomal RNA sequencing and analysis were performed as described in the EXAMPLE 10. A. Clostridiales Lachnospiraceae blautia; B. Clostridia Clostridiales ruminococcaceae GCA-900066225; C. Clsotridiales Ruminococcaceae ruminococcaceae UCG-0101; D. Bacteroidales Muribaculaceae uncultured bacterium; E. Lachnospiraceaeae [*Eubacterium*] fissicantena group; $*p<0.05$, $p<0.01$, $*p<0.001$, $****p<0.0001$

Example 10.3: Effect of Bacterial Extract from 21 Bacterial Lysates (BE) on Various Genus As addendum and to populate further the data summarized in the FIG. 22, an example of several changes in genus induced by BE is demonstrated in the FIG. 26. In this example, BV demonstrated positive effect on deleterious genus (reducing growth) and simultaneously, favored growth on bona fide genus. Five examples are shown in this Figure. (A) BE reduces genus clostridiales lachnospiraceae blautia triggered by HFD; (B) BE reduces genus clostridia clostridiales ruminococcaceae GCA-900066225 induced by HFD; (C) BE reduces clostridiales Ruminococcaceae ruminococcaceae UCG-0101 in both NCD and HFD mice; (D) BE restores Bacteroidales Muribaculaceae uncultured bacterium depleted by HDF; (E) BE reduce Lachnospiraceaeae [*Eubacterium*] fissicantena group.

Example 11: The Capacity of the Perioral Administration of Bacterial Extract to Improve Glucose Tolerance Example 11.1: Testing Glucose Concentration Prior Diet of Bacterial Extract from 21 Strain Lysates (Pre-Diet), Post Normal Chow Diet Mice (Post-NCD), Post High Fat Diet (Post-HFD)

Figure 23:
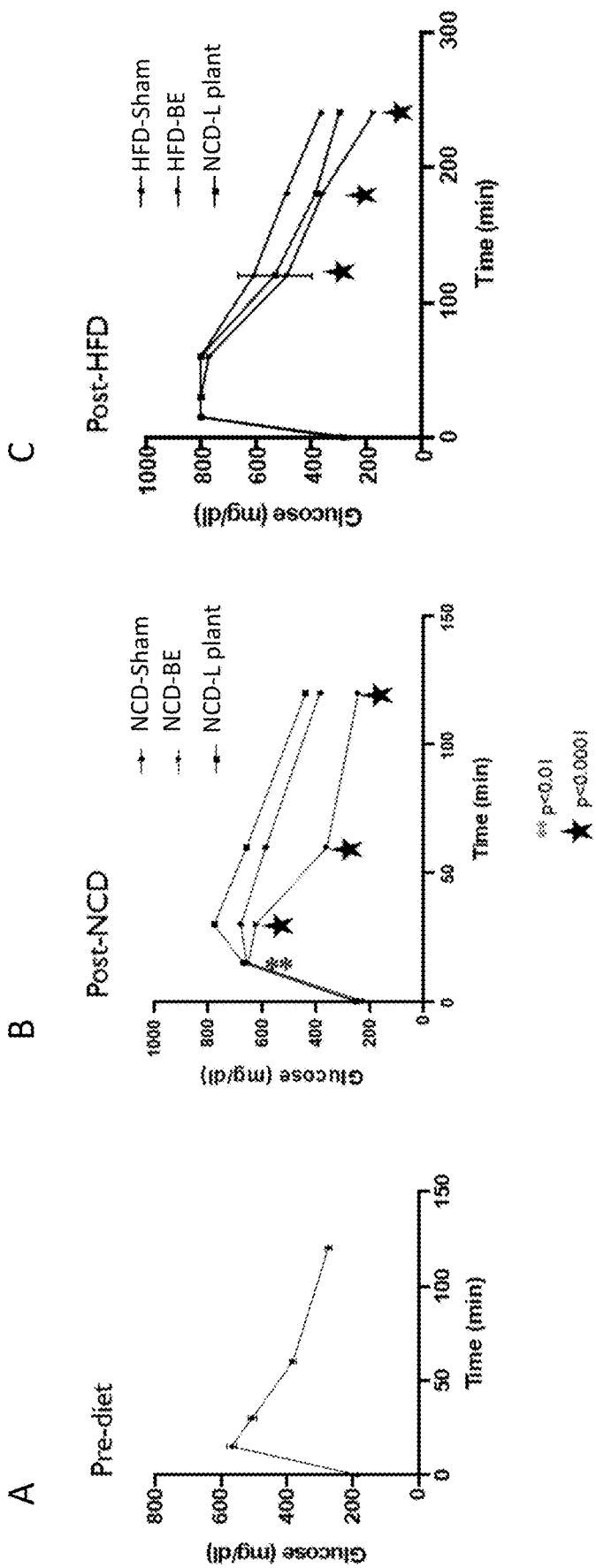
FIG. 23: (A) shows graphs of glucose concentration prior diet of bacterial extract from 21 strain lysates (Pre-diet), (B) post normal chow diet mice (Post-NCD), (C) post high fat diet (Post-HFD). For weight gain, mice were weighed once a week. Food consumption measures was assessed once a week by weighing the pellets at the beginning and end of the week. Large black and small stars significance marks are HFD-Sham compared to HFD-L. *Plantarum* and HFD-Sham compared to HFD-BE as indicated in the graphs and with respective significance values.

Further to correction of gut dysbiosis by bacterial extract, glucose tolerance was also investigated in these diabetic mice. This parameter is of paramount from clinical standpoint. The FIG. 23B, normal chow control diet mice fed with bacterial extract from 21 strain lysates (NCD-BE), but not L. *Plantarum* (normally used as positive control for improving the reorganizing of gut dysbiosis) significantly increased glucose tolerance as shown by lower glucose concentration. Identically, this effect was also demonstrated in high fat diet mice fed with bacterial extract from 21 strain lysates (HFD-BE), shown in FIG. 23C, albeit, to a lesser extent.

Example 11.2: Assessing Weight and Food Consumption

Figure 24:
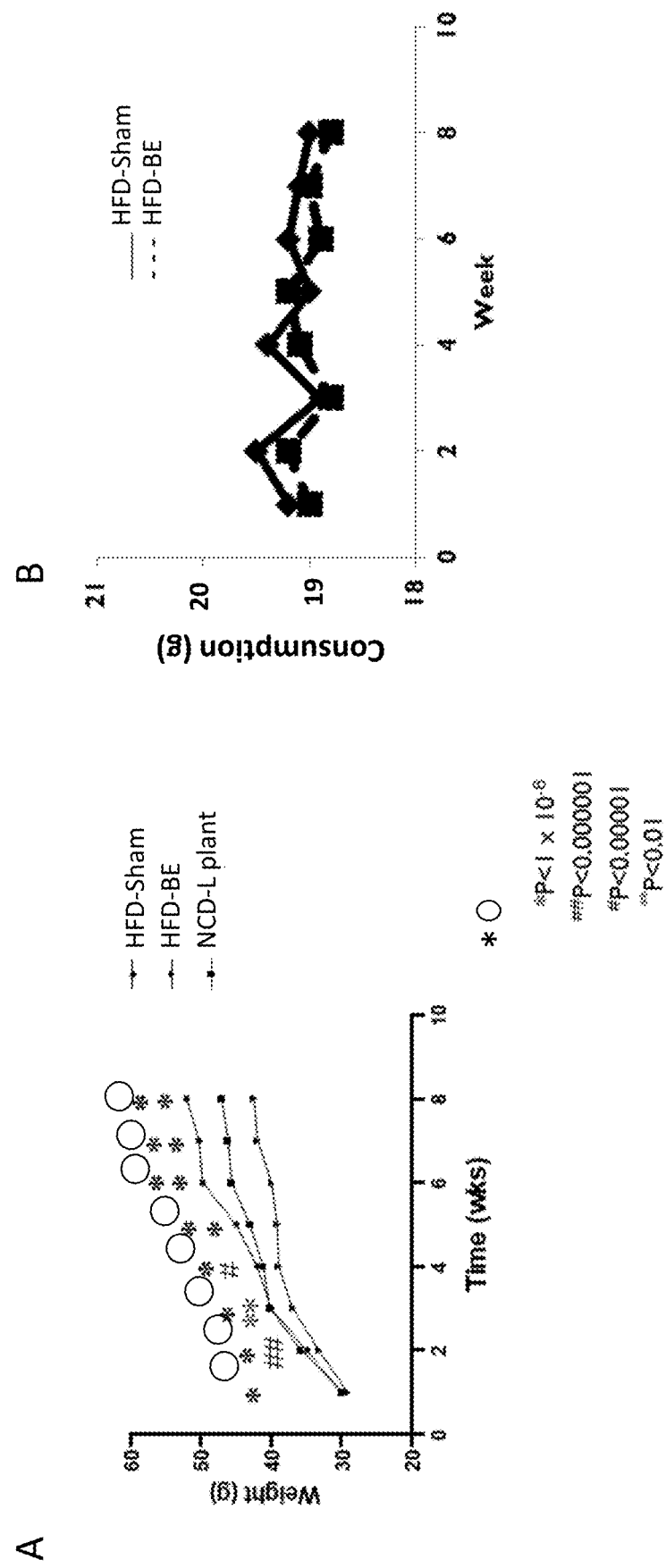
FIG. 24: shows weight and food consumption. (A) Shows weight in high fat diet sham control fed with saline solution (HFD-Sham), high fat diet treated with bacterial extract from 21 strain lysates (HFD-BE) and high fat diet treated with L. *Plantarum* (NCD-L plant) expressed in gram. (B) Shows food consumption comparison between high fat diet sham control fed with saline solution (HFD-Sham) and high fat diet treated with bacterial extract from 21 strain lysates (HFD-BE) expressed in gram. For weight gain, mice were weighed once a week. Food consumption measures was assessed once a week by weighing the pellets at the beginning and end of the week. Encircled stars significance marks are HFD-Sham compared to HFD-BE, Normal star significance * marks are HFD-Sham compared to HFD-L. *Plantarum* as indicated in the graphs and with respective significance values.

In the FIG. 24, both parameters were tested as control. The results show that high fat diet mice fed with bacterial extract from 21 strains lysates (HFD-BE) significantly decreases weight gain. This is exemplified in these high fat diet mice (FIG. 24A). Concomitantly, this absence of weight took place without affecting food consumption measured and expressed here as control (FIG. 24B). Interestingly, this effect was even more effective than *L. plantarum* normally used for such measure.

Example 11.3: Assessing Insulin Tolerance

Figure 25:
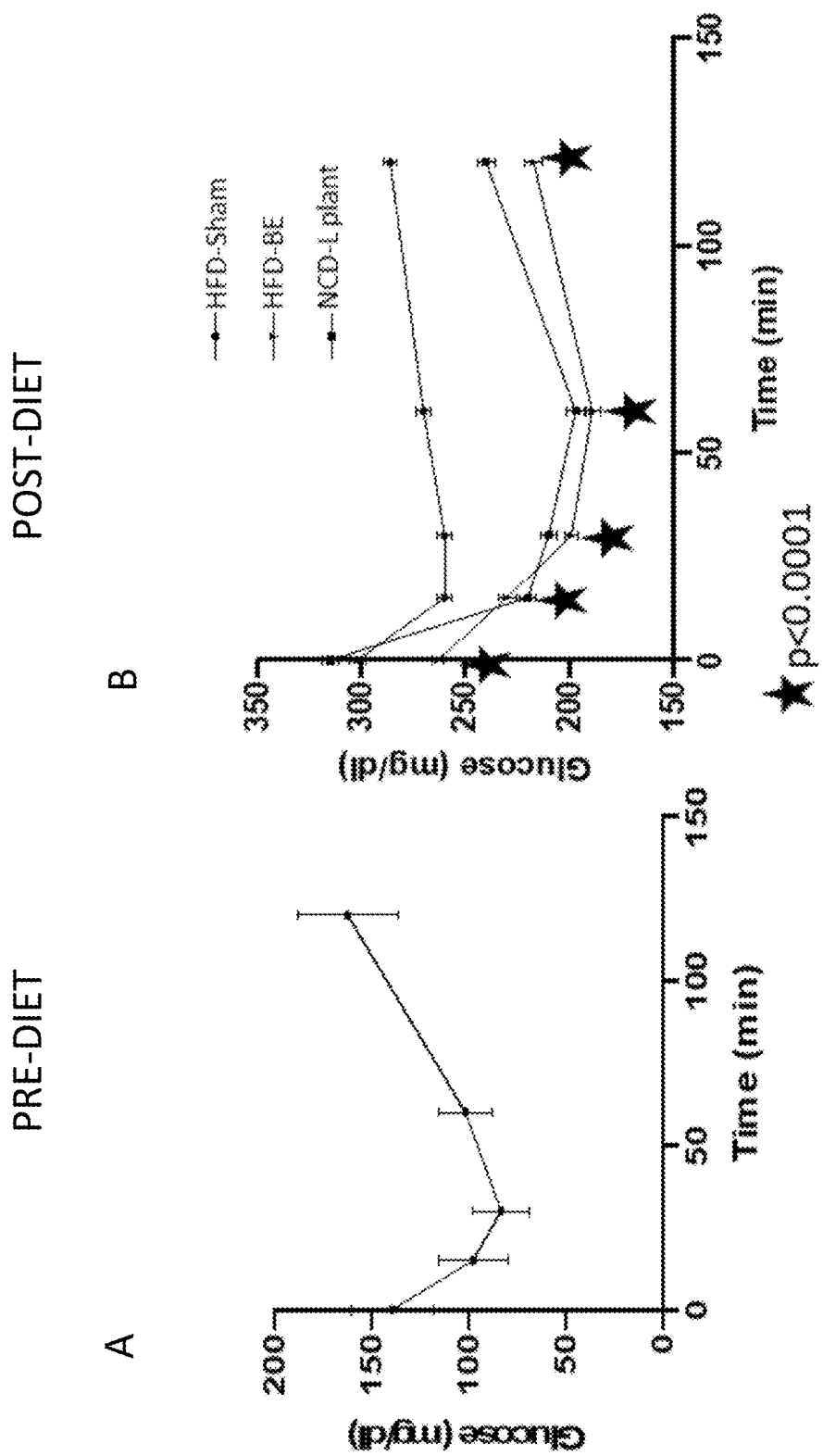
FIG. 25: shows the results of insulin tolerance tests in all 42 mice before treatment (PRE-DIET) and at the end of the eight-week treatment period (POST-DIET) in high fat diet (HFD) mice fed either with saline solution (HFD-Sham), bacterial extract from 21 strain lysates (HFD-BE) or with L. *Plantarum* (NCD-L plant). Plain black stars significance marks are HFD-Sham compared to HFD-BE as indicated in the graphs ($p<0.0001$).

Considering the protective results cited above on glucose tolerance obtained from treatment with bacterial extract from 21 strain lysates (BE) in diabetic mice exposed to high fat diet (HDF) regimen, we further investigated if the level of insulin was also modified to its protective end. FIG. 25 demonstrates the insulin tolerance in all mice (42) prior treatment (PRE-DIET) set as reference and after the last eight-week treatment period (POST-DIET) in high fat diet mice (HFD). As expected for normal chow mice fed with *L. plantarum* (NCD-L-plant.) showing a decrease insulin resistance (FIG. 25B), mice fed with HFD-BE bacterial extract from 21 lysates showed significantly, and for all time points, insulin resistance in the high fat mice. This protective effect by bacterial extract from 21 lysate is in line with the glucose data and the absence of weight gain from previous figures, all pointing towards a positive reorganization of the standard parameters measured in diabetic patients. Thus, confirming that bacterial extract from 21 strain lysates (BE) not only induced a protective gut dysbiosis in chronic HFD mice undergoing such regimen, but also its associated sequelae exemplified here with weight, glucose and insulin, all positively influenced towards protection by bacteria lysate of 21 strain lysates.

Example 12: In Vitro Efficacy of OM314A Bacterial Extract Against SARS-Cov2 Infection of Bronchial Epithelial Cells COVID-19 pandemic is caused by SARS-CoV-2, which, among several organs infects epithelial cells by binding to the surface protein angiotensin converting-enzyme 2 (ACE2). We were able to demonstrate that the OM314A bacterial extract according to the present invention significantly improve the anti-viral defense of bronchial epithelial cells (HBEC).

Example 12.1: Methods

HBEC cell lines (BEAS-2B, Nuli-1) were grown to 85% confluence, before being exposed to OM314A bacterial extract dilutions (1:100, 1:50, 1:10) for 1-5 days. RNA and Protein samples were collected and analyzed by RT-PCR and Western-Blot for ACE2 and associated proteins TMPRSS2, ADAM17, and DPP4, as well as for epithelial differentiation marker: E-Cadherin.

Example 12.2: Results

Figure 33:
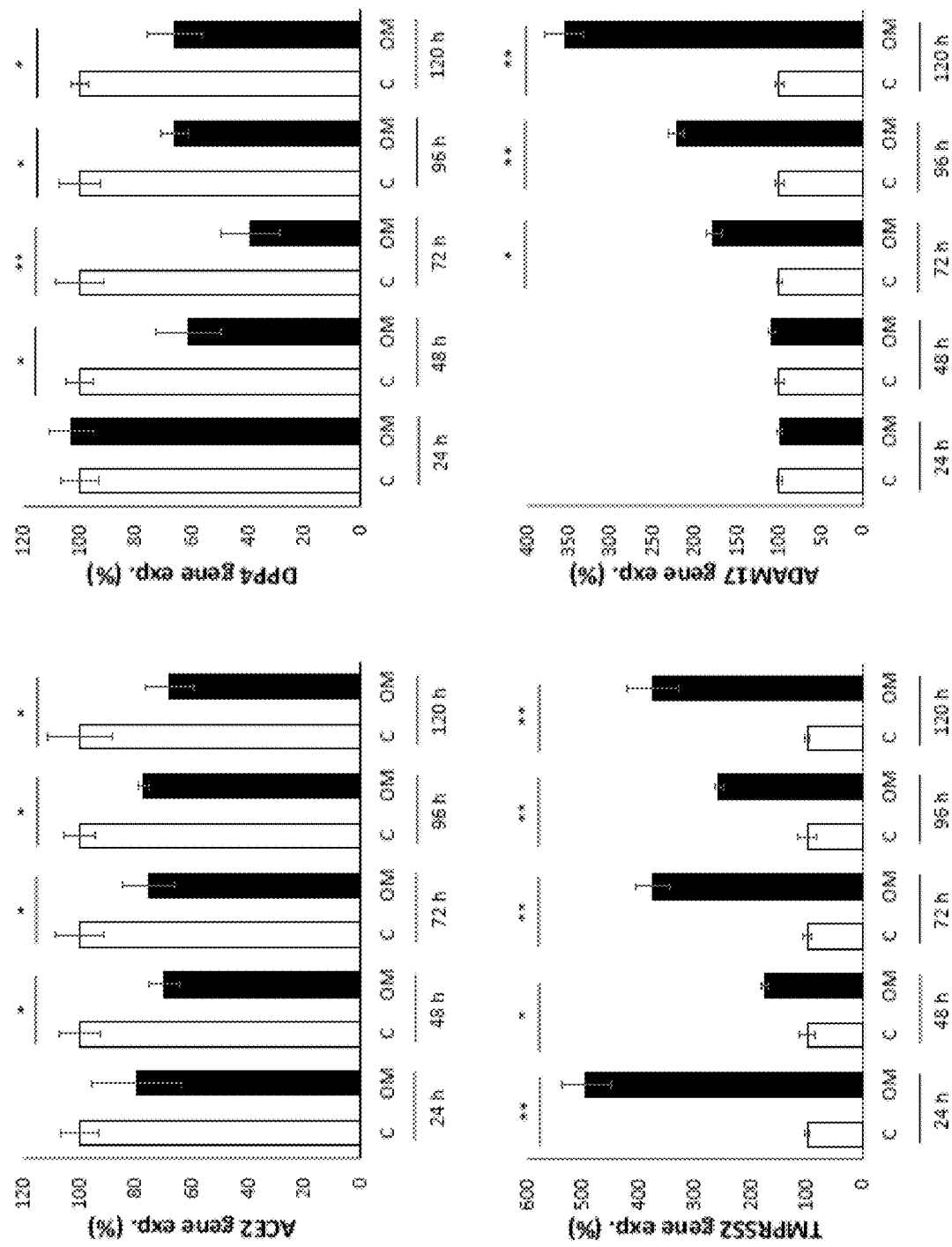
FIG. 33: RT-PCRs showing the impact of treatment with OM314A bacterial extract (OM), compared to negative control (C), on the ACE2, TMPESS2, DPP4, and ADAM17 gene expressions in HBEC cells (n=6, $*p<0.05$, $**p<0.01$, Student t-Test).
Figure 34:
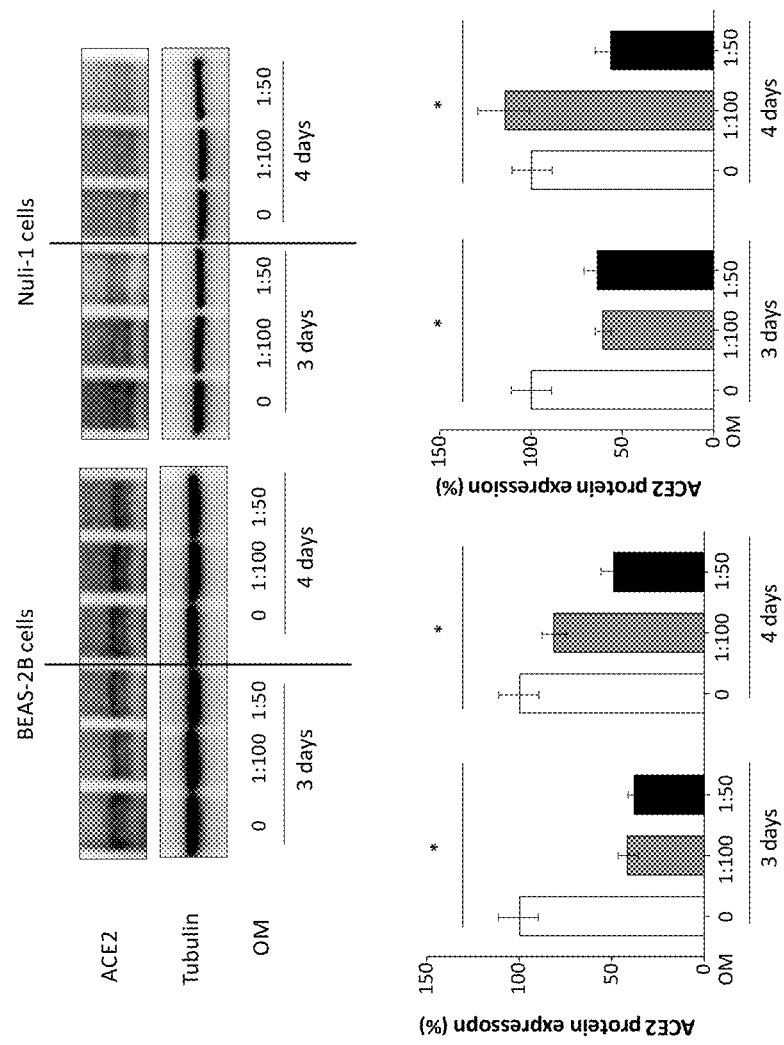
FIG. 34: are Western blots showing that treatment with OM314A bacterial extract (OM) decreased HBEC cells ACE2 protein expressions (n=3, $*p<0.05$, ANOVA test).
Figure 35:
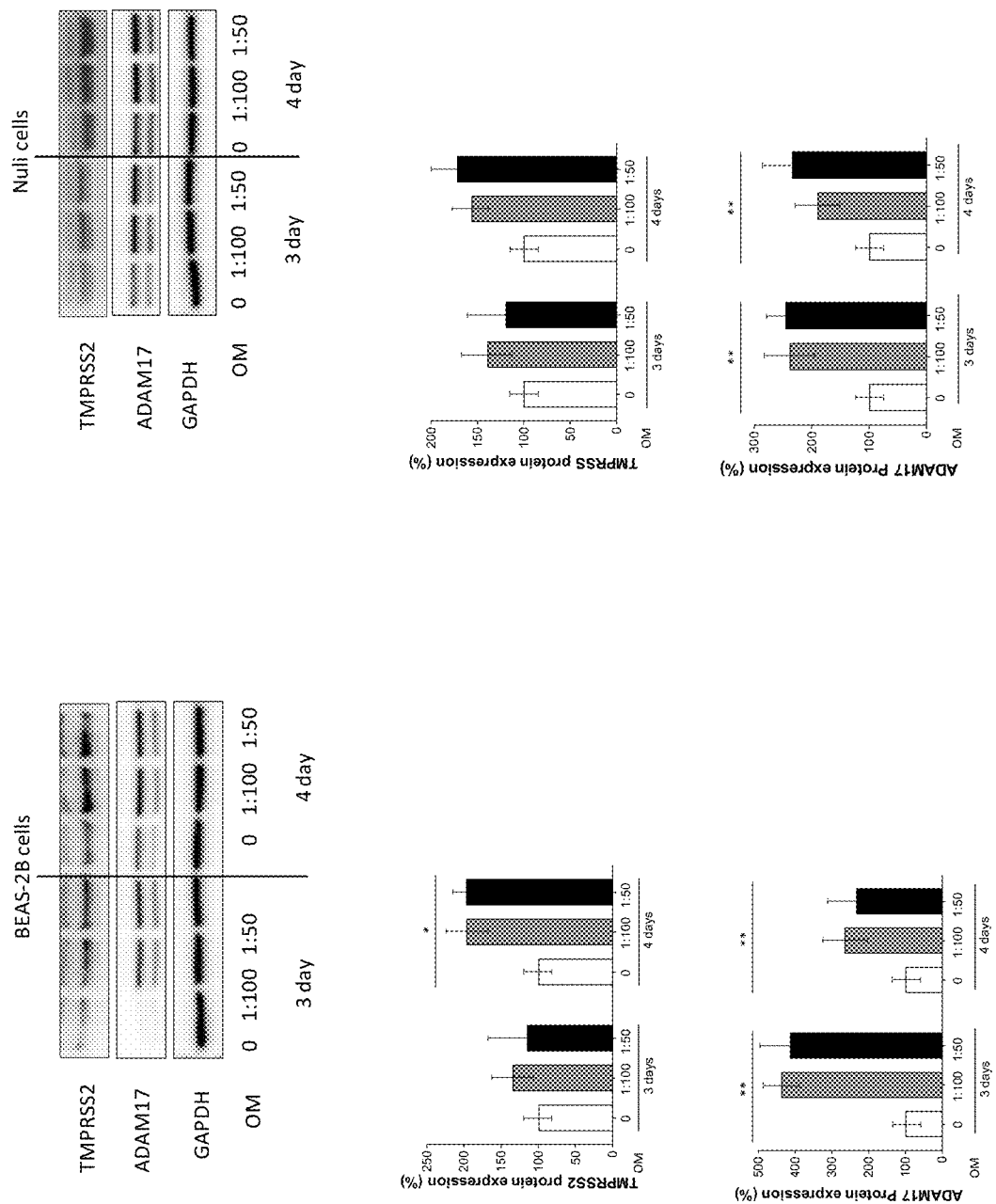
FIG. 35: are Western blots showing that treatment with OM314A bacterial extract (OM) decreased HBEC cells TMPRSS2 and ADAM17 protein expressions (n=3, $*p<0.05$, $**p<0.01$, ANOVA test).
Figure 36:
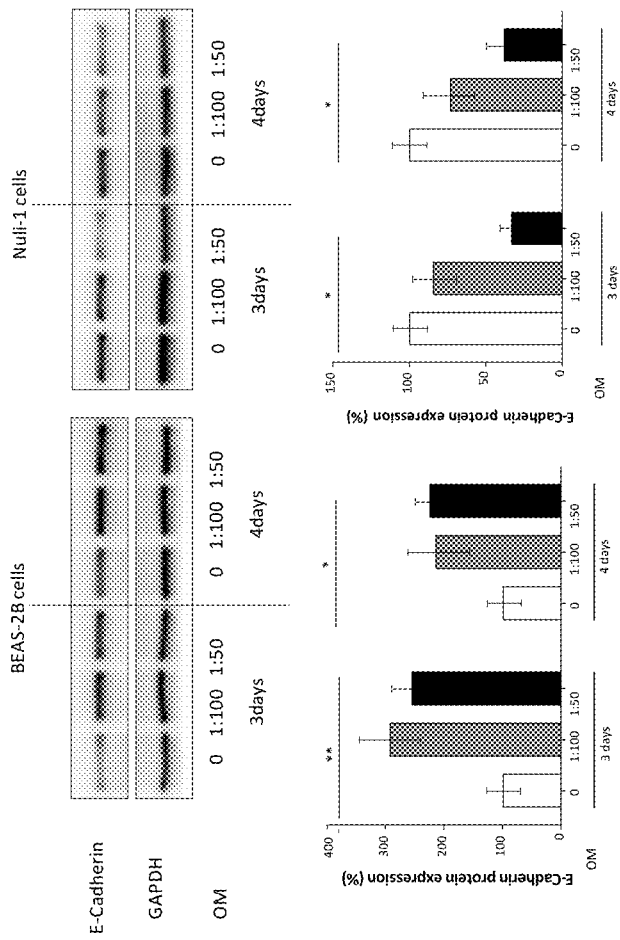
FIG. 36: are Western blots showing that cell line specific effect of OM314A bacterial extract (OM) on HBEC cells E-Cadherin protein expression (n=3, $*p<0.05$, $**p<0.01$, ANOVA test).

Repeated treatment with the OM314A bacterial extract induced a concentration dependent response on ACE2, TMPRSS2, DPP4, and ADAM17 expression. Western blot showed that OM314A bacterial extract decreased ACE2 expression, whereas it increased the expression of TMPRSS2 and ADAM17. Significance was observed after day 2-3. RT-PCR indicated that OM314A bacterial extract reduced ACE2 genes expression by 15-20% compared to untreated cells (FIGS. 33 and 34). In addition, OM314A bacterial extract significantly upregulated TMPRSS2 and ADAM17 mRNA levels over 200%, whereas DDP4 gene expression was significantly decreased by 50% compared to control (FIGS. 33 and 35). Furthermore, OM314A bacterial extract treatment increased E-Cadherin expression, however, with a cell line specific pattern (FIG. 36).

Example 13: In Vivo Efficacy of OM314A Bacterial Extract Against COVID-19

The SARS-CoV-2 virus pandemic has put a massive struggle on health care systems. The only therapeutical option at the moment is vaccination. Viral mutation may reduce the efficacy of vaccines. We demonstrated that prophylactic immune cell activation using OM314A bacterial extract treatment is beneficial during a coronavirus infection.

Figure 37:
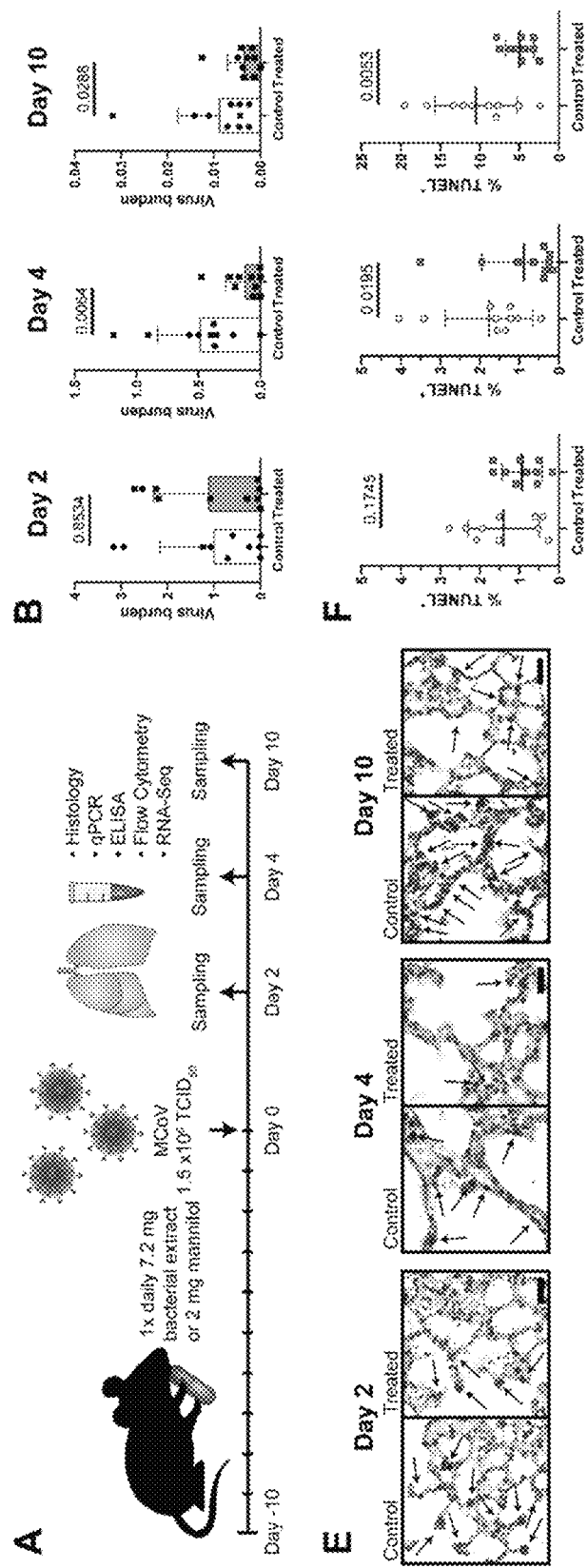
FIGS. 37 (A)-(F): (A) shows the experiment protocol wherein OM314A bacterial extract was applied for 10 days before mouse coronavirus (MCoV) challenge. (B) and (E) are qPCR and histochemistry graphs showing a significant reduction of the viral load in OM314A bacterial extract treated animals on day 4 and 10 compared to control. (F) shows that OM314A bacterial extract treated animals had significantly reduced TUNEL positive cells at day 4 and 10.

A mouse coronavirus (MCoV) belonging to the same virus subfamily as SARSCoV-2. OM314A bacterial extract was applied for 10 days before MCoV challenge. Viral load was significantly reduced in OM314A bacterial extract treated animals on day 4 and 10 compared to control (qPCR and histochemistry—FIG. 37). In addition to viral burden, lung apoptosis was also investigated and revealed that OM314A bacterial extract treated animals had significantly reduced TUNEL positive cells at day 4 and 10 and cleaved caspase 3 positive cells at day 10, indicative of its effect in reducing lung cell apoptosis (FIG. 37).

Figure 38:
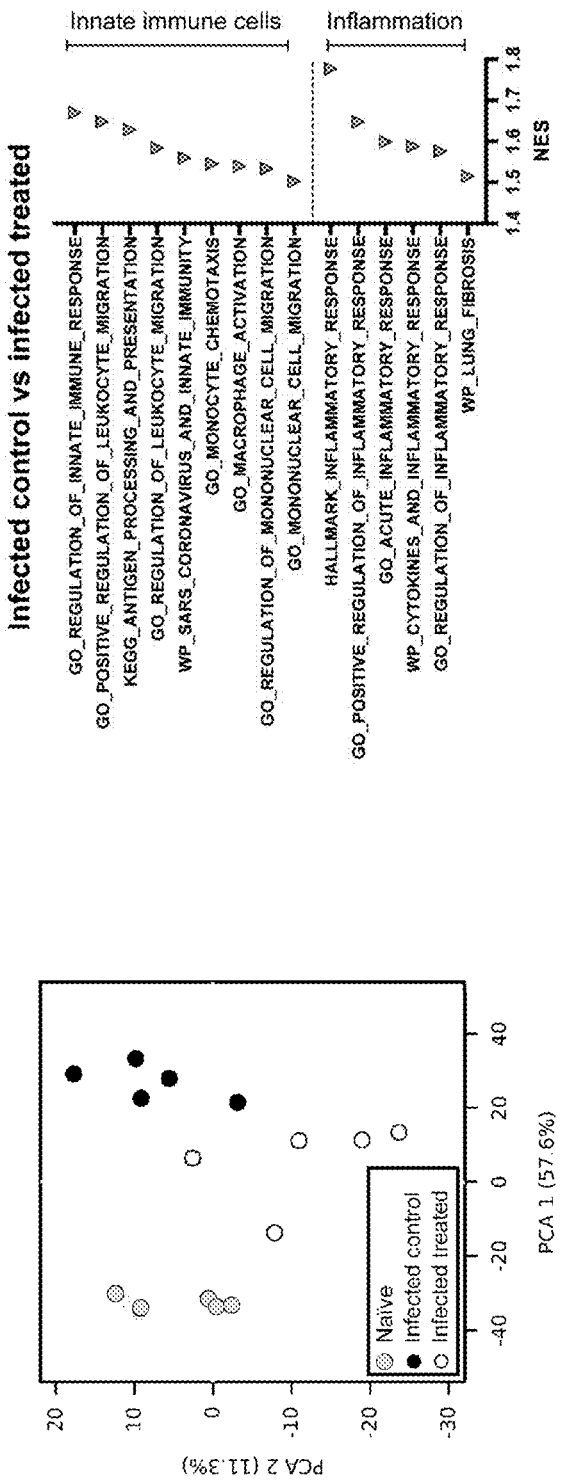
FIG. 38: are graphs showing the difference of RNA sequencing of lung tissue at day 4 of OM314A bacterial extract treated versus control untreated animals after virus infection.

To analyze involved pathways in this antiapoptotic protection we performed RNA sequencing on healthy and virus infected lungs with or without OM314A bacterial extract treatment at day 4 (FIG. 38, left side). We found that OM314A bacterial extract treatment led to a phenotype closer to healthy lung tissue then to disease tissue with already reduced interferon expression (FIG. 38). Mechanistically OM314A bacterial extract increased lung macrophages 10 days after treatment and enhanced antigen presenting molecules within the lung.

Figure 39:
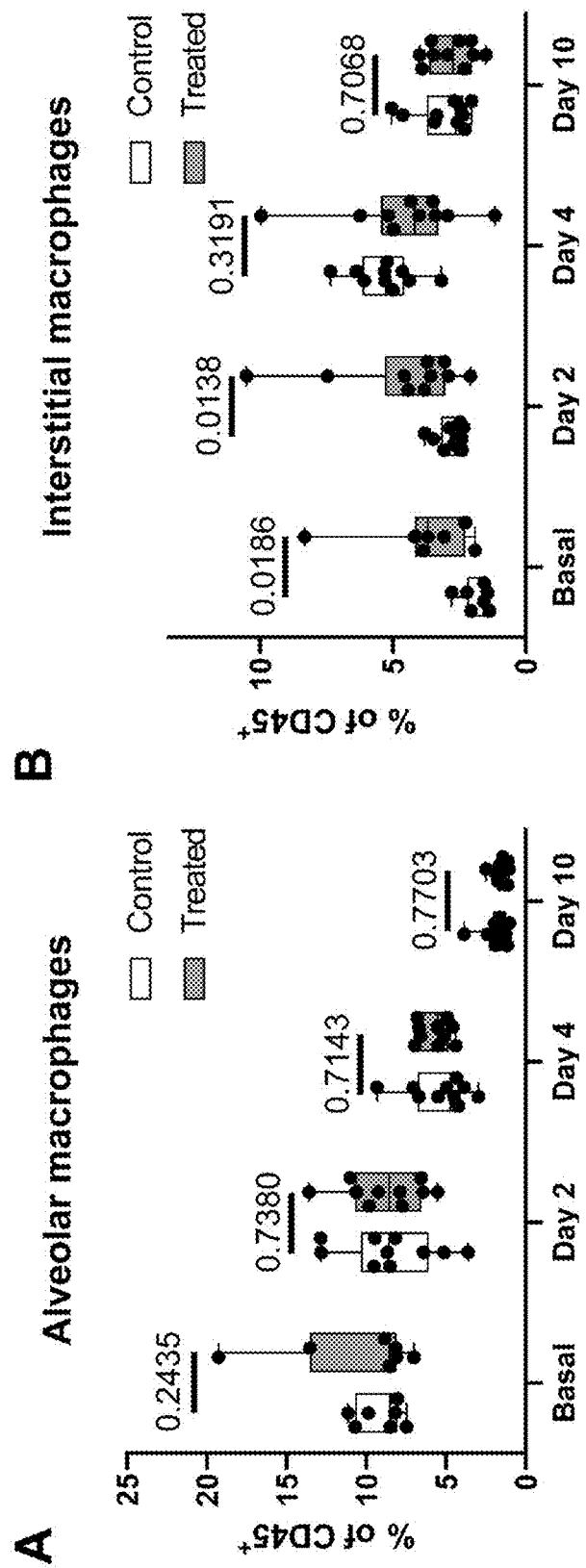
FIG. 39: are graphs showing the presence of alveolar macrophages and interstitial macrophages in OM314A bacterial extract Treated versus Control (untreated) animals at day 2, day 4 and day 10 after virus infection (n=7-10).
Figure 40:
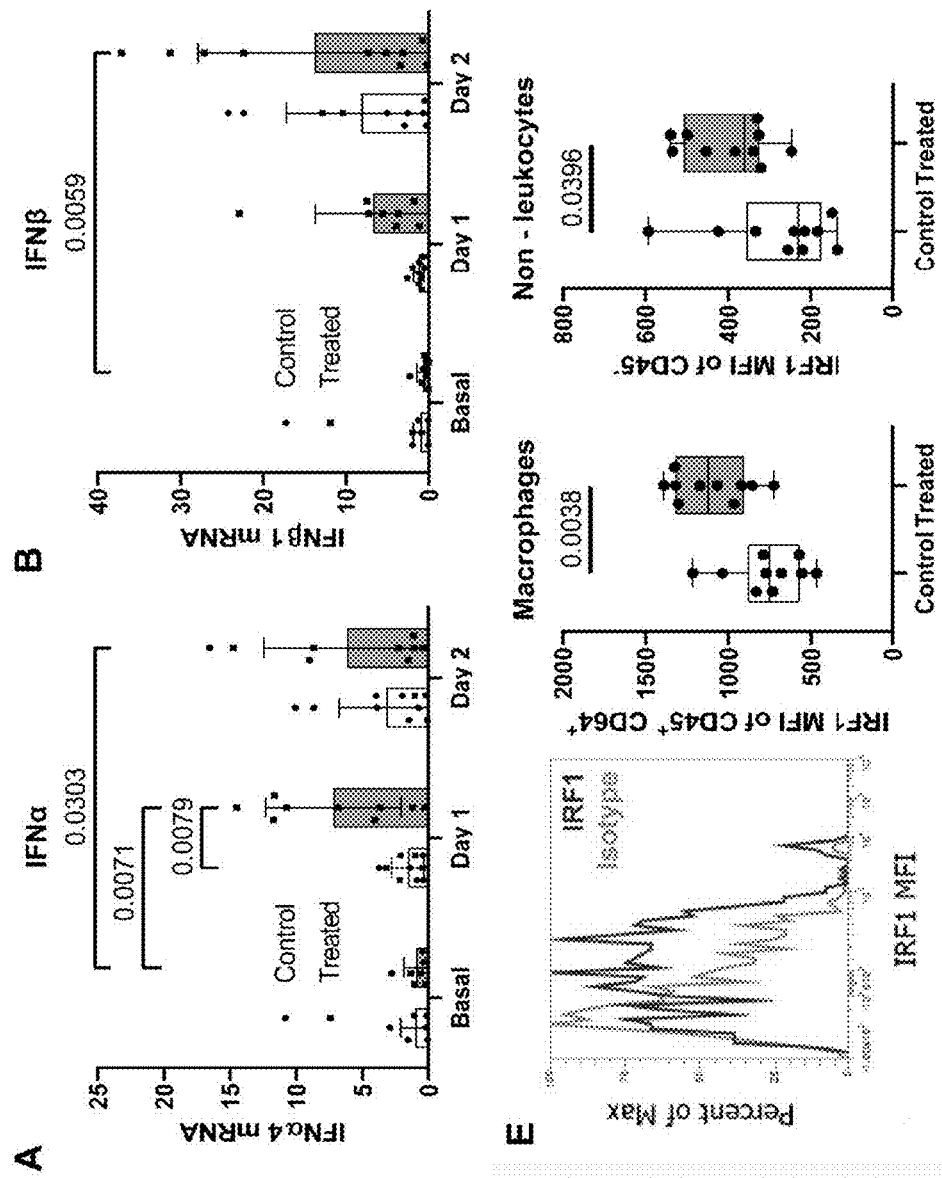
FIG. 40: are graphs showing the increase of early interferon pathway gene activation, including interferon-alpha and interferon-beta (A and B). On a cellular level indicated cells showed significantly more interferon regulatory factor 1 (IRF1) protein at day 1 in OM314A treated animals as compared to control animals as identified by flow cytometry (E).

To determine if an increased number of macrophages was part of the protection observed in OM314A bacterial extract treated animals, we transplanted lung macrophages from healthy animals into recipient mice. Indeed, mice that received a macrophage cell transplant showed reduced viral load at day 4 of MCoV infection in the lung (FIG. 39) resulting in an enhanced and faster activation of interferon and its downstream targets (FIG. 40).

Figure 41:
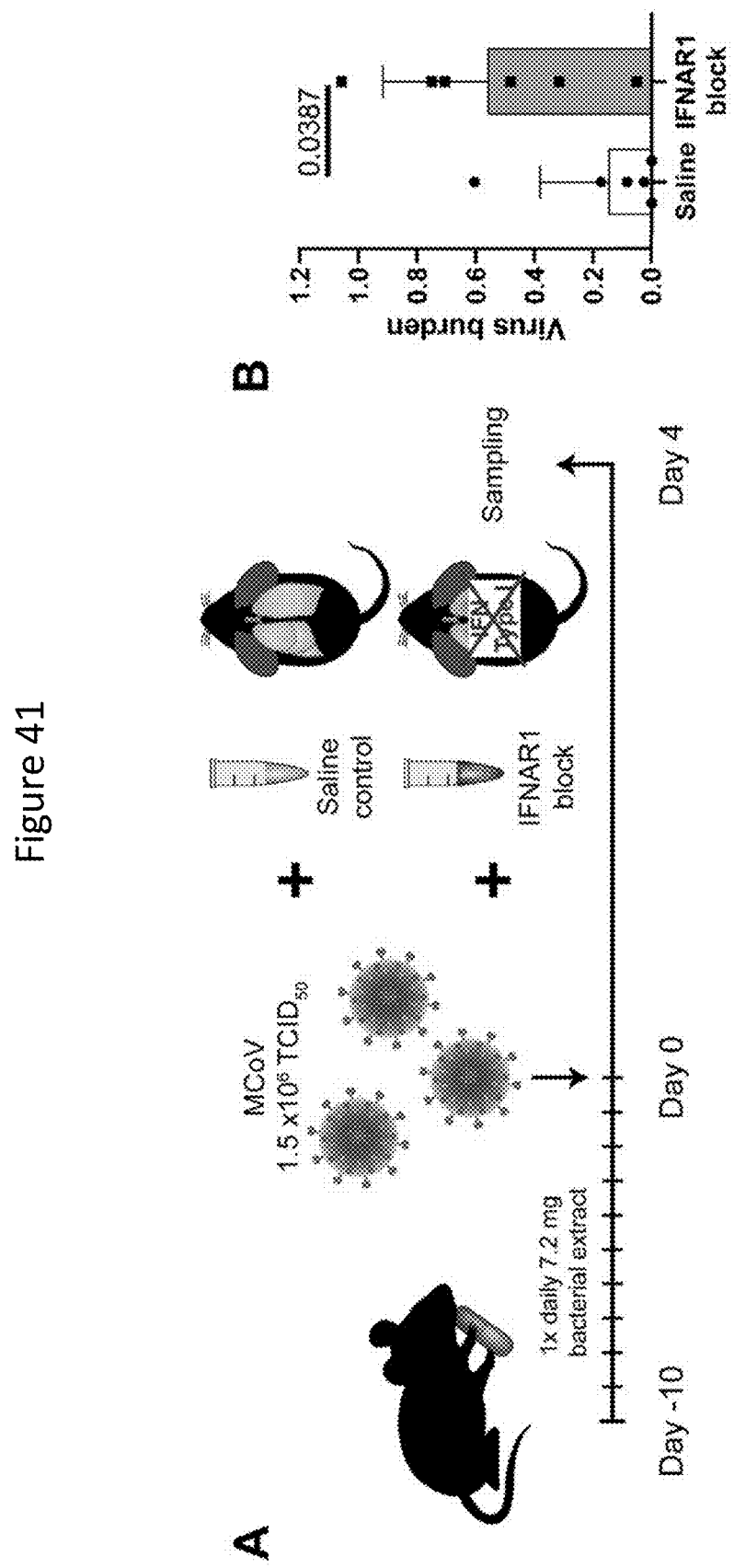
FIG. 41: shows a protocol for pre-treatment with OM314A bacterial extract and the effect on early interferon activation inhibition of interferon alpha and beta precursor subunit 1 (IFNAR1).

These data clearly showed that OM314A bacterial extract enhances viral clearance and lung integrity by increasing lung macrophages leading to enhanced coronavirus clearance and reduced lung apoptosis. Confirmation of such and for the role of the antiviral interferon response was demonstrated in an additional experiment where interferon response was blocked by IFNAR1 antibodies (FIG. 41).

In conclusion, these data demonstrated that mice pretreated with OM314A bacterial extract according to the present invention showed (1) an increase of lung interstitial macrophages, (2) a faster interferon response to coronavirus challenge, (3) an increased viral resolution, and (4) a reduced tissue damage.

Example 14: Direct Perioral (Airway) Administration of OM314A Bacterial Extract is Superior to Oral Treatment in a Superinfection Model (FIGS. 3-13)

OM314A bacterial extract is a standardized bacterial extract made of 21 strains of lung pathogenic bacteria isolated from human airways is widely used via oral administration to prevent recurrences of respiratory infections. Its prophylactic oral administration was shown to protect against influenza and subsequent bacteria in a superinfection model in mice.

OM314A bacterial extract was also shown to induce several anti-viral signals including type I IFN-0 via Toll-like receptor adaptor Trif and MyD88. Among several other anti-viral protective effects, the release of beta defensin occurred independently from hRV-A cell infection in epithelial cells obtained by bronchoscopy from control, COPD or asthma patients.

Perioral routes of administration such as intranasal and intratracheal routes were investigated in a super-infection model of first influenza intranasal inoculation followed by a sublethal infection of *Streptococcus pneumoniae* 7 days later (FIGS. 3-13). Different doses and number of treatments via oral route or intranasal route were explored in prophylactic settings in BALB/c mice inoculated with 100 PFU of influenza virus intranasally. Influenza virus load was determined in the lungs 5 days after virus inoculation.

Results have showed that prophylactic intranasal and direct lung administration of OM314A bacterial extract according to the present invention superinfection animal model resulted in a significant reduction of morbidity and mortality of said superinfected animals, reduced viral titer in lung tissue following influenza infection. These protective effects were dose dependent, and showed higher efficacy as compared to oral administration.

These data clearly showed that topic perioral administration of OM314A bacterial extract according to the present invention directly to the airway compartment protects from viral infections and bacterial superinfections at lower doses and with a higher efficacy as compared to the oral route.

The invention claimed is:

1. A physically stabilized bacterial extract liquid preparation obtained by alkaline lysis of Gram positive or Gram negative bacterial species chosen among *Moraxella catarrhalis, Haemophilus influenzae, Klebsiella pneumoniae, Staphylococcus aureus, Streptococcus pneumoniae, Streptococcus pyogenes, Streptococcus sanguinis, Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis,* and/or *Lactobacillus delbrueckii* and neutralization with one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, followed by purification by filtration of the neutralized extract and adjusting to a final physiological pH by adding the one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, and a combination thereof used for said neutralization, wherein said bacterial extract comprises less than 100 microgram/ml nucleic acids.

2. The bacterial extract according to claim 1, wherein said purification comprises filtration with filters of 1.2 micron to 0.1 micron, or filters of 0.65 to 0.2 micron, or filters of 0.45 micron.

3. The bacterial extract according to claim 1, wherein said alkaline lysis is conducted at pH greater than 10 or greater than 10.0.

4. The bacterial extract according to claim 1, wherein the final pH is adjusted between 5 and 8, between 6 and 8, between 6.3 and 7.8, or between 6.5 and 7.8.

5. The bacterial extract according to claim 1, wherein said stable purified bacterial extract comprises at least 0.1 mg/mL of saccharides.

6. The bacterial extract according to claim 1, said bacterial extract being stable in liquid form at room temperature, 4° C., −20° C., or at −80° C.

7. A pharmaceutical composition comprising the bacterial extract of claim 1 and a pharmaceutically acceptable excipient or vehicle, and wherein said pharmaceutical composition is in the form of a solid, semi-solid, liquid, or aerosol formulation, and wherein said composition is formulated for intranasal, intratracheal, mucosal, transmucosal, external skin topical, buccal, sublingual, oral, pulmonary, intrabronchial, and/or intrapulmonary routes of administration.

8. The pharmaceutical composition of claim 7, wherein said pharmaceutical composition is liquid or aerosol and is formulated in a spray, droplet, colloidal, mist, nebulae, and/or in atomized vapor, or wherein said composition is liquid or semi-solid and is formulated in form of emulsions, microemulsions, aqueous dispersions, oils, milks, balsams, foams, aqueous or oily lotions, aqueous or oily gels, creams, solutions, hydroalcoholic solutions, hydroglycolic solutions, hydrogels, serums, ointments, mousses, pastes, or transdermal patches, or wherein said composition is solid and is formulated in a powder, and/or crushable tablet.

9. A method of treating and/or preventing acute and chronic immunological disorders resulting from infections and/or inflammation and/or neoplasms and/or dysbiosis, comprising administering an effective amount of the bacterial extract of claim 1.

10. The method of claim 9, wherein said immunological disorders are chosen among imbalance between T helper 1, T helper 17 and T helper 2 immune response, imbalance of T reg, type 2 hypersensitivity, immuno-suppression, eosinophilia, allergy or atopy.

11. The method of claim 9, wherein said infections are chosen among upper and lower respiratory tract infections and/or associated sequelae, and wherein said infections may further comprise secondary infections, bacterial secondary infections following viral infections with influenza, non-respiratory viral infections, non-respiratory bacterial infections, or systemic infections.

12. The method of claim 9, wherein said infections are chosen among viral infections, influenza, respiratory syncytial virus, rhinovirus, coronavirus, CoV, SARS-CoV, and MERS-CoV.

13. The method of claim 9, wherein said infection is COVID-19.

14. The method of claim 9, wherein said inflammations are chosen among allergic/atopic respiratory and non-respiratory indications atopic dermatitis, acute and/or chronic associated dermatitis, anaphylaxis or food allergies, or wherein said inflammations comprise skin disorders, inflamed skin, eczema, rosacea, atopic dermatitis, psoriasis, actinic keratosis, or wherein said inflammations are eosinophilic indications or wherein said inflammations are chosen among T helper 2 predominant autoimmune indications.

15. The method of claim 9, wherein dysbiosis related disorders are chosen among obesity, asthma, diabetes, autoimmune diseases, diseases associated with low fiber regimens, atopic dermatitis, acute and/or chronic associated dermatitis, or wherein dysbiosis related disorders are chosen among inflammatory bowel diseases, comprising ulcerative colitis, Crohn's disease, colitis, type 2 diabetes, autoimmune diseases, or diseases associated with low fiber regimens.

16. A delivery device comprising the pharmaceutical composition according to claim 7, said delivery device being selected from the group comprising of nasal insufflator device, intranasal inhaler, intranasal spray device, atomizer, nasal spray bottle, unit dose container, pump, dropper, squeeze bottle, nebulizer, metered dose inhaler (MDI), pressurized dose inhalers, insufflators, bi-directional devices, dose ampoules, nasal pads, nasal sponges, and nasal capsules.

17. A process for preparing a physically stabilized bacterial extract liquid preparation, comprising the following steps:
   (a) culturing a Gram positive or Gram negative bacterial species chosen among *Moraxella catarrhalis, Haemophilus influenzae, Klebsiella pneumoniae, Staphylococcus aureus, Streptococcus pneumoniae, Streptococcus pyogenes, Streptococcus sanguinis, Lactobacillus fermentum, Lactobacillus rhamnosus, Lactobacillus plantarum, Lactobacillus johnsonii, Lactobacillus helveticus, Lactobacillus casei* defensis, *Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis,* and/or *Lactobacillus delbrueckii* in a suitable culture medium,
   (b) heat killing the bacteria, removing the culture medium and harvesting the concentrated biomass,
   (c) lysing each strain at an initial pH of greater than 10,
   (d) decreasing the pH of the extract(s) obtained in step (c) by 1 or 2 units by adding one or more organic acid selected among acetic acid, propionic acid, lactic acid, 3-hydroxypropanoic acid, pyruvic acid, butanoic acid, 2-hydroxybutanoic acid, 3-hydroxybutanoic acid, glutamic acid, aspartic acid, a combination thereof, or pharmaceutically acceptable salts and esters thereof, and
   (d) passing the product of step (d) at least once through a microfilter and retaining the product on an ultrafilter so as to obtain a purified soluble extract.

18. The method of claim 14, wherein said eosinophilic indications are chosen between eosinophilic asthma and eosinophilic pneumonia.

19. The bacterial extract of claim 1, wherein the one or more organic acid does not include pyruvic acid.

20. The bacterial extract of claim 1, wherein the bacterial species is chosen among *Moraxella catarrhalis, Haemophilus influenzae, Klebsiella pneumoniae, Staphylococcus aureus, Streptococcus pneumoniae, Streptococcus pyogenes,* and/or *Streptococcus sanguinis.*

21. The bacterial extract of claim 1, wherein the bacterial species is chosen among *Lactobacillus fermentum, Lactobacillus rhamnosus, Lactobacillus plantarum, Lactobacillus johnsonii, Lactobacillus helveticus, Lactobacillus casei* defensis, *Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius, Lactobacillus lactis,* and/or *Lactobacillus delbrueckii.*

22. The bacterial extract of claim 1, wherein the bacterial species is chosen among *Lactobacillus fermentum* and/or *Lactobacillus helveticus.*

23. The bacterial extract of claim 22, wherein the one or more organic acid is propionic acid.

24. The method of claim 11, wherein said infections are chosen among allergic rhinitis, rhinitis, nasopharyngitis, sinusitis, Hypersensitivity Pneumonitis, bronchopneumonia, bronchitis, bronchiolitis, pneumonia, obstructive pulmonary disease with acute lower respiratory infection, obstructive pulmonary disease with acute upper respiratory infections, and diseases with epithelial cilia motion disorders and/or mucus clearance disorders.

25. The method of claim 11, wherein said systemic infections are chosen among sepsis, septic shock, and viral-induced complications.

* * * * *